United States Patent
Lançois et al.

(10) Patent No.: US 11,491,157 B2
(45) Date of Patent: Nov. 8, 2022

(54) CYCLOALKYL SUBSTITUTED PYRAZOLOPYRIMIDINES HAVING ACTIVITY AGAINST RSV

(71) Applicant: Janssen Sciences Ireland Unlimited Company, Co Cork (IE)

(72) Inventors: David Francis Alain Lançois, Louviers (FR); Jérôme Émile Georges Guillemont, Andé (FR); Pierre Jean-Marie Bernard Raboisson, Wavre (BE); Dirk André Emmy Roymans, Turnhout (BE); Peter Rigaux, Overijse (BE); Antoine Benjamin Michaut, Le Vaudreuil (FR)

(73) Assignee: Janssen Sciences Ireland Unlimited Company Co Cork, IE, County Cork (IE)

( * ) Notice: Subject to any disclaimer, the term of this patent is extended or adjusted under 35 U.S.C. 154(b) by 2 days.

(21) Appl. No.: 16/966,411

(22) PCT Filed: Jan. 30, 2019

(86) PCT No.: PCT/EP2019/052209
§ 371 (c)(1),
(2) Date: Jul. 30, 2020

(87) PCT Pub. No.: WO2019/149734
PCT Pub. Date: Aug. 8, 2019

(65) Prior Publication Data
US 2020/0360387 A1 Nov. 19, 2020

(30) Foreign Application Priority Data
Jan. 31, 2018 (EP) ..................................... 18154314

(51) Int. Cl.
C07D 487/04 (2006.01)
A61K 31/519 (2006.01)
A61P 31/12 (2006.01)

(52) U.S. Cl.
CPC ............ *A61K 31/519* (2013.01); *A61P 31/12* (2018.01); *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 5,972,966 A | 10/1999 | deSolms | |
| 5,977,134 A | 11/1999 | Ciccarone et al. | |
| 6,177,443 B1 | 1/2001 | Madsen et al. | |
| 6,218,404 B1 | 4/2001 | Bigge et al. | |
| 6,608,203 B2 | 8/2003 | Cameron et al. | |
| 6,765,096 B1 | 7/2004 | Aono et al. | |
| 6,919,376 B2 | 7/2005 | Llompart et al. | |
| 7,507,842 B2 | 3/2009 | Oehler et al. | |
| 7,642,272 B2 | 1/2010 | Shankar et al. | |
| 7,662,826 B2 | 2/2010 | Seno et al. | |
| 7,893,096 B2 | 2/2011 | Valiante, Jr. | |
| 8,450,343 B2 | 5/2013 | Huang et al. | |
| 8,691,938 B2 | 4/2014 | DeGoey et al. | |
| 8,829,027 B2 | 9/2014 | Eckhardt et al. | |
| 8,946,238 B2 | 2/2015 | Boojamra et al. | |
| 10,208,048 B2 | 2/2019 | Lançois | |
| 10,611,769 B2 | 4/2020 | Lançois | |
| 2003/0073681 A1 | 4/2003 | Hauske et al. | |
| 2010/0063047 A1 | 3/2010 | Borchardt et al. | |
| 2010/0204265 A1 | 8/2010 | Baskaran et al. | |

FOREIGN PATENT DOCUMENTS

| | | |
|---|---|---|
| CN | 105777632 A | 7/2016 |
| WO | 199619483 A1 | 6/1996 |
| WO | 199701275 A1 | 1/1997 |
| WO | 2004029042 A1 | 4/2004 |
| WO | 2004037817 A1 | 6/2004 |
| WO | 2005000315 A1 | 1/2005 |
| WO | 2005035516 A1 | 4/2005 |
| WO | 2005042530 A1 | 5/2005 |
| WO | 2005058871 A1 | 6/2005 |

(Continued)

OTHER PUBLICATIONS

Hallack et al., "Glycosaminoglycan Sulfation Requirements for Respiratory Syncytial Virus Infection," Journal of Virology, vol. 74(22):pp. 10508-10513 (Nov. 2000).
Wyde et al., "CL387626 exhibits marked and unusual antiviral activity against respiratory syncytial virus in tissue culture and in cotton rats", Antiviral Research, vol. 38: pp. 31-42 (1998).
International Search Report and Written Opinion dated Jun. 4, 2019 for PCT Patent Application No. PCT/EP2019/052209.

(Continued)

*Primary Examiner* — Benjamin J Packard
(74) *Attorney, Agent, or Firm* — Janssen Sciences Ireland Unlimited Company Co Cork, IE

(57) ABSTRACT

The invention concerns compounds of formula (I) having antiviral activity, in particular, having an inhibitory activity on the replication of the respiratory syncytial virus (RSV). The invention further concerns pharmaceutical compositions comprising these compounds and the compounds for use in the treatment of respiratory syncytial virus infection. (Formula I).

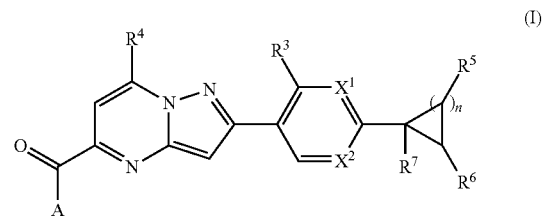

16 Claims, No Drawings

(56) References Cited

FOREIGN PATENT DOCUMENTS

| | | |
|---|---|---|
| WO | 2005061513 A1 | 7/2005 |
| WO | 2006030925 A1 | 3/2006 |
| WO | 2006034341 A2 | 3/2006 |
| WO | 2006136561 A1 | 12/2006 |
| WO | 2007044085 A2 | 4/2007 |
| WO | 2007060409 A1 | 5/2007 |
| WO | 2008063671 A2 | 5/2008 |
| WO | 2009023179 A2 | 2/2009 |
| WO | 2010104306 A2 | 9/2010 |
| WO | 2010111058 A1 | 9/2010 |
| WO | 2011163518 A1 | 12/2011 |
| WO | 2012051361 A1 | 4/2012 |
| WO | 2015042297 A1 | 3/2015 |
| WO | 2015106025 A1 | 7/2015 |
| WO | 2016017980 A1 | 2/2016 |
| WO | 2016071293 A2 | 5/2016 |
| WO | 2016091774 | 6/2016 |
| WO | 2016174079 A1 | 11/2016 |
| WO | 2019106004 A1 | 6/2019 |
| WO | 2019149734 A1 | 8/2019 |
| WO | 2019206828 A1 | 10/2019 |
| WO | 2020109224 A1 | 6/2020 |
| WO | 2020234333 A1 | 11/2020 |

OTHER PUBLICATIONS

Herr, "5-Substituted-1H-tetrazoles as Carboxylic Acid Isosteres: Medicinal Chemistry and Synthetic Methods", Bioorganic & Medicinal Chemistry, 2002, pp. 3379-3393, vol. 10.

International Search Report and Written Opinion for PCT/EP2016/059392 dated Jul. 14, 2016.

International Search Report and Written Opinion for PCT/EP2018/082828 dated Jan. 30, 2019.

International Search Report and Written Opinion for PCT/EP2019/060216 dated May 17, 2019.

International Search Report and Written Opinion for PCT/EP2019/082404 dated Jan. 28, 2020.

International Search Report and Written Opinion for PCT/EP2020/064030 dated Sep. 14, 2020.

CYCLOALKYL SUBSTITUTED PYRAZOLOPYRIMIDINES HAVING ACTIVITY AGAINST RSV

CROSS-REFERENCE TO RELATED APPLICATIONS

This application is a national phase entry of International Application No. PCT/EP2019/052209, filed on Jul. 30, 2019, which claims priority to EP Patent Application No. 18154314.1, filed on Jan. 31, 2018, each of which is incorporated herein in its entirety.

FIELD OF THE INVENTION

The invention concerns compounds having antiviral activity, in particular, having an inhibitory activity on the replication of the respiratory syncytial virus (RSV). The invention further concerns pharmaceutical compositions comprising these compounds and the compounds for use in the treatment of respiratory syncytial virus infection.

BACKGROUND

Human RSV or Respiratory Syncytial Virus is a large RNA virus, member of the family of Pneumoviridae, genus *Orthopneumovirus* together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Reinfection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. Synagis® (palivizumab a monoclonal antibody, is used for passive immunoprophylaxis. Athough the benefit of Synagis® has been demonstrated, the treatment is expensive, requires parenteral administration and is restricted to children at risk for developing severe pathology.

Clearly there is a need for an efficacious non-toxic and easy to administer drug against RSV replication. It would be particularly preferred to provide drugs against RSV replication that could be administered perorally.

Compounds that exhibit anti-RSV activity are disclosed in WO-2016/174079.

DETAILED DESCRIPTION OF THE INVENTION

The present invention relates to compounds of formula (I)

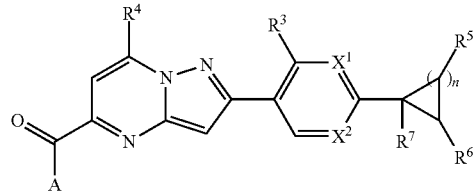

(I)

including any stereochemically isomeric form thereof, wherein
A is

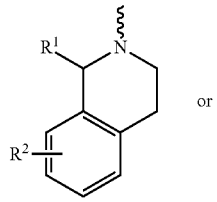

(a-1)

or

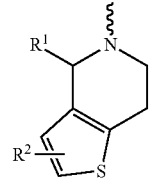

(a-2)

n is 1 or 2;
$X^1$ and $X^2$ are selected from $X^1$ is CH and $X^2$ is CH,
  or $X^1$ is N and $X^2$ is CH,
  or $X^1$ is CH and $X^2$ is N;
$R^1$ is $CH_3$ or $CH_2CH_3$;
$R^2$ is hydrogen, halo or $C_{1-4}$alkyl;
$R^3$ is halo;
$R^4$ is $C_{1-4}$alkyl; $C_{3-6}$cycloalkyl; phenyl; phenyl substituted with 1, 2 or 3 substituents each individually selected from halo, $C_{1-4}$alkyl, $C_{1-4}$alkyloxy, and hydroxy;
$R^5$ is hydrogen or $C_{1-4}$alkyl;
$R^6$ is hydroxy;
  cyano;
  $C_{1-4}$alkyl substituted with hydroxy, —(CO)—$NR^{10}R^{11}$ or —O—(CO)—$NR^{10}R^{11}$;
  —(CO)—$NR^{10}R^{11}$;
  —(CO)—$NR^9$—$SO_2$—$R^8$;
  —(CO)—$NR^9$—(CO)—$SO_2$—$R^8$;
  —(CO)-Heterocycle;
  —(CO)—$NR^9$-Heterocycle;
  —O—(CO)—$NR^{10}R^{11}$;
  —$NR^9$—(CO)—$C_{1-4}$alkyl;
  —$NR^9$—(CO)—$C_{3-6}$cycloalkyl;
  —$NR^9$—(CO)—O—$R^8$;
  —$NR^9$—(CO)—$NR^9$—$R^8$;
  —$NR^9$—$SO_2$—$R^8$;
  —$NR^9$—(P=O)-di($C_{1-4}$alkyl);
  —$SO_2$—$R^8$;
  —$SO_2$—$NR^{10}R^{11}$;
  —$SO_2$—$NR^9$—(CO)—$R^8$; or
  Heteroaryl;
$R^7$ is hydrogen, halo, $C_{1-4}$alkyl or —(CO)—$NR^{10}R^{11}$;
$R^8$ is $C_{1-4}$alkyl, polyhalo$C_{1-4}$alkyl, or $C_{3-6}$cycloalkyl;
each $R^9$ is independently selected from hydrogen or $C_{1-6}$alkyl;

$R^{10}$ and $R^{11}$ are each indepently selected from hydrogen; CN; $C_{1-4}$alkyl; $C_{3-6}$alkenyl; polyhalo$C_{1-4}$alkyl; $C_{3-6}$cycloalkyl; $C_{3-6}$cycloalkyl substituted with $C_{1-4}$alkyl; or $C_{1-4}$alkyl substituted with hydroxy or cyano;

Heterocycle is pyrrolidinyl or oxetanyl; and

Heteroaryl is 3-oxo-2,3-dihydro-1,2-oxazolyl, or tetrazolyl, wherein each Heteroaryl is optionally substituted with one or two substituents each independently selected from $C_{1-4}$alkyl, halo, amino, and aminocarbonyl;

provided that when $R^6$ is —$NR^9$—(CO)—$C_{3-6}$cycloalkyl then $X^1$ is CH and $X^2$ is CH;

or a pharmaceutically acceptable acid addition salt thereof.

As used in the foregoing definitions:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like;

$C_{1-6}$alkyl is meant to include $C_{1-4}$alkyl and the higher homologues thereof having 5 or 6 carbon atoms, such as, for example, 2 methylbutyl, pentyl, hexyl and the like;

$C_{3-6}$cycloalkyl is generic to cyclopropyl, cyclobutyl, cyclopentyl, and cyclohexyl;

polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like;

—(CO)— or (CO) means carbonyl.

The term "compounds of the invention" as used herein, is meant to include the compounds of formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I)" and "intermediates of synthesis of formula (I)" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration.

The term "stereoisomers" also includes any rotamers, also called conformational isomers, the compounds of formula (I) may form.

Therefore, the invention includes enantiomers, diastereomers, racemates, E isomers, Z isomers, cis isomers, trans isomers, rotamers, and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms in so far as they may exist, although not explicitly indicated in the above formula (I) are intended to be included within the scope of the present invention.

It follows that a single compound may exist in both stereoisomeric and tautomeric form.

Atropisomers (or atropoisomers) are stereoisomers which have a particular spatial configuration, resulting from a restricted rotation about a single bond, due to large steric hindrance. All atropisomeric forms of the compounds of formula (I) are intended to be included within the scope of the present invention.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

For the avoidance of doubt, compounds of formula (I) may contain the stated atoms in any of their natural or non-natural isotopic forms. In this respect, embodiments of the invention that may be mentioned include those in which (a) the compound of formula (I) is not isotopically enriched or labelled with respect to any atoms of the compound; and (b) the compound of formula (I) is isotopically enriched or labelled with respect to one or more atoms of the compound. Compounds of formula (I) that are isotopically enriched or labelled (with respect to one or more atoms of the compound) with one or more stable isotopes include, for example, compounds of formula (I) that are isotopically enriched or labelled with one or more atoms such as deuterium, $^{13}C$, $^{14}C$, $^{14}N$, $^{15}O$ or the like.

A first group of compounds are compounds of formula (I) wherein $X^1$ is CH and $X^2$ is CH.

A second group of compounds are compounds of formula (I) wherein $X^1$ is N and $X^2$ is CH, or $X^1$ is CH and $X^2$ is N.

A third group of compounds are compounds of formula (I) wherein wherein radical A is of formula (a-1).

A fourth group of compounds are compounds of formula (I) wherein radical A is of formula (a-2).

A fifth group of compounds are compounds of formula (I) wherein n=1.

A sixth group of compounds are compounds of formula (I) wherein n=2.

Another group of compounds are compounds of formula (I) wherein $R^6$ is hydroxy.

Another group of compounds are compounds of formula (I) wherein $R^6$ is cyano.

Another group of compounds are compounds of formula (I) wherein $R^6$ is $C_{1-4}$alkyl substituted with hydroxy, —(CO)—$NR^{10}R^{11}$ or —O—(CO)—$NR^{10}R^{11}$.

Another group of compounds are compounds of formula (I) wherein $R^6$ is —(CO)—$NR^{10}R^{11}$.

Another group of compounds are compounds of formula (I) wherein $R^6$ is —(CO)—$NR^9$—$SO_2$—$R^8$.

Another group of compounds are compounds of formula (I) wherein $R^6$ is —(CO)—$NR^9$—(CO)—$SO_2$—$R^8$.

Another group of compounds are compounds of formula (I) wherein $R^6$ is —(CO)-Heterocycle.

Another group of compounds are compounds of formula (I) wherein $R^6$ is —(CO)—$NR^9$-Heterocycle.

Another group of compounds are compounds of formula (I) wherein $R^6$ is —O—(CO)—$NR^{10}R^{11}$.

Another group of compounds are compounds of formula (I) wherein $R^6$ is —$NR^9$—(CO)—$C_{1-4}$alkyl.

Another group of compounds are compounds of formula (I) wherein $R^6$ is —$NR^9$—(CO)—$C_{3-6}$cycloalkyl.

Another group of compounds are compounds of formula (I) wherein $R^6$ is —$NR^9$—(CO)—O—$R^8$.

Another group of compounds are compounds of formula (I) wherein $R^6$ is —$NR^9$—(CO)—$NR^9$—$R^8$.

Another group of compounds are compounds of formula (I) wherein $R^6$ is —$NR^9$—$SO_2$—$R^8$.

Another group of compounds are compounds of formula (I) wherein $R^6$ is —$NR^9$—(P=O)-di($C_{1-4}$alkyl).

Another group of compounds are compounds of formula (I) wherein $R^6$ is —$SO_2$—$R^8$.

Another group of compounds are compounds of formula (I) wherein $R^6$ is —$SO_2$—$NR^{10}R^{11}$.

Another group of compounds are compounds of formula (I) wherein $R^6$ is —$SO_2$—$NR^9$—(CO)—$R^8$.

Another group of compounds are compounds of formula (I) wherein $R^6$ is Heteroaryl.

Interesting compounds of formula (I) are those compounds of formula (I) wherein one or more of the following restrictions apply:
a) A is a radical of formula (a-1); or
b) A is a radical of formula (a-2); or
c) $R^1$ is methyl; or
d) $R^2$ is hydrogen; or
e) $R^3$ is fluoro; or
f) $R^4$ is cyclopropyl;
g) $R^4$ is phenyl;
h) n=1; or
i) n=2.

Compounds of formula (I) can generally be prepared by reacting an intermediate of formula (II) with an intermediate of formula (III) in a reaction-inert solvent.

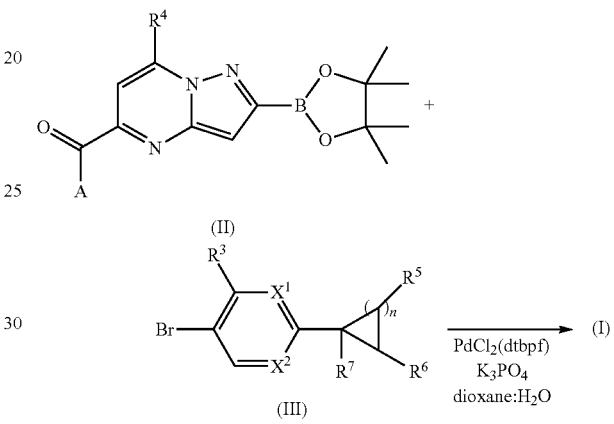

Other synthetic pathways for preparing compounds of formula (I) have been described in the experimental party as general methods of preparation and specific working examples.

The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. in Antiviral Research, 38, p. 31-42 (1998).

Additionally the present invention provides pharmaceutical compositions comprising at least one pharmaceutically acceptable carrier and a therapeutically effective amount of a compound of formula (I). Also provided are pharmaceutical compositions comprising a pharmaceutically acceptable carrier, a therapeutically active amount of a compound of formula (I), and another antiviral agent, in particular a RSV inhibiting compound.

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen free water, before use.

The compounds of formula (I) may also be formulated in rectal compositions such as suppositories or retention enemas, e.g. containing conventional suppository bases such as cocoa butter and/or other glycerides.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections. Other antiviral compounds (b) to be combined with a compound of formula (I) for use in the treatment of RSV are RSV fusion inhibitors or RSV polymerase inhibitors. Specific antiviral compounds for combination with any of the compounds of formula (I) that are useful in the treatment of RSV are the RSV inhibiting compounds selected from ribavirin, lumicitabine, presatovir, ALX-0171, MDT-637, BTA-9881, BMS-433771, YM-543403, A-60444, TMC-353121, RFI-641, CL-387626, MBX-300, 3-({5-chloro-1-[3-(methyl-sulfonyl)propyl]-1H-benzimidazol-2-yl}methyl)-1-cyclopropyl-1,3-dihydro-2H-imidazo[4,5-c]pyridin-2-one, 3-[[7-chloro-3-(2-ethylsulfonyl-ethyl)imidazo[1,2-a]pyridin-2-yl]methyl]-1-cyclopropyl-imidazo[4,5-c]pyridin-2-one, and 3-({5-chloro-1-[3-(methyl-sulfonyl)propyl]-1H-indol-2-yl}methyl)-1-(2,2,2-trifluoroethyl)-1,3-dihydro-2H-imidazo[4,5-c]pyridin-2-one.

The invention will hereinafter be illustrated with reference to the following, non-limiting examples.

EXPERIMENTAL PART

A. Abbreviations

| | |
|---|---|
| μw | microwave |
| AcCl | acetyl chloride |
| AcOH | acetic acid |
| aq. | aqueous |
| br | broad |
| cataCXium ® A | di(1-adamantyl)-n-butylphosphine CAS [321921-71-5] |
| CDI | 1,1'-carbonyldiimidazole CAS [530-62-1] |
| d | doublet |
| DBU | 1,8-diazabicyclo[5.4.0]undec-7-ene CAS [6674-22-2] |
| DCE | 1,2-dichloroethane |
| DCM | dichloromethane |
| DIPE | diisopropyl ether |
| DIPEA | N,N-diisopropylethylamine |
| DMAP | 4-(dimethylamino)pyridine |
| DMF | dimethylformamide |
| DMSO | dimethyl sulfoxide |
| DPPA | diphenyl phosphoryl azide CAS [26386-88-9] |
| $Et_2O$ | diethyl ether |
| $Et_3N$ | triethylamine |
| EtOAc | ethyl acetate |
| EtOH | ethanol |
| h | hour |
| HATU | 1-[bis(dimethylamino)methylene]-1H-1,2,3-triazolo[4,5-b]-pyridinium 3-oxid hexafluorophosphate CAS [148893-10-1] |
| HMDS | hexamethyldisilazane CAS [999-97-3] |
| i-$PrNH_2$ | isopropylamine |
| i-PrOH | isopropyl alcohol |
| m | multiplet |
| m/z | mass-to-charge ratio |
| MeCN | acetonitrile |
| MeOH | methanol |
| min | minute(s) |
| NBS | N-bromosuccinimide CAS [128-08-5] |
| NFSI | N-fluorobenzenesulfonimide CAS [133745-75-2] |
| NMR | nuclear magnetic resonance |
| o/n | overnight |
| P(o-tol)$_3$ | tri(o-tolyl)phosphine CAS [6163-58-2] |
| Pd(OAc)$_2$ | palladium (II) acetate CAS [3375-31-3] |
| PdCl$_2$(dppf)•DCM | [1,1'-bis(diphenylphosphino)ferrocene]dichloropalladium(II), complex with dichloromethane CAS [95464-05-4] |
| PdCl$_2$(dtbpf) | [1,1'-bis(di-tert-butylphosphino)ferrocene]dichloropalladium(II) CAS [95408-45-0] |
| Pd$_2$(dba)$_3$ | tris(dibenzylideneacetone)dipalladium(0) CAS [51364-51-3] |
| ppm | parts per million |
| q | quartet |
| quin | quintuplet |
| Rh$_2$(OPiv)$_4$ | rhodium(II) trimethylacetate, dimer CAS [62728-88-5] |
| rt | room temperature |
| s | singulet |
| sext | sextuplet |
| t | triplet |
| TBDMS | tert-butyldimethylsilyl |
| TBDMSCl | tert-butyldimethylsilyl choride CAS [18162-48-6] |
| t-BuNO | tert-butylnitrite CAS [540-80-7] |
| t-BuOH | tert-butyl alcohol |
| t-BuOK | potassium tert-butoxide |

| | |
|---|---|
| TFA | trifluoroacetic acid CAS [76-05-1] |
| TFAA | trifluoroacetic anhydride CAS [407-25-0] |
| THF | tetrahydrofuran |
| TREAT-HF | triethylamine trihydrofluoride CAS [73602-61-6] |
| XPhos | 2-dicyclohexylphosphino-2',4',6'-triisopropylbiphenyl CAS [564483-18-7] |
| Δ | heat |

The stereochemical configuration for some compounds has been designated as R* or S* (or *R or *S) when the absolute stereochemistry is undetermined although the compound itself has been isolated as a single stereoisomer and is enantiomerically pure.

B. Compound Synthesis

B.1. Preparation of Compounds of Formula (I) with n=1

B.1.1. Synthesis of Intermediates

B.1.1.1. Synthesis of Intermediates A3 and A4

Intermediates A1.i-PrNH$_2$ and A2.i-PrNH$_2$

A1.i-PrNH$_2$: (1S,2S)-2-(4-Bromo-3-fluorophenyl)cyclopropane-1-carboxylic acid; propan-2-amine salt A2.i-PrNH$_2$: (1R,2R)-2-(4-Bromo-3-fluorophenyl)cyclopropane-1-carboxylic acid; propan-2-amine salt

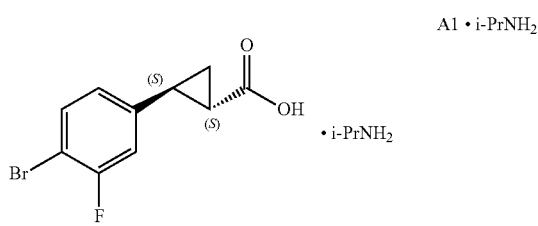

A1 • i-PrNH$_2$

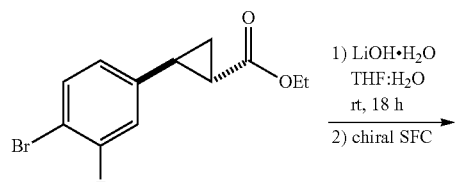

[1202246-03-4]

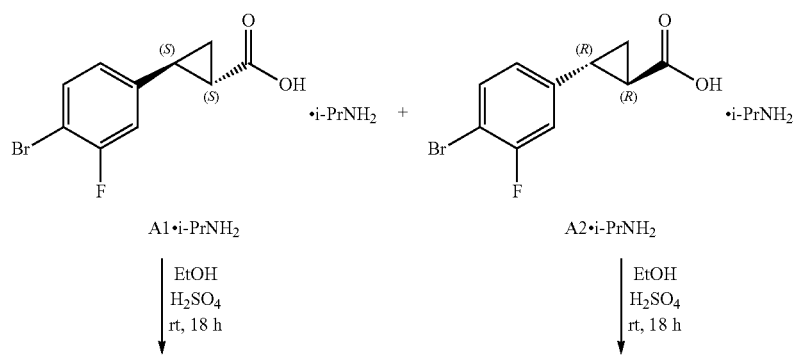

A1•i-PrNH$_2$           A2•i-PrNH$_2$

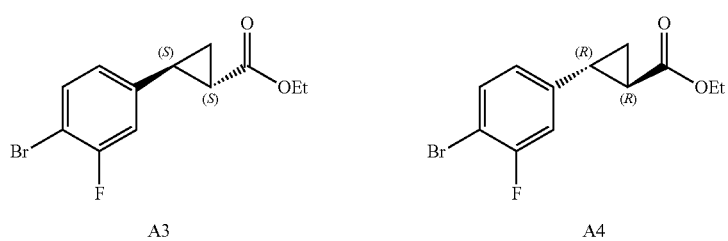

A3           A4

A2 · i-PrNH₂

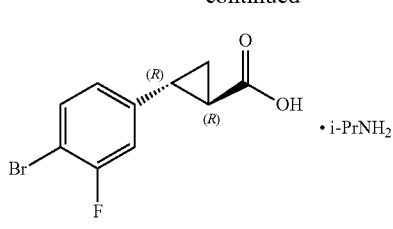

A mixture of ethyl 2-(4-bromo-3-fluorophenyl)cyclopropane-1-carboxylate [1202246-03-4] (184 g, 639 mmol) and lithium hydroxide monohydrate (80.5 g, 1.92 mol) in THF (1.6 L) and H₂O (800 mL) was stirred at rt for 18 h. Brine and a 3M aqueous solution of HCl (~1 L) were added until the pH was acid and the mixture was diluted with EtOAc. The layers were separated and the aqueous phase was extracted with EtOAc (3 times). The combined organic extracts were dried over MgSO₄, filtered and evaporated in vacuo. The crude mixture was purified via chiral SFC (Stationary phase: Chiralpack IC 5 μm 250*50 mm, Mobile phase: 85% CO₂, 15% (50:50 MeOH/i-PrOH (+1% i-PrNH₂)) to give intermediates A2.i-PrNH₂ (90.2 g, 44%) and A1.i-PrNH₂ (96.0 g, 47%).

Intermediate A3

Ethyl (1S,2S)-2-(4-bromo-3-fluorophenyl)cyclopropane-1-carboxylate

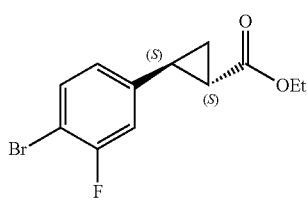

A3

Sulfuric acid (83.0 mL, 1.56 mol) was added to a solution of intermediate A1.i-PrNH₂ (96.0 g, 302 mmol) in EtOH (1 L) (exothermic reaction). The reaction mixture was stirred at rt for 18 h. A saturated aqueous solution of NaHCO₃, water and EtOAc were added. The layers were separated and the aqueous phase was extracted with EtOAc (twice). The combined organic extracts were dried over MgSO₄, filtered and evaporated in vacuo to give intermediate A3 (91.1 g, 99%) as a yellow oil.

Intermediate A4

Ethyl (1R,2R)-2-(4-bromo-3-fluorophenyl)cyclopropane-1-carboxylate

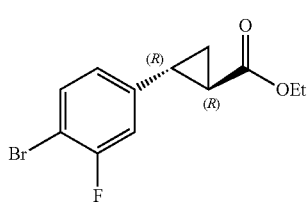

A4

Sulfuric acid (0.86 mL, 16.2 mmol) was added to a solution of intermediate A2d-PrNH₂ (1.00 g, 3.14 mmol) in EtOH (12 mL). The reaction mixture was stirred at rt for 18 h. Water, a saturated aqueous solution of NaHCO₃ and EtOAc were added. The layers were separated and the aqueous phase was extracted with EtOAc (3 times). The combined organic extracts were dried over MgSO₄, filtered and evaporated in vacuo to give intermediate A4 (850 mg, 94%) as a yellow oil.

B.1.1.2. Synthesis of Intermediate A1

(1S,2S)-2-(4-Bromo-3-fluorophenyl)cyclopropane-1-carboxylic acid $$\underset{A3}{\text{[structure]}} \xrightarrow[\text{THF:H}_2\text{O} \\ \text{rt, 18 h}]{\text{LiOH·H}_2\text{O}} \underset{A1}{\text{[structure]}}$$

Lithium hydroxide monohydrate (833 mg, 19.9 mmol) was added to a solution of intermediate A3 (1.00 g, 3.31 mmol) in THF (10 mL) and H₂O (5 mL). The reaction mixture was stirred at rt for 18 h. The reaction mixture was diluted with brine and EtOAc. The layers were separated and the aqueous phase was extracted with EtOAc (twice). The combined organic extracts were dried over MgSO₄, filtered and evaporated in vacuo to give intermediate A1 (950 mg, quant., 92% purity).

B.1.1.3. Synthesis of Intermediate A2

(1R,2R)-2-(4-Bromo-3-fluorophenyl)cyclopropane-1-carboxylic acid $$\underset{A2\cdot\text{i-PrNH}_2}{\text{[structure]}} \xrightarrow{\text{KHSO}_4 \text{ aq.}}$$

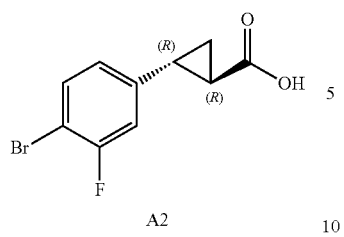

A2

Intermediate A2.i-PrNH$_2$ was washed with a 10% aqueous solution of KHSO$_4$ to afford intermediate A2.

B.1.1.4. Synthesis of Intermediates A8 and A9

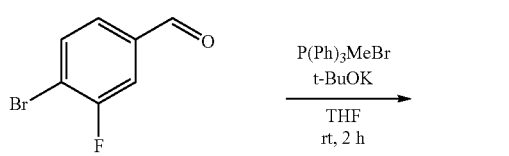

[133059-43-5]

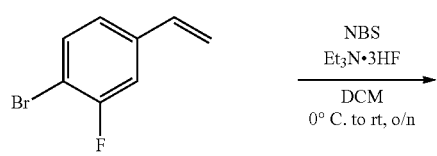

A5

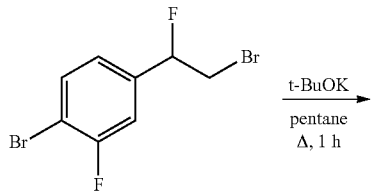

A6

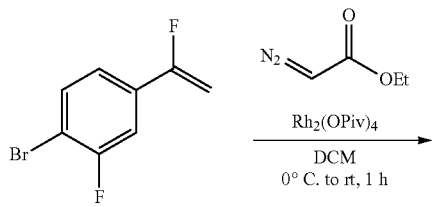

A7

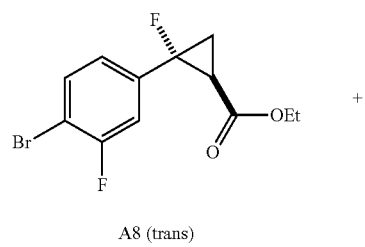

A8 (trans)

+

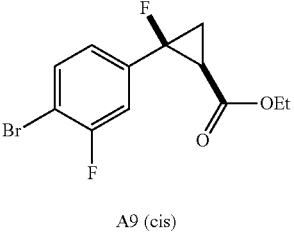

A9 (cis)

Intermediate A5

1-Bromo-4-ethenyl-2-fluorobenzene

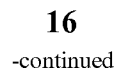

A5

4-Bromo-3-fluorobenzaldehyde [133059-43-5] (1.00 g, 4.93 mmol) was dissolved in anhydrous THF (7 mL) under argon atmosphere. Methyltriphenylphosphonium bromide (1.90 g, 5.32 mmol) and potassium tert-butoxide (608 mg, 5.42 mmol) were added and the reaction mixture was stirred at rt for 2 h. The reaction was quenched by the addition of a saturated aqueous solution of NH$_4$Cl and concentrated under reduced pressure. The aqueous phase was extracted with DCM. The combined organic extracts were washed with water, dried over MgSO$_4$, filtered and evaporated under reduced pressure. The crude mixture was purified by flash column chromatography (silica gel, mobile phase: petroleum ether) to afford intermediate A5 (714 mg, 72%) as a colorless oil.

Intermediate A6

1-Bromo-4-(2-bromo-1-fluoroethyl)-2-fluorobenzene

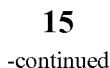

A6

Intermediate A5 (6.39 g, 31.8 mmol) was dissolved in anhydrous DCM (27 mL) and the solution was cooled to 0° C. NBS (6.22 g, 35.0 mmol) was added and a solution of TREAT-HF (7.8 mL, 47.9 mmol) in DCM (16 mL) was added with a syringe pump over 30 min. The reaction mixture was stirred at 0° C. for 15 min and let to warm up to rt. The reaction mixture was stirred overnight. The mixture was poured out into iced water (500 mL) and a 20% aqueous solution of ammonia was added until the pH was slightly basic.

The layers were separated and the aqueous phase was extracted with DCM (4 times). The combined organic extracts were washed with a 0.1N aqueous solution of HCl (twice) and a 5% aqueous solution of NaHCO$_3$ (twice), dried over MgSO$_4$, filtered and evaporated in vacuo. The crude mixture was purified by flash column chromatography (silica gel, mobile phase: pentane) to afford intermediate A6 (3.61 g, 38%) as a colorless oil.

Intermediate A7

1-Bromo-2-fluoro-4-(1-fluoroethenyl)benzene

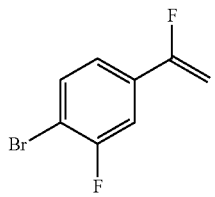

A7

Intermediate A6 (1.17 g, 3.90 mmol) was dissolved in pentane (24 mL). Potassium tert-butoxide (875 mg, 7.80 mmol) was added and the reaction mixture was stirred under reflux for 1 h. The mixture was poured out into an ice/water mixture. The layers were separated and the aqueous phase was extracted with pentane. The combined organic extracts were washed with a 5% aqueous solution of NaHCO$_3$, a 0.05N aqueous solution of HCl and water, dried over MgSO$_4$, filtered and concentrated under reduced pressure. The mixture was filtered over silica gel eluting with pentane to afford intermediate A7 (690 mg, 81%) as a colorless oil.

Intermediates A8 and A9

A8: Ethyl trans-2-(4-bromo-3-fluorophenyl)-2-fluorocyclopropane-1-carboxylate

A9: Ethyl cis-2-(4-bromo-3-fluorophenyl)-2-fluorocyclopropane-1-carboxylate

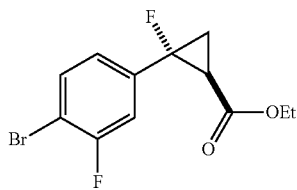

A8 (trans)

A9 (cis)

A solution of intermediate A7 (82.3 mg, 0.38 mmol) in anhydrous DCM (1 mL) and under an argon atmosphere was cooled to 0° C. Rhodium (II) trimethylacetate, dimer (4.50 mg, 7.50 µmol) was added and a solution of ethyl diazoacetate (solution containing 11 wt. % DCM, 65.2 mg, 0.56 mmol) in anhydrous DCM (1 mL) was added with a syringe pump at a rate of 8 mL/h. Once the addition complete, the reaction mixture was stirred for another 1 h. The reaction mixture was cooled to 0° C. and a solution of ethyl diazoacetate (solution containing 11 wt. % DCM, 65.2 mg, 0.56 mmol) in anhydrous DCM (1 mL) was added under the same conditions. Once the addition complete, the reaction mixture was stirred for another 1 h. The reaction mixture was concentrated under reduced pressure. The crude mixture was purified by column chromatography (silica gel, mobile phase gradient: petroleum ether/DCM from 80:20 to 70:30) to give intermediate A8 (57 mg, 50%) and A9 (44 mg, 37%) as colorless oils.

B.1.1.5. Synthesis of Intermediate A10

[(1S,2S)-2-(4-Bromo-3-fluorophenyl)cyclopropyl]methanol

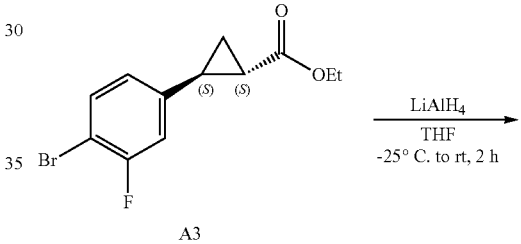

A3

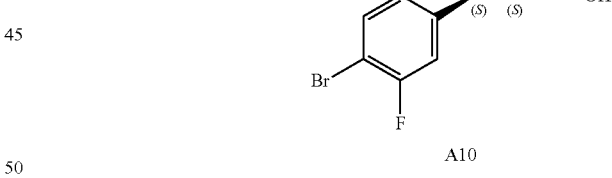

A10

Lithium aluminium hydride (1.0 M in THF, 1.59 mL, 1.59 mmol) was added to a solution of intermediate A3 (400 mg, 1.32 mmol) in anhydrous THF (8 mL) at −25° C. and under nitrogen atmosphere. The reaction mixture was gradually warmed to rt and stirred for 2 h. The reaction mixture was cooled to 0° C. and a 10% aqueous solution of NaOH was carefully added. The resulting mixture was warmed to rt. The layers were separated and the aqueous phase was extracted with DCM. The combined organic extracts were dried over MgSO$_4$, filtered and the solvent was evaporated in vacuo. The crude mixture was purified by preparative LC (irregular SiOH, 15-40 µm, 24 g GraceResolv™, liquid injection (DCM), mobile phase gradient: heptane/EtOAc from 90:10 to 80:20) to give intermediate A10 (167 mg, 51%).

B.1.1.6. Synthesis of Intermediate A12

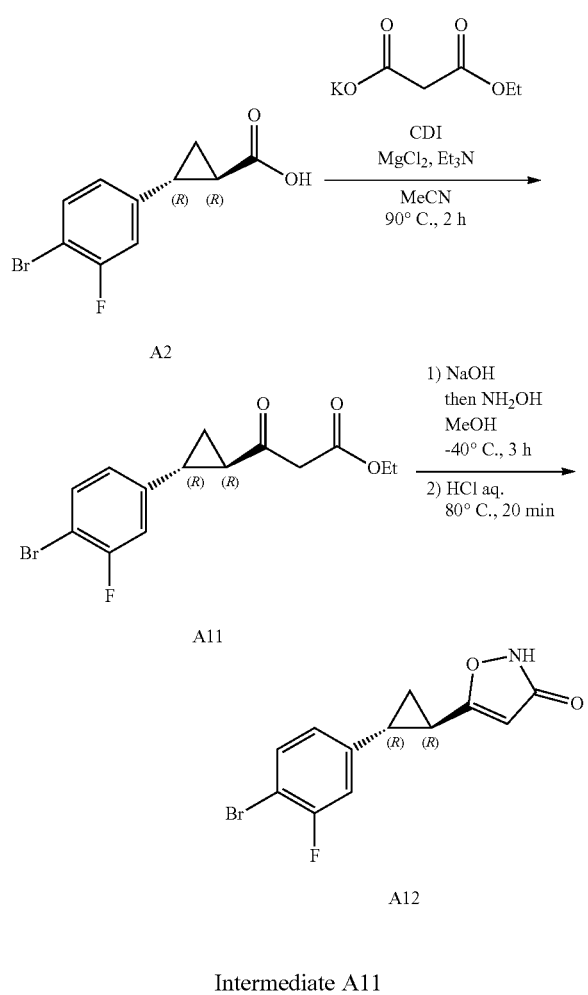

Intermediate A11

Ethyl 3-[(1R,2R)-2-(4-bromo-3-fluorophenyl)cyclopropyl]-3-oxopropanoate

A mixture of intermediate A2 (1.00 g, 3.86 mmol) and CDI (688 mg, 4.25 mmol) in MeCN (10 mL) was stirred at rt for 1 h. This mixture was added to a mixture of ethyl potassium malonate (1.31 g, 7.72 mmol), magnesium chloride (919 mg, 9.65 mmol) and Et$_3$N (1.60 mL, 11.5 mmol) in MeCN (10 mL) that was stirred at rt for 1 h. The resulting reaction mixture was stirred at 90° C. for 2 h. The reaction mixture was diluted with water and EtOAc and filtered over a pad of Celite®. The layers were separated and the aqueous phase was extracted with EtOAc. The combined organic extracts were washed with brine, dried over MgSO$_4$, filtered and evaporated in vacuo. The crude mixture was purified by preparative LC (irregular SiOH, 15-40 μm, 120 g Grace®, liquid injection (DCM), mobile phase gradient: heptane/EtOAc from 100:0 to 70:30) to afford intermediate A11 (1 g, 79%) as a white solid.

Intermediate A12

5-[(1R,2R)-2-(4-Bromo-3-fluorophenyl)cyclopropyl]-2,3-dihydro-1,2-oxazol-3-one

Sodium hydroxide (1.0 M in H$_2$O, 3.10 mL, 3.10 mmol) was added slowly to a solution of intermediate A11 (1.00 g, 3.04 mmol) in MeOH (28 mL) at −40° C. The reaction mixture was stirred at this temperature for 20 min. Hydroxylamine (50 wt. % in H$_2$O, 186 μL, 3.04 mmol) was added slowly and the reaction mixture was stirred at −40° C. for 3 h. Hydrochloric acid (37% in H$_2$O, 7.60 mL, 91.1 mmol) was added and the reaction mixture was stirred at 80° C. for 20 min. The solvent (MeOH) was evaporated in vacuo and the residue was diluted with DCM and water. The layers were separated and the aqueous phase was extracted. The combined organic extracts were dried over MgSO$_4$, filtered and concentrated under reduced pressure. The crude mixture was purified by preparative LC (irregular SiOH, 15-40 μm, 120 g Grace®, liquid injection (DCM), mobile phase gradient: heptane/EtOAc from 100:0 to 30:70) to give intermediate A12 (272 mg, 30%) as a white solid.

B.1.1.7. Synthesis of Intermediate A14

Method A

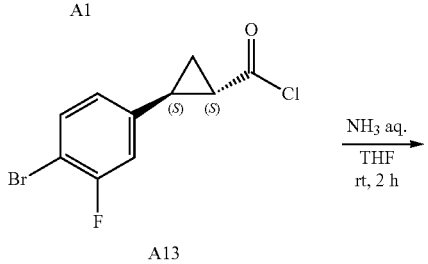

-continued

Intermediate A13

(1S,2S)-2-(4-Bromo-3-fluorophenyl)cyclopropane-1-carbonyl chloride

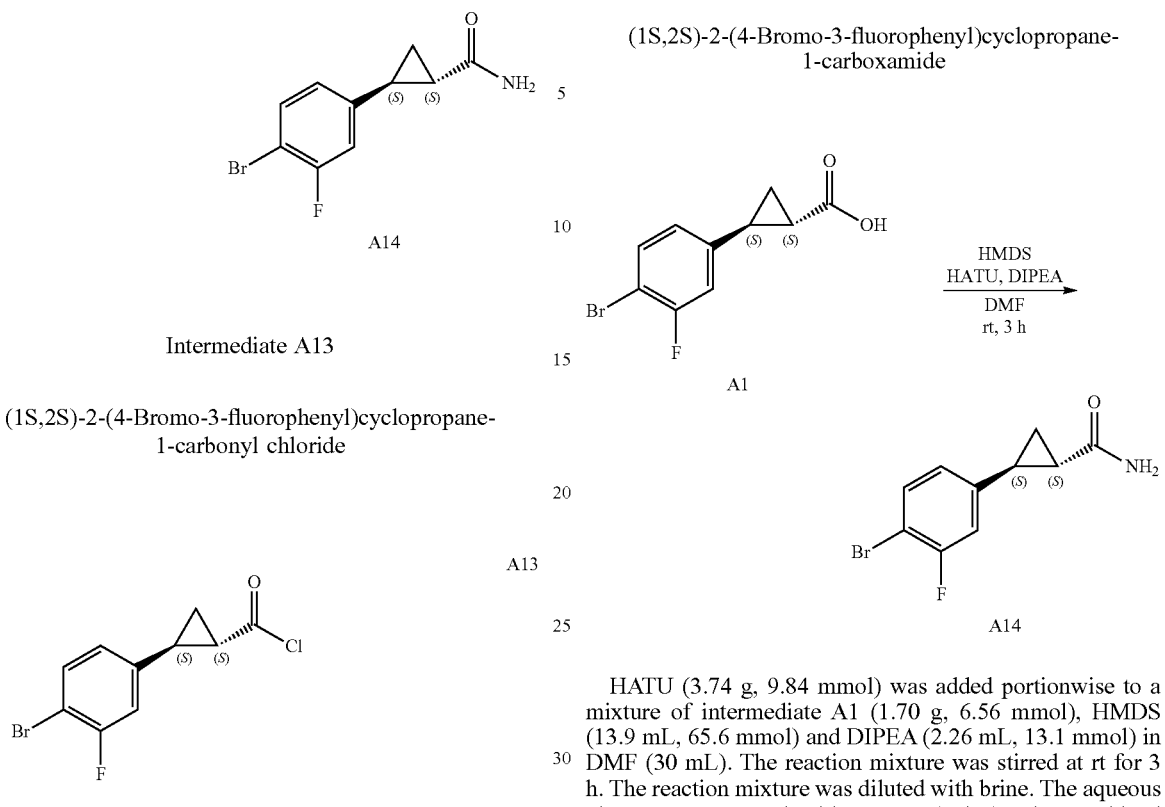

Thionyl chloride (0.27 mL, 3.71 mmol) was added to a solution of intermediate A1 (533 mg, 1.85 mmol, 90% purity) in DCM (18 mL). The reaction mixture was stirred at rt for 90 min. The mixture was evaporated in vacuo to afford intermediate A13 (514 mg, quant.).

Intermediate A14

(1S,2S)-2-(4-Bromo-3-fluorophenyl)cyclopropane-1-carboxamide

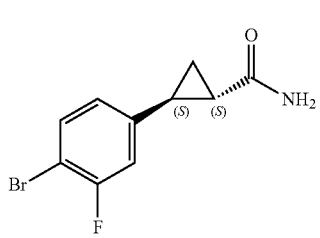

Ammonia (28% in H$_2$O, 18.0 mL, 266 mmol) was added to a solution of intermediate A13 (514 mg, 1.85 mmol) in THF (18 mL). The reaction mixture was stirred at rt for 2 h. Brine, a 3.0 M aqueous solution of NaOH and EtOAc were added. The layers were separated and the aqueous phase was extracted with EtOAc (twice). The combined organic extracts were dried over MgSO$_4$, filtered and evaporated in vacuo to afford intermediate A14 (440 mg, 74%, 80% purity).

Method B (1S,2S)-2-(4-Bromo-3-fluorophenyl)cyclopropane-1-carboxamide

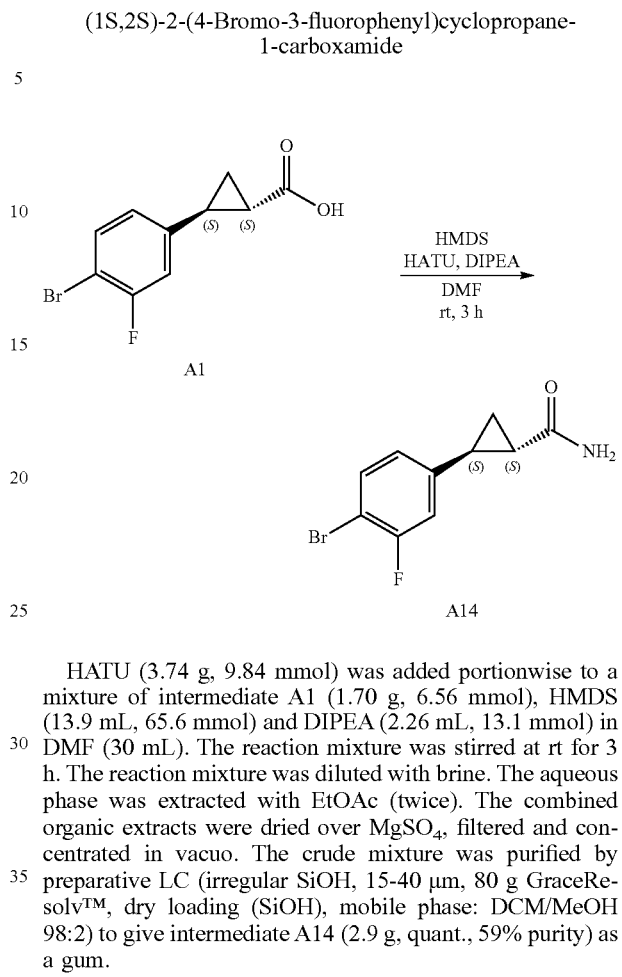

HATU (3.74 g, 9.84 mmol) was added portionwise to a mixture of intermediate A1 (1.70 g, 6.56 mmol), HMDS (13.9 mL, 65.6 mmol) and DIPEA (2.26 mL, 13.1 mmol) in DMF (30 mL). The reaction mixture was stirred at rt for 3 h. The reaction mixture was diluted with brine. The aqueous phase was extracted with EtOAc (twice). The combined organic extracts were dried over MgSO$_4$, filtered and concentrated in vacuo. The crude mixture was purified by preparative LC (irregular SiOH, 15-40 μm, 80 g GraceResolv™, dry loading (SiOH), mobile phase: DCM/MeOH 98:2) to give intermediate A14 (2.9 g, quant., 59% purity) as a gum.

B. 1.1.8. Synthesis of Intermediate A15

(1S,2S)-2-(4-Bromo-3-fluorophenyl)cyclopropane-1-carbonitrile

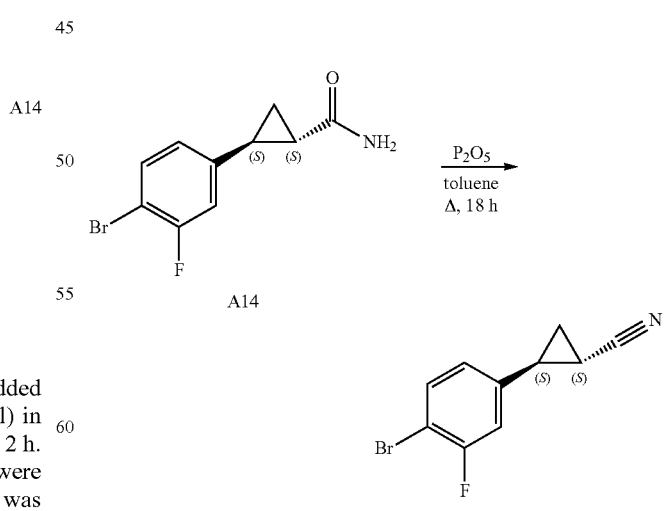

A sealed tube was charged with intermediate A14 (440 mg, 1.36 mmol, 80% purity), anhydrous toluene (13 mL)

and phosphorous pentoxide (0.97 g, 6.82 mmol). The reaction mixture was stirred under reflux for 18 h. The reaction was quenched by the addition of a saturated aqueous solution of NaHCO₃, diluted with EtOAc and filtered. The layers were separated and the aqueous phase was extracted with a solution of EtOAc and MeOH (9:1) (twice). The combined organic extracts were dried over MgSO₄, filtered and evaporated in vacuo. The crude mixture was purified by preparative LC (irregular SiOH, 15-40 μm, 24 g GraceResolv™, dry loading (SiOH), mobile phase gradient: heptane/EtOAc from 90:10 to 70:30) to give intermediate A15 (185 mg, 55%).

B.1.1.9. Synthesis of Intermediate A18

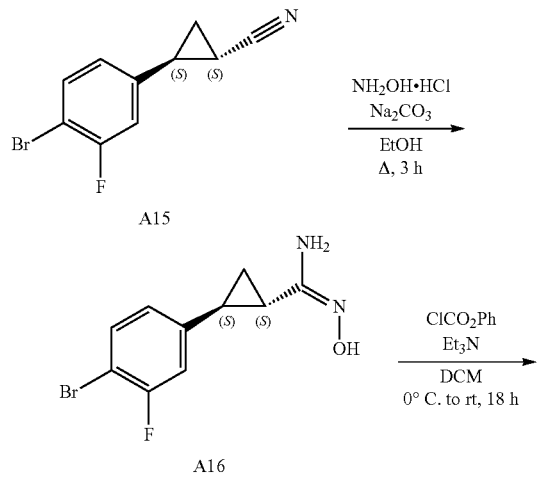

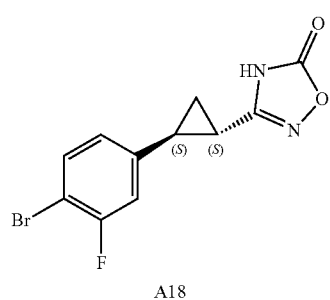

Intermediate A16

(E)-(1S,2S)-2-(4-Bromo-3-fluorophenyl)-N'-hydroxycycloprop-1-carboximidamide

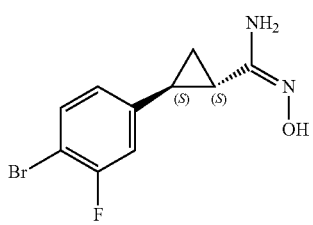

Hydroxylamine hydrochloride (261 mg, 3.75 mmol) was added to a suspension of intermediate A15 (300 mg, 1.25 mmol) and sodium carbonate (530 mg, 5.00 mmol) in EtOH (15 mL). The reaction mixture was stirred under reflux for 3 h. The mixture was evaporated in vacuo. The residue was diluted with water and DCM. The layers were separated and the aqueous phase was extracted with DCM (twice). The combined organic extracts were dried over MgSO₄, filtered and evaporated in vacuo to afford intermediate A16 (332 mg, 97%).

Intermediate A11

(E)-{Amino[(1S,2S)-2-(4-bromo-3-fluorophenyl)cyclopropyl]methylidene}amino phenyl carbonate

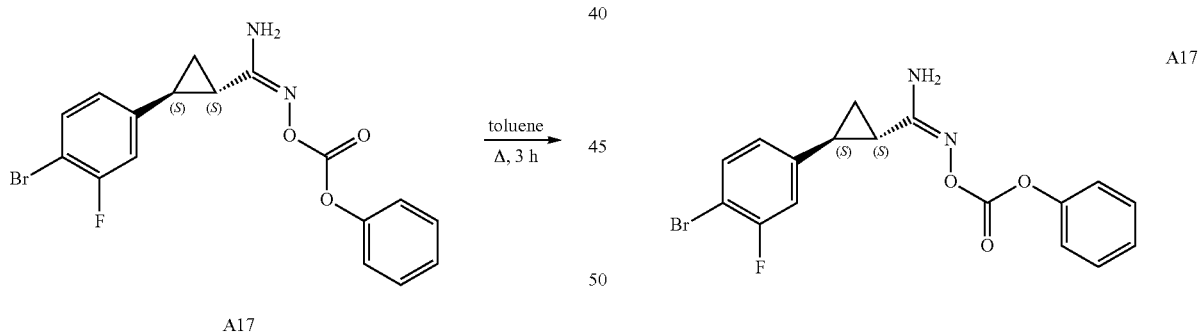

Phenyl chloroformate (228 μL, 1.82 mmol) was added to a mixture of intermediate A16 (332 mg, 1.22 mmol) and Et₃N (507 μL, 3.65 mmol) in DCM (15 mL) at 0° C. The reaction mixture was stirred at rt for 18 h. The reaction mixture was diluted with water and DCM. The layers were separated and the aqueous phase was extracted with DCM (twice). The combined organic extracts were dried over MgSO₄, filtered and evaporated in vacuo. The crude mixture was purified by preparative LC (irregular SiOH, 15-40 μm, 40 g GraceResolv™, liquid injection (DCM), mobile phase gradient: heptane/EtOAc from 90:10 to 70:30) to afford intermediate A17 (347 mg, 73%).

Intermediate A18

3-[(1S,2S)-2-(4-Bromo-3-fluorophenyl)cyclopropyl]-4,5-dihydro-1,2,4-oxadiazol-5-one

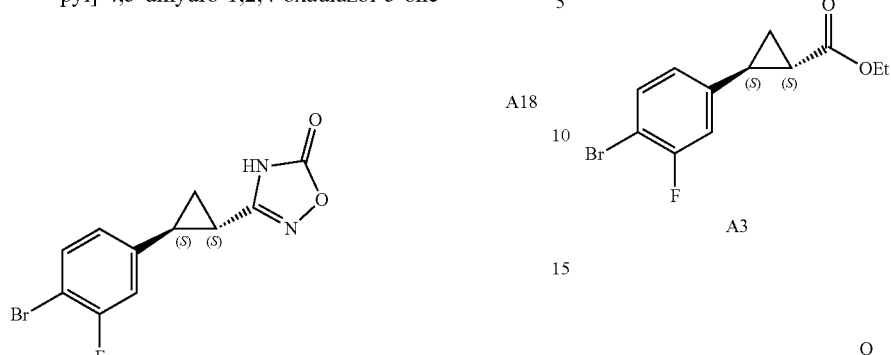

In a sealed tube a solution of intermediate A17 (347 mg, 0.88 mmol) in anhydrous toluene (10 mL) was stirred under reflux for 3 h. The mixture was evaporated in vacuo. The residue was diluted with DCM. The precipitate was filtered off and dried under vacuum to give intermediate A18 (140 mg, 53%) as a white solid.

B.1.1.10. Synthesis of Intermediate A19

(1S,2S)-2-(4-Bromo-3-fluorophenyl)-N-methylcyclopropane-1-carboxamide

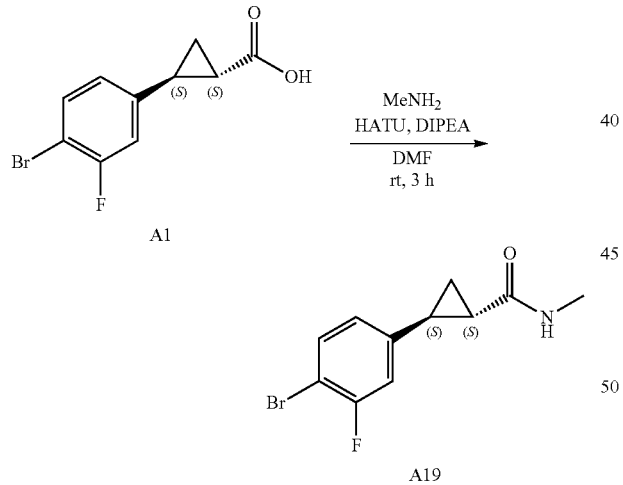

HATU (1.89 g, 4.98 mmol) was added portionwise to a mixture of intermediate A1 (860 mg, 3.32 mmol), methylamine (2.0 M in THF, 16.6 mL, 33.2 mmol) and DIPEA (1.14 mL, 6.64 mmol) in DMF (15 mL). The reaction mixture was stirred at rt for 3 h. Brine was added and the aqueous phase was extracted with EtOAc (twice). The combined organic extracts were dried over MgSO$_4$, filtered and concentrated under reduced pressure. The crude mixture was purified by preparative LC (irregular SiOH, 15-40 µm, 80 g GraceResolv™, dry loading (SiOH), mobile phase: DCM/MeOH 98:2) to give intermediate A19 (1.00 g, quant., 90% purity) as a white solid.

B. 1.1.11. Synthesis of Intermediate A23

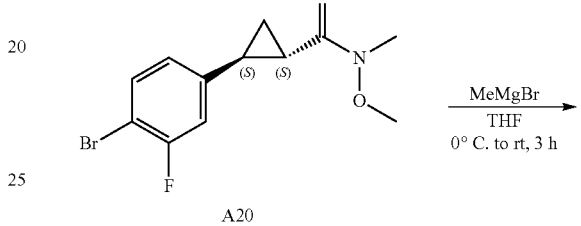

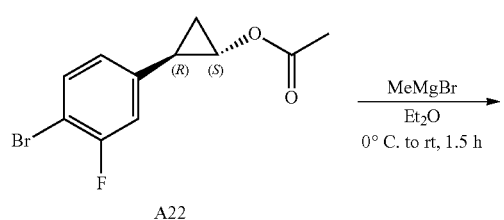

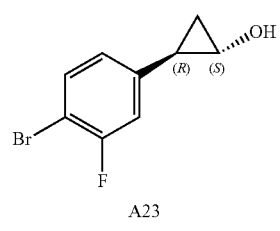

Intermediate A20

(1S,2S)-2-(4-Bromo-3-fluorophenyl)-N-methoxy-N-methylcyclopropane-1-carboxamide

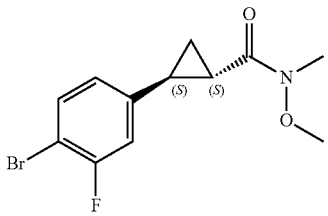

Under nitrogen atmosphere a mixture of intermediate A3 (60 mg, 0.20 mmol) and N,O-dimethylhydroxylamine hydrochloride (58.1 mg, 0.60 mmol) was stirred at −30° C. Isopropylmagnesium chloride (2.0 M in THF, 0.60 mL, 1.20 mmol) was added. The reaction mixture was stirred at −30° C. for 1 h. The reaction was quenched by the addition of a 1N aqueous solution of HCl and diluted with EtOAc. The layers were separated and the aqueous phase was extracted with EtOAc. The combined organic extracts were washed with brine, dried over MgSO$_4$, filtered and evaporated in vacuo to afford intermediate A20 (58 mg, 97%) as a colorless oil.

Intermediate A21

1-[(1S,2S)-2-(4-Bromo-3-fluorophenyl)cyclopropyl]ethan-1-one

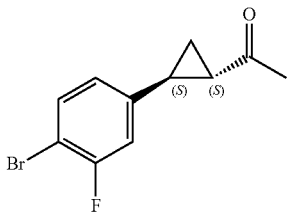

Under nitrogen atmosphere methylmagnesium bromide (3.0 M in Et$_2$O, 6.62 mL, 19.9 mmol) was added to a solution of intermediate A20 (3.00 g, 9.93 mmol) in THF (12 mL) at 0° C. The reaction mixture was stirred at rt for 3 h. The reaction was quenched by the addition of an aqueous solution of NH$_4$Cl and diluted with EtOAc. The layers were separated and the aqueous phase was extracted with EtOAc. The combined organic extracts were washed with brine, dried over MgSO$_4$, filtered and evaporated in vacuo to afford intermediate A21 (2.55 g, quant.) as a colorless oil.

Intermediate A22

(1S,2R)-2-(4-Bromo-3-fluorophenyl)cyclopropyl acetate

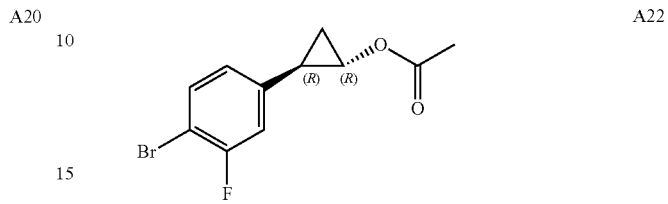

Trifluoroacetic anhydride (5.31 mL, 38.2 mmol) was added dropwise to a mixture of intermediate A21 (2.55 g, 9.92 mmol) and carbamide peroxide [124-43-6] (3.59 g, 38.2 mmol) in EtOAc (27 mL) at 0° C. The reaction mixture was stirred at rt for 18 h. The reaction was quenched by the addition of an aqueous solution of NaHCO$_3$. The layers were separated and the organic phase was washed with an aqueous solution of NaHCO$_3$ and brine, dried over Na$_2$SO$_4$, filtered and concentrated under reduced pressure. The crude mixture was purified by preparative LC (irregular SiOH, 15-40 μm, 80 g GraceResolv™, liquid injection (DCM), mobile phase gradient: heptane/EtOAc from 99:1 to 60:40) to afford intermediate A22 (1.83 g, 67%).

Intermediate A23

(1S,2R)-2-(4-Bromo-3-fluorophenyl)cyclopropan-1-ol

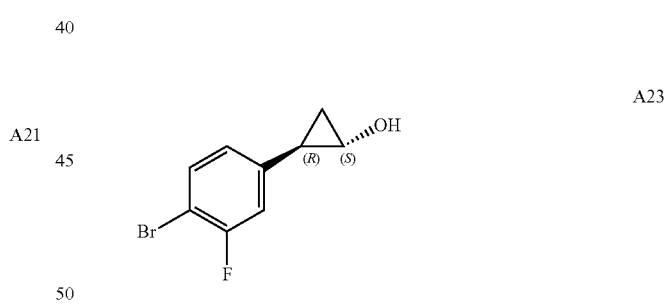

Methylmagnesium bromide (3.0 M in Et$_2$O, 2.44 mL, 7.32 mmol) was added dropwise to a solution of intermediate A22 (1.00 g, 3.66 mmol) in Et$_2$O (20 mL) at 0° C. The reaction mixture was stirred at rt for 1.5 h. The reaction was quenched by the dropwise addition of a 10% aqueous solution of NH$_4$Cl. The layers were separated and the aqueous phase was extracted with EtOAc (3 times). The combined organic extracts were washed with brine, dried over Na$_2$SO$_4$, filtered and concentrated under reduced pressure. The crude mixture was purified by preparative LC (irregular SiOH, 15-40 μm, 24 g GraceResolv™, liquid injection, mobile phase gradient: heptane/EtOAc from 99:1 to 50:50) to give intermediate A23 (600 mg, 71%).

B.1.1.12. Synthesis of Intermediates A24, A25 and A26

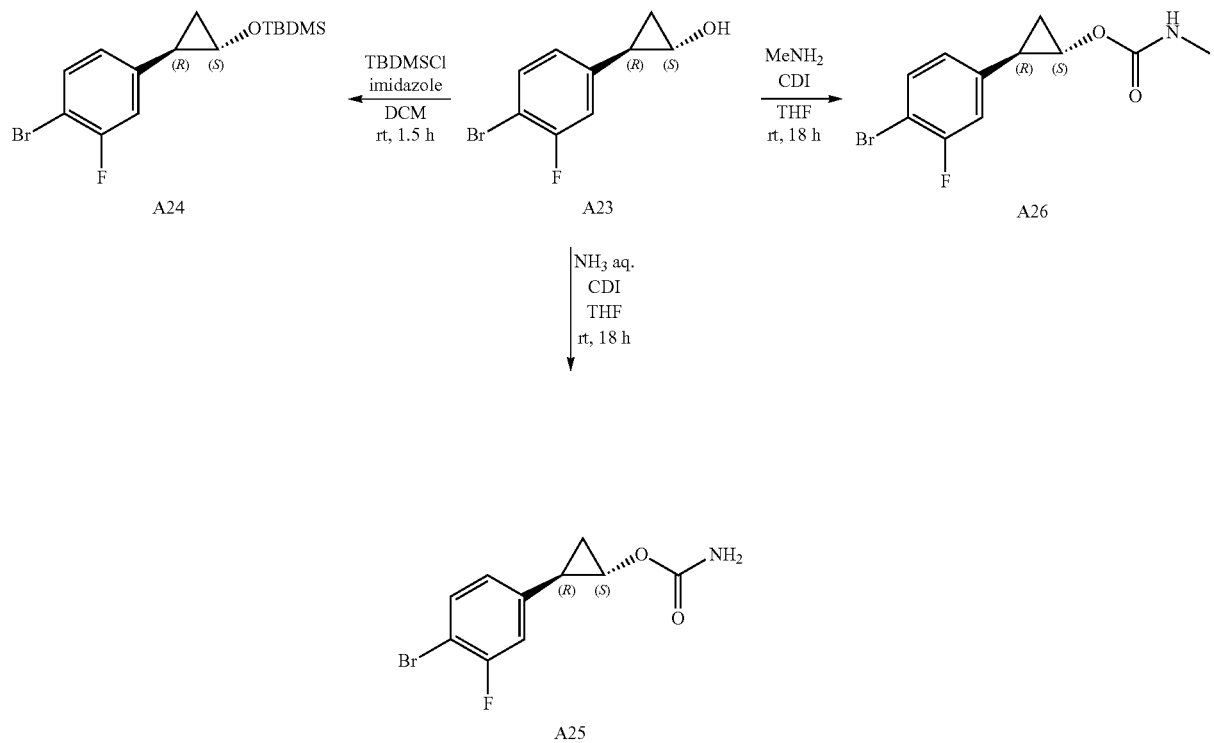

Intermediate A24

[(1S,2R)-2-(4-Bromo-3-fluorophenyl)cyclopropoxy](tert-butyl)dimethylsilane

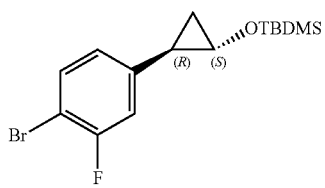

A24

Tert-butyldimethylsilyl chloride (73.1 mg, 0.49 mmol) and imidazole (51.9 mg, 0.76 mmol) were added to a solution of intermediate A23 (80.0 mg, 0.35 mmol) in DCM (4.3 mL) under nitrogen atmosphere. The reaction mixture was stirred at rt for 1.5 h. The reaction mixture was diluted with DCM and water. The layers were separated and the aqueous phase was extracted with DCM (twice). The combined organic extracts were dried over MgSO$_4$, filtered and concentrated under reduced pressure to afford intermediate A24 (120 mg, quant.).

Intermediate A25

(1S,2R)-2-(4-Bromo-3-fluorophenyl)cyclopropyl carbamate

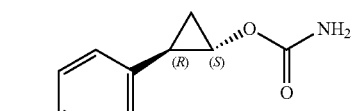

In a sealed tube CDI (140 mg, 0.87 mmol) was added to a solution of intermediate A23 (100 mg, 433 µmol) in anhydrous THF (1.6 mL). The reaction mixture was stirred at rt for 1 h. Ammonia (28% in H$_2$O, 1.6 mL, 23.9 mmol) was added and the reaction mixture was stirred at rt for 18 h. The reaction mixture was diluted with water, brine and EtOAc. The layers were separated and the aqueous phase was extracted with EtOAc (twice). The combined organic extracts were dried over MgSO$_4$, filtered and concentrated under reduced pressure. The crude mixture was purified by preparative LC (irregular SiOH, 15-40 µm, 12 g GraceResolv™, liquid injection (DCM), mobile phase gradient: heptane/EtOAc from 99:1 to 50:50) to give intermediate A25 (78 mg, 66%).

Intermediate A26

(1S,2R)-2-(4-Bromo-3-fluorophenyl)cyclopropyl N-methylcarbamate

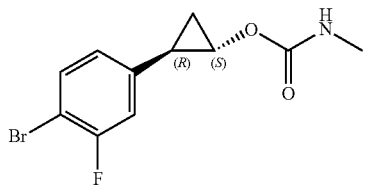

In a sealed tube CDI (140 mg, 0.87 mmol) was added to a solution of intermediate A23 (100 mg, 0.43 mmol) in anhydrous THF (1.6 mL). The reaction mixture was stirred at rt for 1 h. Methylamine (2.0 M in THF, 1.10 mL, 2.20 mmol) was added and the reaction mixture was stirred at rt for 18 h. The reaction mixture was diluted with water, brine and EtOAc. The layers were separated and the aqueous phase was extracted with EtOAc (twice). The combined organic extracts were dried over MgSO$_4$, filtered and concentrated under reduced pressure. The crude mixture was purified by preparative LC (irregular SiOH, 15-40 µm, 12 g GraceResolv™, liquid injection (DCM), mobile phase gradient: heptane/EtOAc from 99:1 to 50:50) to afford intermediate A26 (115 mg, 92%).

B.1.1.13. Synthesis of Intermediate A30

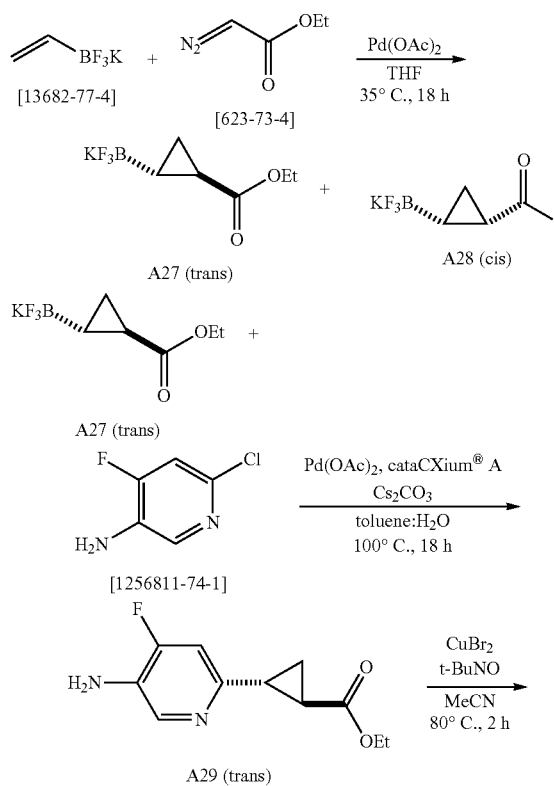

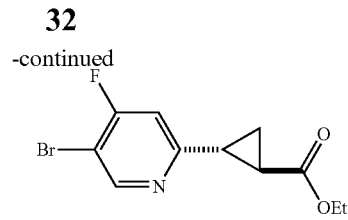

Intermediates A27 et A28

A27: Ethyl trans 2-(trifluoro-λ$^4$-boranyl)cyclopropane-1-carboxylate potassium A28: Ethyl cis 2-(trifluoro-λ$^4$-boranyl)cyclopropane-1-carboxylate potassium

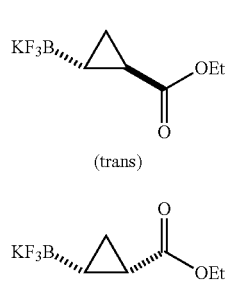

Potassium vinyltrifluoroborate [13682-77-4] (2.00 g, 14.9 mmol) was solubilized in THF (20.5 mL). Palladium acetate (33.5 mg, 149 µmol) was added. The mixture was stirred at 35° C. and a solution of ethyl diazoacetate [623-73-4] (2.0 mL, 16.4 mmol) in THF (2 mL) was added with a syringe pump over 4 h. The reaction mixture was stirred at 35° C. for 18 h. The reaction mixture was cooled to rt and diluted with heptane. The mixture was stirred for 30 min and filtered. The gum was crystallized from acetone (20 mL) at −18° C. and the solid was filtered off to afford intermediate A28 (cis:trans 80:20) (520 mg, 16%) as a grey solid. The filtrate was treated with activated charcoal, filtered and concentrated to dryness. The product was taken-up in EtOH (20 mL) at 50° C. and the gummy product was filtered to afford intermediate A27 (cis:trans 14:86) (1.83 g, 56%) as a white solid.

Intermediate A29

Ethyl trans-2-(5-amino-4-fluoropyridin-2-yl)cyclopropane-1-carboxylate

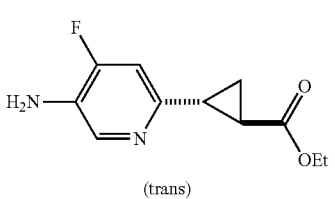

To a mixture of cataCXium® A (147 mg, 409 µmol), intermediate A27 (751 mg, 3.41 mmol), 6-chloro-4-fluoropyridin-3-amine [1256811-74-1] (250 mg, 1.71 mmol) and palladium acetate (61.3 mg, 273 µmol) in toluene (19 mL) and H₂O (1.9 mL) under a nitrogen atmosphere was added cesium carbonate (1.67 g, 5.12 mmol). The reaction mixture was stirred at 100° C. for 18 h. The reaction mixture was diluted with water and EtOAc. The layers were separated and the aqueous phase was extracted with EtOAc (twice). The combined organic extracts were dried over MgSO₄, filtered and the solvent was evaporated in vacuo. The crude mixture was purified by preparative LC (irregular SiOH, 15-40 µm, 24 g Grace®, liquid injection (DCM), mobile phase gradient: heptane/EtOAc from 100:0 to 20:80) to afford intermediate A29 (77 mg, 20%).

Intermediate A30

Ethyl trans-2-(5-bromo-4-fluoropyridin-2-yl)cyclopropane-1-carboxylate

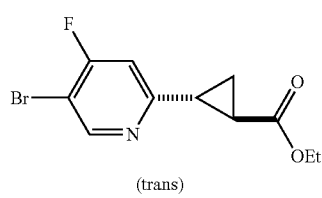

(trans)

A30

A mixture of intermediate A29 (103 mg, 459 µmol), copper(II) bromide (123 mg, 0.55 mmol) and tert-butyl nitrite (82.0 µL, 689 µmol) in MeCN (6 mL) was stirred at 80° C. for 2 h. The reaction mixture was diluted with water and EtOAc. The layers were separated and the aqueous phase was extracted with EtOAc. The combined organic extracts were dried over MgSO₄, filtered and the solvent was evaporated in vacuo. The crude mixture was purified by preparative LC (irregular SiOH, 15-40 µm, 12 g Grace®, liquid injection (DCM), mobile phase gradient: heptane/EtOAc from 100:0 to 50:50) to afford intermediate A30 (84 mg, 63%).

B.1.1.14. Synthesis of Intermediate A33

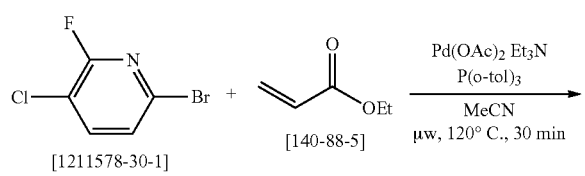

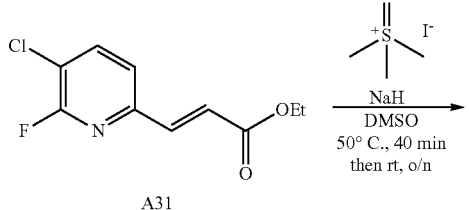

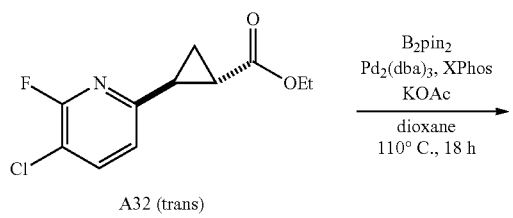

A32 (trans)

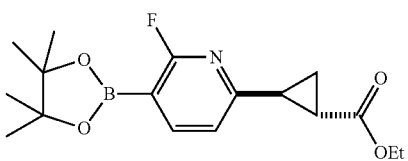

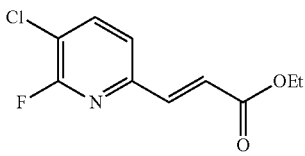

A33 (trans)

Intermediate A31

Ethyl (2E)-3-(5-chloro-6-fluoropyridin-2-yl)prop-2-enoate

A31

The reaction was performed on two batches of 500 mg of 6-bromo-3-chloro-2-fluoropyridine [1211578-30-1] that were combined for treatment and purification. A mixture of 6-bromo-3-chloro-2-fluoropyridine [1211578-30-1] (500 mg, 2.38 mmol), ethyl acrylate [140-88-5] (1.55 mL, 14.3 mmol), palladium acetate (53.3 mg, 0.24 mmol), tri(o-tolyl)phosphine (145 mg, 475 µmol) and Et₃N (2.0 mL, 14.3 mmol) in MeCN (8.4 mL) was heated at 120° C. using a single mode microwave (Biotage® Initiator EXP 60) with a power output ranging from 0 to 400 W for 30 min. The two batches were combined and the solvent was evaporated to dryness. The crude mixture was purified by preparative LC (irregular SiOH, 15-40 µm, 40 g GraceResolv™, dry loading (Celite®), mobile phase gradient: heptane/EtOAc from 100:0 to 80:20) to afford intermediate A31 (972 mg, 89%) as a white solid.

Intermediate A32

Ethyl trans 2-(5-chloro-6-fluoropyridin-2-yl)cyclopropane-1-carboxylate

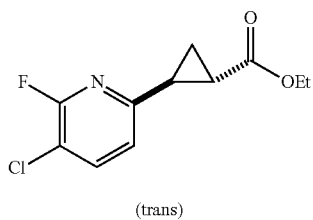

(trans)

Under nitrogen atmosphere sodium hydride (60% dispersion in oil, 111 mg, 2.78 mmol) was charged at rt in a round bottom flask. DMSO (10 mL) was added. Trimethylsulfoxonium iodide (706 mg, 3.21 mmol) was added portionwise. The resulting mixture was stirred at 50° C. for 40 min and cooled to rt. A solution of intermediate A31 (491 mg, 2.14 mmol) in DMSO (7 mL) was added over 30 sec. The reaction mixture was stirred at rt overnight. The reaction was quenched by the dropwise addition of water. The mixture was cooled. Brine, a 1N aqueous solution of HCl and EtOAc were added. The aqueous phase was extracted with EtOAc (twice). The combined organic extracts were washed with brine, dried over MgSO$_4$, filtered and evaporated in vacuo. The crude mixture was purified by preparative LC (irregular SiOH, 15-40 μm, 24 g GraceResolv™, dry loading (Celite®), mobile phase gradient: heptane/EtOAc from 100:0 to 90:10). The residue (232 mg) was purified by reverse phase (spherical C18, 25 μm, 40 g YMC-ODS-25, liquid injection (MeCN), mobile phase gradient: (0.2% aq. NH$_4$HCO$_3$)/MeCN from 40:60 to 10:90) to afford 143 mg. The residue was purified by achiral SFC (Stationary phase: Whelk-O1 (S,S) 5 μm 250*21.2 mm, Mobile phase: 96% CO$_2$, 4% MeOH) to give intermediate A32 (91 mg, 17%) as a white solid.

Intermediate A33

Ethyl trans 2-[6-fluoro-5-(tetramethyl-1,3,2-dioxaborolan-2-yl)pyridine-2-yl]cyclopropane-1-carboxylate

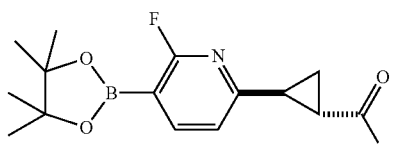

(trans)

In a sealed tube a mixture of intermediate A32 (66.0 mg, 271 μmol), bis(pinacolato)diboron (138 mg, 542 μmol) and potassium acetate (53.2 mg, 542 μmol) in 1,4-dioxane (2.7 mL) was purged with nitrogen. Tris(dibenzylideneacetone)dipalladium(0) (24.8 mg, 27.1 μmol) and XPhos (38.7 mg, 81.3 μmol) were added and the mixture was purged with nitrogen. The reaction mixture was stirred at 110° C. for 18 h. The reaction mixture was diluted with EtOAc and water. The layers were separated and the aqueous phase was extracted with EtOAc (twice). The combined organic extracts were washed with brine, dried over MgSO$_4$, filtered and concentrated in vacuo to afford intermediate A33 (91 mg, quant.) as a brown oil.

B.1.2. Synthesis of Final Compounds

Compound 1

[(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]methanol

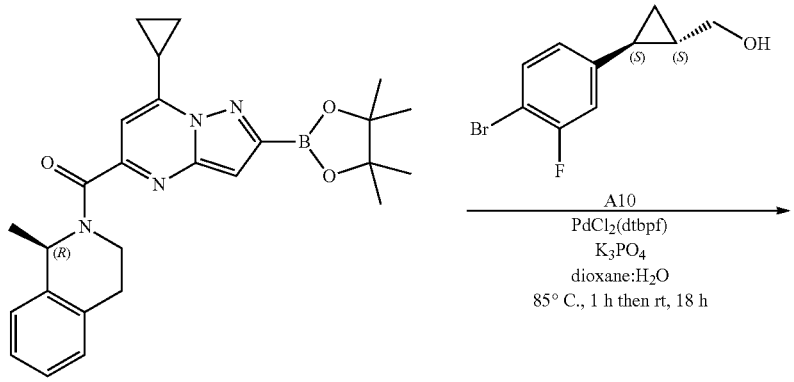

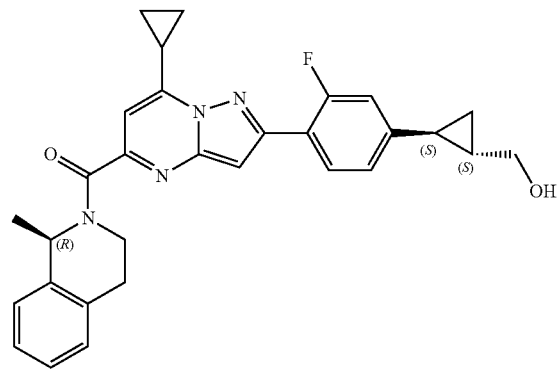

1

A sealed tube was charged with (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (458 mg, 0.62 mmol, 62% purity), intermediate A10 (167 mg, 0.68 mmol), potassium phosphate tribasic (394 mg, 1.86 mmol), 1,4-dioxane (10 mL) and H₂O (2 mL) and purged with nitrogen for 10 min. [1,1′-Bis(di-tert-butylphosphino)ferrocene]dichloro-palladium(II) (40.4 mg, 61.9 µmol) was added and the mixture was purged again with nitrogen for 1 min. The reaction mixture was stirred at 85° C. for 1 h and at rt for 18 h. The reaction mixture was filtered over a pad of Celite®, rinsed with EtOAc and brine was added to the filtrate. The layers were separated and the aqueous phase was extracted with EtOAc (twice). The combined organic extracts were washed with a solution of water and brine (1:9) (twice), dried over MgSO₄, filtered and concentrated under reduced pressure. The crude mixture was purified by preparative LC (irregular SiOH, 15-40 µm, 24 g GraceResolv™, liquid injection (DCM), mobile phase gradient: DCM/MeOH from 100:0 to 98:2). The residue was co-evaporated with EtOH (4 times) and dried under high vacuum at 50° C. for 18 h to give compound 1 (120 mg, 39%) as an off-white solid.

Compound 2

5-[(1R,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]-2,3-dihydro-1,2-oxazol-3-one

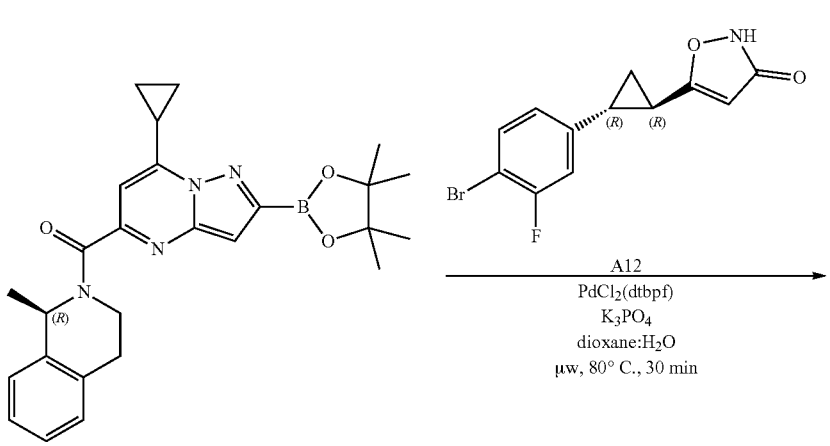

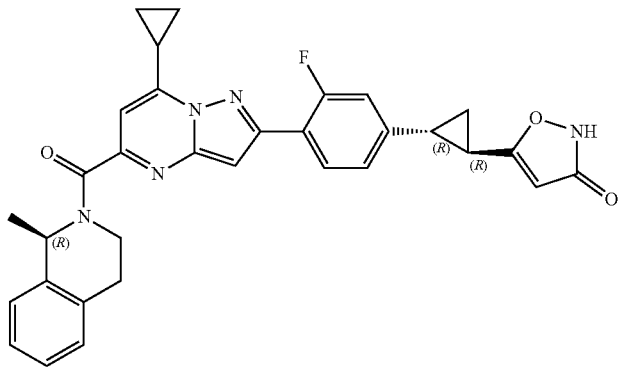

2

The reaction was performed on two batches of 136 mg.

A sealed tube was charged with a solution of intermediate A12 (136 mg, 0.46 mmol) in 1,4-dioxane (8.5 mL). (1R)-2-[7-Cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (209 mg, 239 μmol, 52% purity), H$_2$O (2 mL) and potassium phosphate tribasic (329 mg, 1.55 mmol) were added and the mixture was purged with nitrogen. [1,1'-Bis(di-tert-butylphosphino)ferrocene]dichloropalladium(II) (32.7 mg, 50.0 μmol) was added and the mixture was purged again with nitrogen. The reaction mixture was heated at 80° C. using a single mode microwave (Biotage® Initiator EXP 60) with a power output ranging from 0 to 400 W for 30 min. The two batches were combined. EtOAc and a 10% aqueous solution of KHSO$_4$ were added. The layers were separated and the organic phase was washed with water and brine, dried over MgSO$_4$, filtered and concentrated under reduced pressure. The crude mixture was purified by preparative LC (spherical C18 25 μm, 120 g YMC-ODS-25, dry loading, mobile phase gradient: (0.2% aq. NH$_4$HCO$_3$)/MeCN from 65:35 to 25:75). The fractions containing the product were combined and a 10% aqueous solution of KHSO$_4$ and EtOAc were added. The layers were separated and the organic phase was washed with brine, dried over MgSO$_4$, filtered and concentrated under reduced pressure to give compound 2 (97 mg, 74%) as a grey solid.

Compound 3

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropane-1-carbonitrile

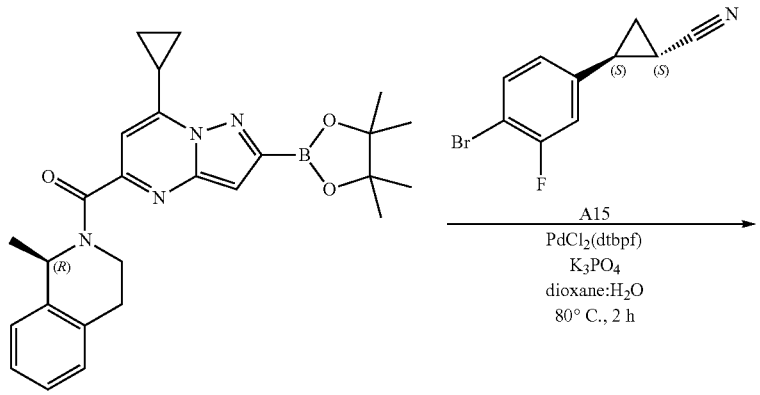

[2035421-36-2]

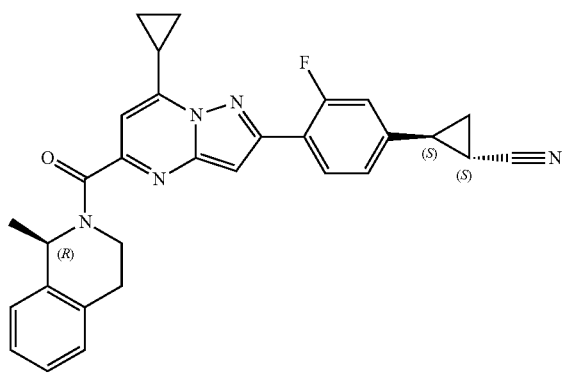

3

A sealed tube was charged with (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (298 mg, 487 µmol, 75% purity), intermediate A15 (120 mg, 487 µmol, 97% purity), potassium phosphate tribasic (310 mg, 1.46 mmol), 1,4-dioxane (5 mL) and H₂O (1 mL) and purged with nitrogen. [1,1'-Bis(di-tert-butylphosphino)ferrocene]dichloropalladium(II) (31.8 mg, 0.49 mmol) was added and the mixture was purged again with nitrogen. The reaction mixture was stirred at 80° C. for 2 h. The reaction mixture was filtered over a pad of Celite®. The filtrate was diluted with EtOAc and brine. The layers were separated and the aqueous phase was extracted with EtOAc (twice). The combined organic extracts were dried over MgSO₄, filtered and concentrated under reduced pressure. The crude mixture was purified by preparative LC (irregular SiOH, 15-40 µm, 24 g GraceResolv™, liquid injection (DCM), mobile phase gradient: heptane/EtOAc from 90:10 to 60:40). The residue was co-evaporated with EtOH (twice) and dried under high vacuum at 50° C. for 18 h to give compound 3 (225 mg, 94%).

Compound 4

(1R)-2-(7-Cyclopropyl-2-{2-fluoro-4-[(1S,2S)-2-(1H-1,2,3,4-tetrazol-5-yl)cyclopropyl]phenyl}pyrazolo[1,5-a]pyrimidine-5-carbonyl)-1-methyl-1,2,3,4-tetrahydroisoquinoline

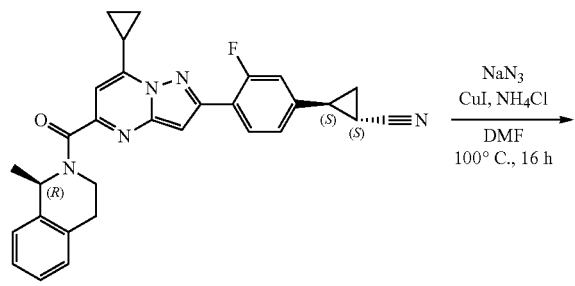

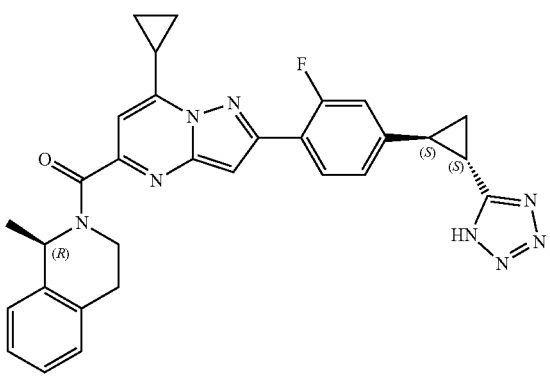

4

In a sealed tube sodium azide (205 mg, 3.15 mmol) was added to a mixture of compound 3 (155 mg, 315 µmol), copper iodide (90.1 mg, 0.47 mmol) and ammonium chloride (50.6 mg, 0.95 mmol) in DMF (5 mL). The reaction mixture was stirred at 100° C. for 16 h. EtOAc, 1N aqueous solution of HCl and brine were added. The layers were separated and the aqueous phase was extracted with EtOAc (3 times). The combined organic extracts were dried over MgSO₄, filtered and the solvent was evaporated in vacuo. The crude mixture was purified by preparative LC (irregular SiOH, 15-40 µm, 24 g GraceResolv™, dry loading (SiOH), mobile phase gradient: DCM/MeOH from 100:0 to 93:7). The residue was dissolved in DCM and MeOH (95:5). The organic phase was washed with water (twice), dried over MgSO₄, filtered and the solvent was evaporated in vacuo. The residue was co-evaporated with EtOH (4 times) and triturated in EtOH. The solid was filtered off, rinsed with EtOH and dried under high vacuum at 50° C. for 18 h to give compound 4 (110 mg, 65%) as a white solid.

Compound 5

3-[(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]-4,5-dihydro-1,2,4-oxadiazol-5-one

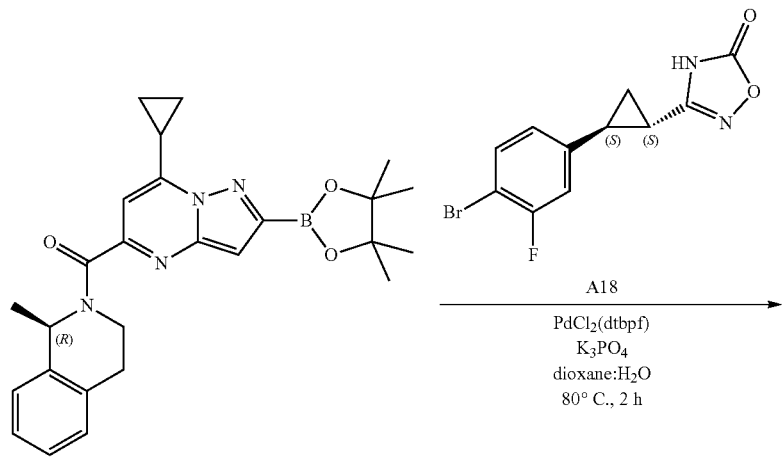

[2035421-36-2]

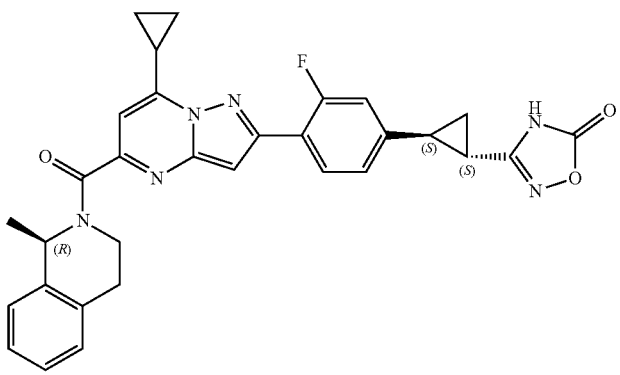

5

A sealed tube was charged with (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (315 mg, 426 μmol, 62% purity), intermediate A18 (140 mg, 468 μmol), potassium phosphate tribasic (271 mg, 1.28 mmol), 1,4-dioxane (5 mL) and H$_2$O (1 mL) and purged with nitrogen for 10 min. [1,1'-Bis(di-tert-butylphosphino)ferrocene]dichloro-palladium(II) (27.7 mg, 42.6 μmol) was added and the mixture was purged again with nitrogen for 1 min. The reaction mixture was stirred at 85° C. for 1 h. The reaction mixture was filtered over a pad of Celite®, rinsed with EtOAc and brine was added to the filtrate. The layers were separated and the aqueous phase was extracted with EtOAc (twice). The combined organic extracts were washed with water (twice), dried over MgSO$_4$, filtered and concentrated under reduced pressure. The crude mixture was purified by preparative LC (irregular SiOH, 15-40 μm, 24 g GraceResolv™, dry loading (SiOH), mobile phase gradient: heptane/EtOAc from 90:10 to 60:40). The residue was co-evaporated with EtOH (3 times) and taken up in Et$_2$O. The resulting solid was filtered off and dried under high vacuum at 50° C. for 18 h to give compound 5 (115 mg, 49%) as an off-white solid.

Compound 7
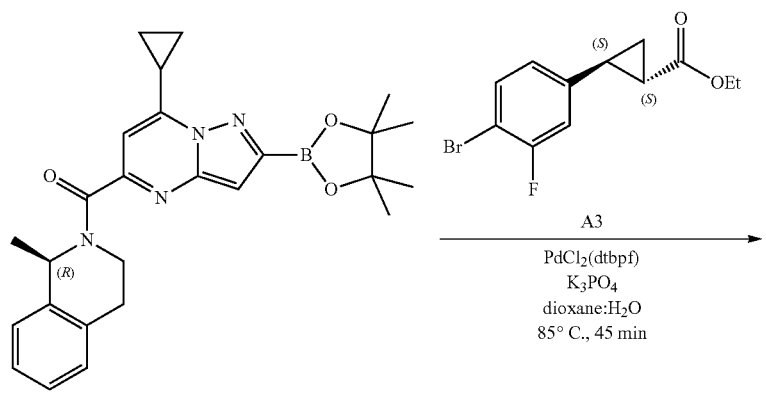
[2035421-36-2]
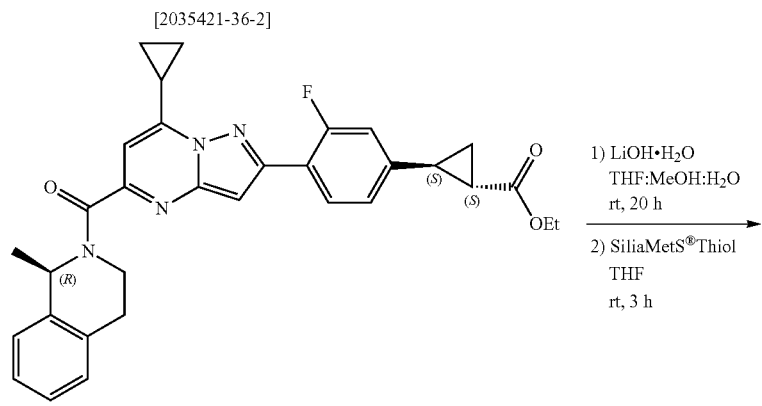
B2
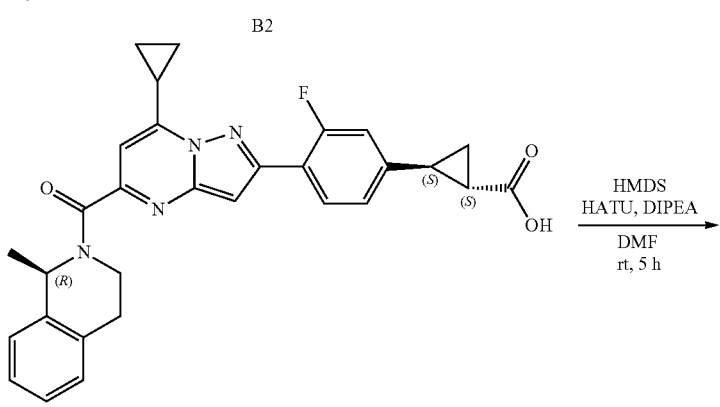
B3

Intermediate B2

Ethyl (1S,2S)-2-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropane-1-carboxylate

Intermediate B3

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropane-1-carboxylic acid

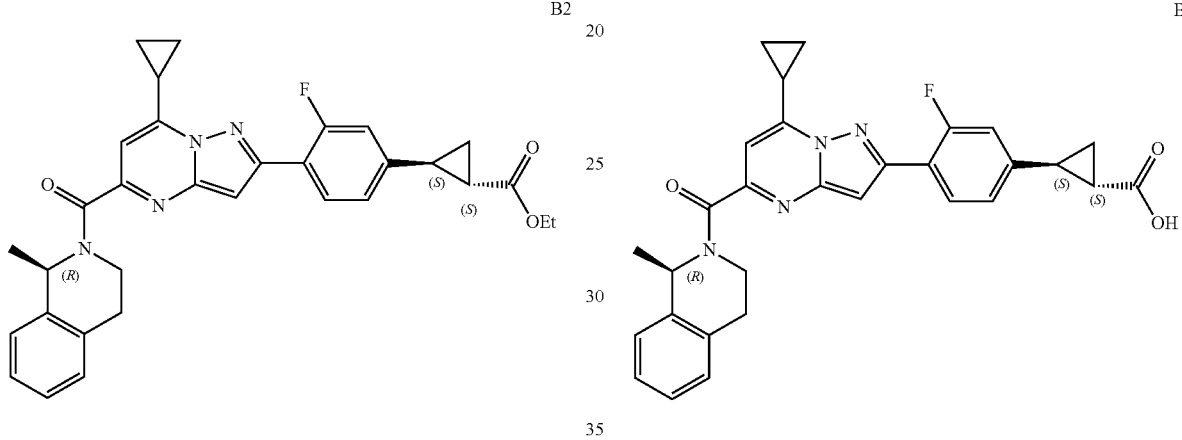

A mixture of (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (95.0 g, 94.3 mmol, 46% purity), intermediate A3 (30.7 g, 104 mmol, 97% purity) and potassium phosphate tribasic (60.1 g, 283 mmol) in 1,4-dioxane (800 mL) and H₂O (240 mL) was purged with nitrogen for 20 min. [1,1'-Bis(di-tert-butylphosphino)ferrocene]dichloro-palladium(II) (6.15 g, 9.43 mmol) was added and the mixture was purged again with nitrogen for 1 min. The reaction mixture was stirred at 85° C. for 45 min. The reaction mixture was cooled down with an ice bath, filtered over a pad of Celite®, rinsed with EtOAc and brine was added to the filtrate. The layers were separated and the aqueous phase was extracted with EtOAc (twice). The combined organic extracts were dried over MgSO₄, filtered and concentrated in vacuo. The crude mixture was purified by preparative LC (irregular SiOH, 15-40 µm, 750 g GraceResolv™, dry loading (SiOH), mobile phase gradient: heptane/EtOAc from 90:10 to 80:20) to afford intermediate B2 (60.7 g, 91%, 76% purity).

A mixture of intermediate B2 (52.5 g, 73.1 mmol, 76% purity) and lithium hydroxide monohydrate (9.20 g, 219 mmol) in THF (1 L) and H₂O (0.5 L) was stirred at rt for 20 h. Brine and a 10% aqueous solution of KHSO₄ were added until the pH was acid and the mixture was diluted with EtOAc (500 mL). The layers were separated and the aqueous phase was extracted with EtOAc (2×500 mL). The combined organic extracts were dried over MgSO₄, filtered and evaporated in vacuo. The residue was diluted with THF (450 ml) and SiliaMetS® Thiol (12.2 g, 14.6 mmol, 1.2 mmol/g) was added. The resulting mixture was stirred at rt for 3 h and filtered over a pad of Celite®, rinsed with EtOAc and the filtrate was evaporated to dryness. The product was co-evaporated with MeOH (4 times) and suspended in MeOH (1.69 L). The solution was stirred under reflux until complete solubilization. The suspension was cooled down to −20° C., filtered off, washed with cold MeOH (−40° C.) (4×200 mL) and dried under high vacuum at 60° C. for 16 h to give compound B3 (25.8 g, 69%) as a white powder. The filtrate was recrystallized from MeOH to give a second crop of compound B3 (7 g, 19%).

Compound 7

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropane-1-carboxamide

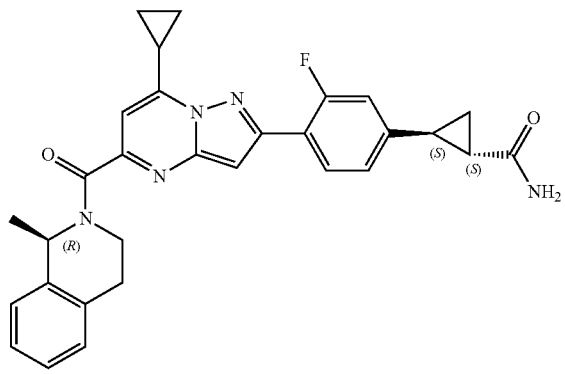

7

HATU (447 mg, 1.18 mmol) was added portionwise to a mixture of intermediate B3 (200 mg, 0.39 mmol), HMDS (0.83 mL, 3.92 mmol) and DIPEA (0.20 mL, 1.18 mmol) in DMF (5 mL). The reaction mixture was stirred at rt for 5 h. Brine was added and the aqueous phase was extracted with EtOAc (twice). The combined organic extracts were dried over MgSO₄, filtered and concentrated under reduced pressure. The crude mixture was purified by preparative LC (irregular SiOH, 15-40 µm, 24 g GraceResolv™, dry loading (SiOH), mobile phase gradient: DCM/MeOH/aq. NH₃ from 98:2:0.2 to 96:4:0.4). The residue was co-evaporated with MeOH and triturated in MeOH. The solid was filtered off, rinsed with MeOH, and dried under high vacuum at 50° C. for 18 h to give compound 7 (140 mg, 70%) as a white solid.

Compound 8

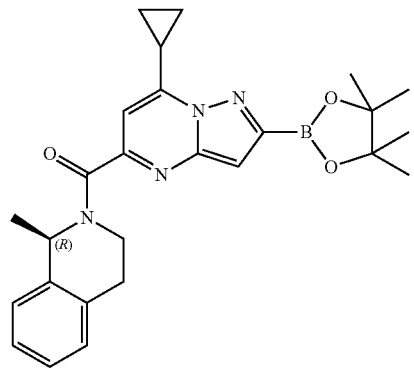

[2035421-36-2]

+

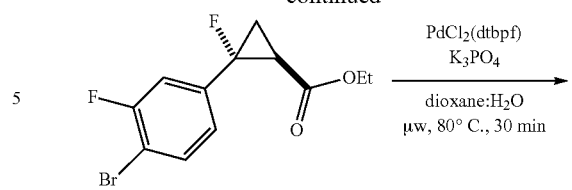

A8 (trans)

[structure] →(LiOH·H₂O, THF:H₂O, Δ, 5 h)

B4 (trans)

[structure] →(NH₃ aq. HATU, DIPEA, DMF, rt, 1 h)

B5 (trans)

[structure]

8 (trans)

Intermediate B4

Ethyl trans-2-{7-cyclopropyl-5-[(1R)-1-methyl-1,2,3,4-tetrahydroisoquinoline-2-carbonyl]pyrazolo[1,5-a]pyrimidin-2-yl}-2-fluorocyclopropane-1-carboxylate

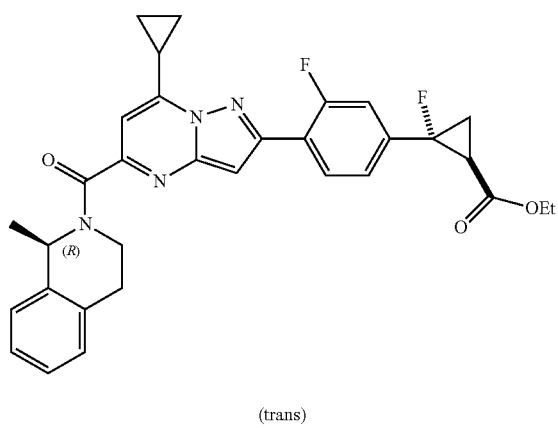

(trans)

A mixture of (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (0.40 g, 0.54 mmol, 62% purity), intermediate A8 (182 mg, 0.60 mmol) and potassium phosphate tribasic (345 mg, 1.62 mmol) in 1,4-dioxane (5 mL) and H$_2$O (1 mL) was purged with nitrogen for 5 min. [1,1'-Bis(di-tert-butylphosphino)ferrocene]dichloropalladium(II) (35.3 mg, 54.1 μmol) was added and the mixture was purged again with nitrogen for 5 min. The reaction mixture was heated at 80° C. using a single mode microwave (Anton Paar Monowave 300) with a power output ranging from 0 to 850 W for 30 min. The reaction mixture was diluted with EtOAc and water. The layers were separated and the aqueous phase was extracted with EtOAc (twice). The combined organic extracts were washed with brine, dried over MgSO$_4$, filtered and evaporated to dryness. The crude mixture was purified by flash chromatography over silica gel (Puriflash Interchim® 25 g, 30 μM, liquid injection (DCM), mobile phase gradient: heptane/EtOAc from 100:0 to 60:40) to afford intermediate B4 (0.26 g, 86%) as a beige solid.

Intermediate B5 trans-2-{7-Cyclopropyl-5-[(1R)-1-methyl-1,2,3,4-tetrahydroisoquinoline-2-carbonyl]pyrazolo[1,5-a]pyrimidin-2-yl}-2-fluorocyclopropane-1-carboxylic acid

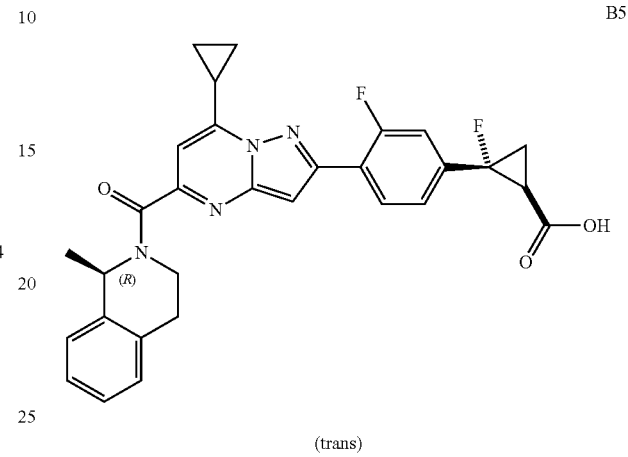

(trans)

A mixture of intermediate B4 (0.25 g, 449 μmol) and lithium hydroxide monohydrate (113 mg, 2.70 mmol) in THF (10 mL) and H$_2$O (3 mL) was stirred under reflux for 5 h. An aqueous solution of citric acid (518 mg) was added. The layers were separated and the aqueous phase was extracted with EtOAc. The combined organic extracts were washed with brine, dried over MgSO$_4$, filtered and evaporated to dryness to afford intermediate B5 (0.21 g, 88%) as a yellow solid.

Compound 8 trans-2-{7-Cyclopropyl-5-[(1R)-1-methyl-1,2,3,4-tetrahydroisoquinoline-2-carbonyl]pyrazolo[1,5-a]pyrimidin-2-yl}-2-fluorocyclopropane-1-carboxamide

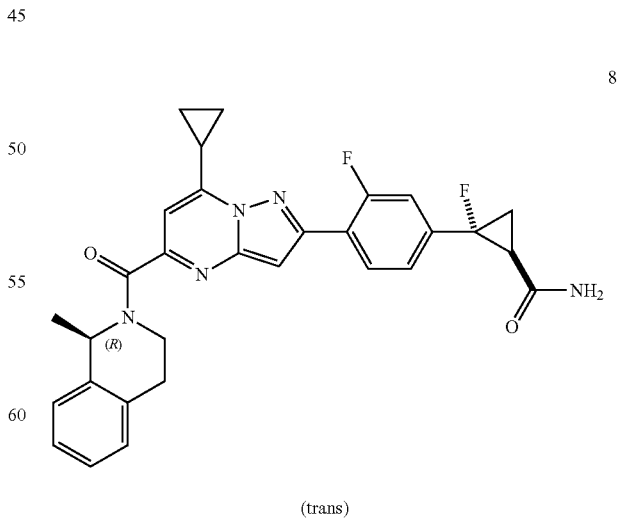

(trans)

To a solution of intermediate B5 (0.20 g, 378 μmol) in DMF (5 mL) were added DIPEA (0.2 mL, 1.14 mmol) and HATU (216 mg, 568 µmop. The reaction mixture was stirred at rt for 15 min and ammonia (30% in H₂O, 43 µL, 2.27 mmol) was added dropwise. The reaction mixture was stirred at rt for 1 h. The reaction mixture was diluted with water and EtOAc. The layers were separated and the organic phase was washed with water (3 times) and brine, dried over MgSO₄, filtered and evaporated to dryness. The crude mixture was purified by flash chromatography over silica gel (Puriflash Interchim® 12 g, 30 µM, liquid injection (DCM), mobile phase gradient: DCM/MeOH from 100:0 to 98:2). The residue (0.12 g) was purified by preparative LC (X-Bridge-C18 5 µm, 40 g, mobile phase gradient: (0.5% aq. NH₄HCO₃)/MeCN from 35:65 to 0:100) to give compound 8 (35 mg, 18%) as a white solid.

Compound 9

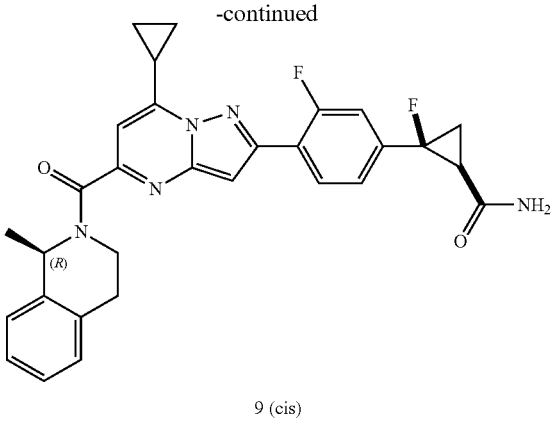

9 (cis)

Intermediate B6

Ethyl cis-2-{7-cyclopropyl-5-[(1R)-1-methyl-1,2,3,4-tetrahydroisoquinoline-2-carbonyl]pyrazolo[1,5-a]pyrimidin-2-yl}-2-fluorocyclopropane-1-carboxylate

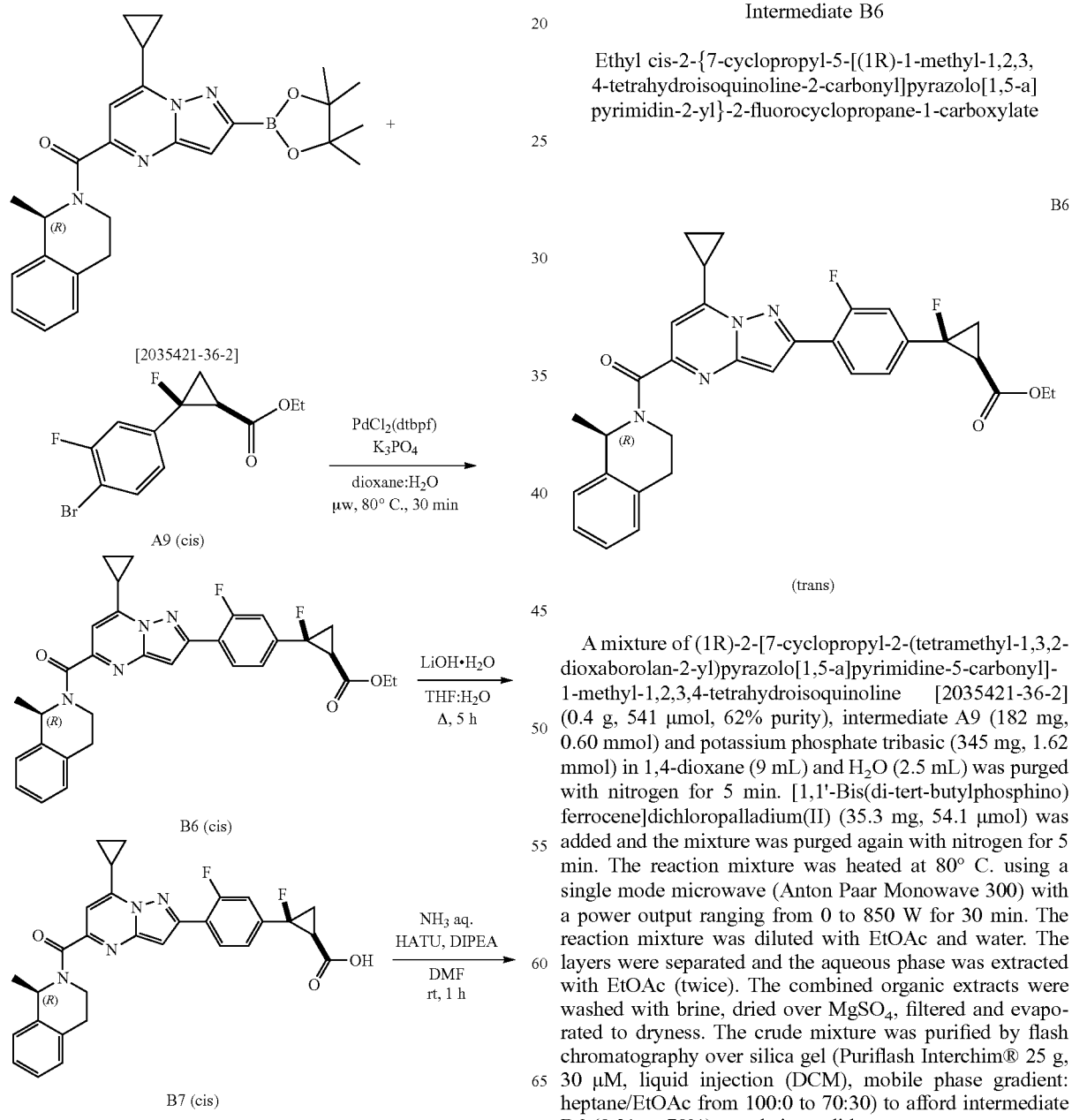

A mixture of (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (0.4 g, 541 µmol, 62% purity), intermediate A9 (182 mg, 0.60 mmol) and potassium phosphate tribasic (345 mg, 1.62 mmol) in 1,4-dioxane (9 mL) and H₂O (2.5 mL) was purged with nitrogen for 5 min. [1,1'-Bis(di-tert-butylphosphino)ferrocene]dichloropalladium(II) (35.3 mg, 54.1 µmol) was added and the mixture was purged again with nitrogen for 5 min. The reaction mixture was heated at 80° C. using a single mode microwave (Anton Paar Monowave 300) with a power output ranging from 0 to 850 W for 30 min. The reaction mixture was diluted with EtOAc and water. The layers were separated and the aqueous phase was extracted with EtOAc (twice). The combined organic extracts were washed with brine, dried over MgSO₄, filtered and evaporated to dryness. The crude mixture was purified by flash chromatography over silica gel (Puriflash Interchim® 25 g, 30 µM, liquid injection (DCM), mobile phase gradient: heptane/EtOAc from 100:0 to 70:30) to afford intermediate B6 (0.21 g, 70%) as a beige solid.

Intermediate B7 cis-2-{7-Cyclopropyl-5-[(1R)-1-methyl-1,2,3,4-tetrahydroisoquinoline-2-carbonyl]pyrazolo[1,5-a]pyrimidin-2-yl}-2-fluorocyclopropane-1-carboxylic acid

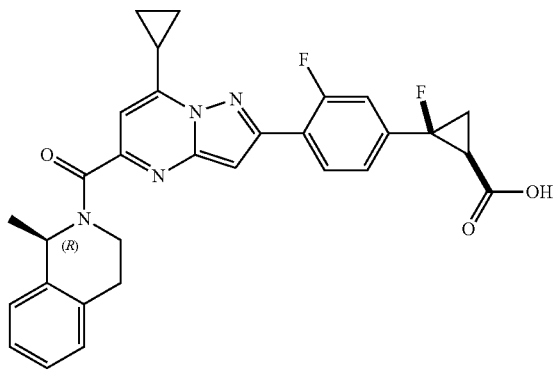

(cis)

A mixture of intermediate B6 (0.21 g, 377 μmol) and lithium hydroxide monohydrate (95 mg, 2.26 mmol) in THF (10 mL) and H$_2$O (3 mL) was stirred under reflux for 6 h. An aqueous solution of citric acid (435 mg) was added. The layers were separated and the aqueous phase was extracted with EtOAc. The combined organic extracts were washed with brine, dried over MgSO$_4$, filtered and evaporated to dryness to afford intermediate B7 (0.19 g, quant.) as a yellow solid.

Compound 9 cis-2-{7-Cyclopropyl-5-[(1R)-1-methyl-1,2,3,4-tetrahydroisoquinoline-2-carbonyl]pyrazolo[1,5-a]pyrimidin-2-yl}-2-fluorocyclopropane-1-carboxamide

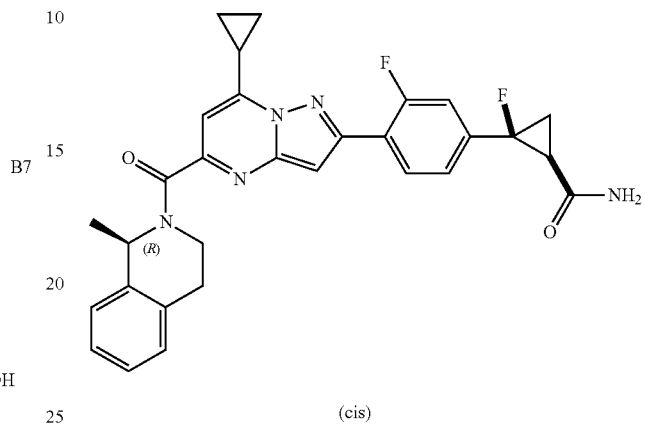

(cis)

To a solution of intermediate B7 (0.19 g, 359 μmol) in DMF (5 mL) were added DIPEA (0.19 mL, 1.08 mmol) and HATU (205 mg, 0.54 mmol). The mixture was stirred at rt for 15 min and ammonia (30% in H$_2$O, 41 μL, 2.16 mmol) was added dropwise. The reaction mixture was stirred at rt for 2 h. The reaction mixture was diluted with water and EtOAc. The layers were separated and the organic phase was washed with water (3 times) and brine, dried over MgSO$_4$, filtered and evaporated to dryness. The crude mixture was purified by flash chromatography over silica gel (Puriflash Interchim® 12 g, 30 μM, liquid injection (DCM), mobile phase gradient: DCM/MeOH from 100:0 to 98:2). The residue (0.1 g) was diluted with i-PrOH and stirred for 20 min at rt. The solid was filtered off and dried under vacuum to give compound 9 (0.04 g, 21%) as a white solid.

Compound 10

(1S,2S)-2-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)cyclopropane-1-carboxamide

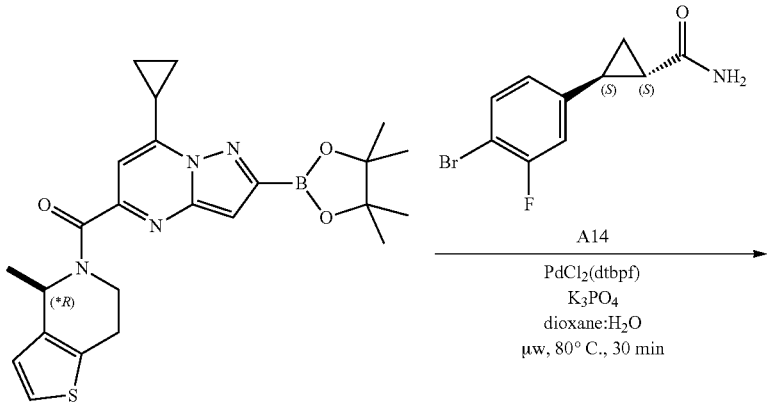

[2035420-25-6]

Compound 11

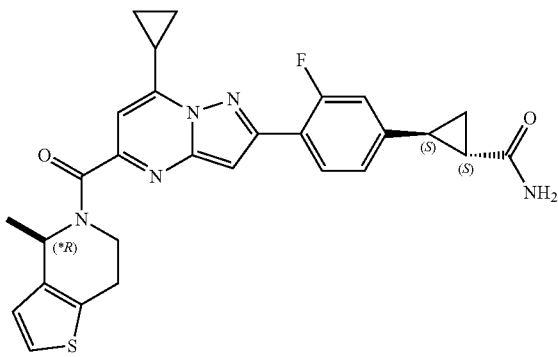
10

A sealed tube was charged with 7-cyclopropyl-5-[(4*R)-4-methyl-4,5,6,7-tetrahydro-thieno[3,2-c]pyridine-5-carbonyl]-2-(tetramethyl-1,3,2-dioxaborolan-2-yl)pyrazolo[1,5-a]pyrimidine [2035420-25-6] (288 mg, 409 µmol, 66% purity), intermediate A14 (116 mg, 450 µmol), potassium phosphate tribasic (296 mg, 1.40 mmol), 1,4-dioxane (7.5 mL) and H₂O (2.5 mL) and purged with nitrogen. [1,1'-Bis (di-tert-butylphosphino)ferrocene]-dichloropalladium(II) (29.3 mg, 45.0 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and washed with a saturated aqueous solution of NaHCO₃ and brine. The solid was filtered off and washed with EtOAc to give a first crop. The filtrate was decanted and the organic phase was dried over MgSO₄, filtered and evaporated in vacuo. The crude mixture was purified by preparative LC (regular SiOH, 15-30 µm, 25 g Interchim®, dry loading (SiOH), mobile phase gradient: heptane/EtOAc from 50:50 to 0:100 then DCM/MeOH from 90:10 to 85:15) to deliver a second crop of compound 10. The first crop, previously isolated, was diluted in DMF. Insoluble residue was filtered off and discarded. The soluble mixture was purified by preparative LC (regular SiOH, 15-30 µm, 25 g Interchim®, dry loading (SiOH), mobile phase gradient: DCM/MeOH from 90:10 to 85:15). The solid was triturated in Et₂O and filtered off to deliver a third crop of compound 10. The second and third crops were combined and purified by preparative LC (spherical C18 25 µm, 120 g YMC-ODS-25, dry loading (Celite®), mobile phase gradient (0.2% aq. NH₄HCO₃)/MeCN from 65:35 to 0:100 then MeCN). The fractions containing the product were combined and concentrated to dryness. A second purification was performed by preparative LC (regular SiOH, 15-30 µm, 25 g Interchim®, dry loading (SiOH), mobile phase gradient: DCM/MeOH from 90:10 to 85:15). The solid was triturated in Et₂O, filtered off and washed with Et₂O. The solid was triturated in DCM, filtered off and washed with DCM to give compound 10 (50 mg, 24%) as a white solid.

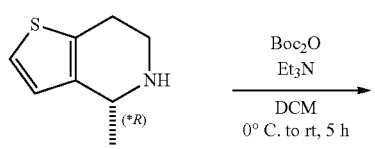

[1176986-86-9]

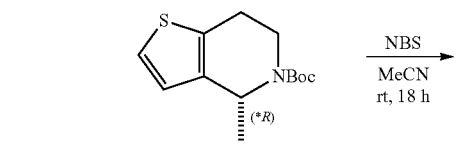

C1

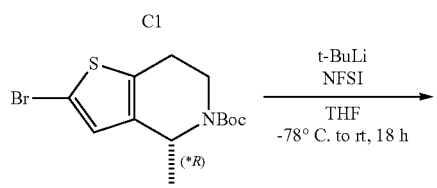

C2

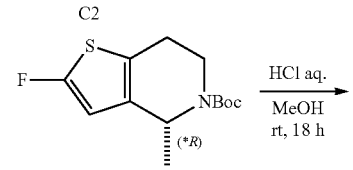

C3

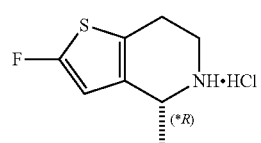

C4

-continued

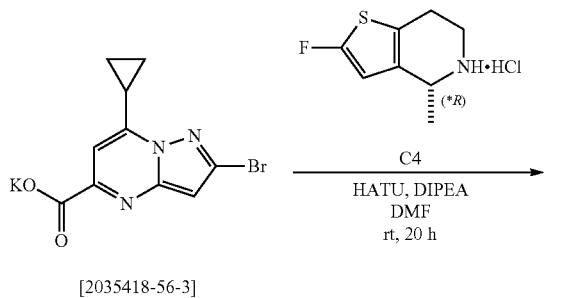

[2035418-56-3]

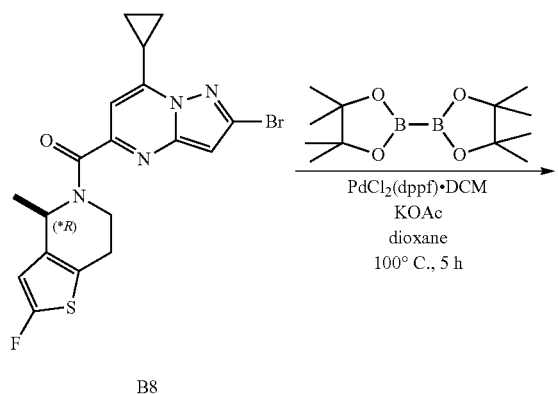

B8

B9

11

Intermediate C1

Tert-butyl (4*R)-4-methyl-4,5,6,7-tetrahydro-thieno[3,2-c]pyridine-5-carboxylate

C1

A solution of di-tert-butyl dicarbonate (1.42 g, 6.53 mmol) in DCM (5 mL) was added dropwise to a mixture of (4*R)-4-methyl-4,5,6,7-tetrahydro-thieno[3,2-c]pyridine [1176986-86-9] (1.00 g, 6.53 mmol) and Et$_3$N (1.1 mL, 7.91 mmol) in DCM (7 mL) at 0° C. (the internal temperature was maintained between 10 and 20° C.). The reaction mixture was stirred at rt for 5 h. The mixture was evaporated in vacuo. The residue was diluted with water and EtOAc and a saturated aqueous solution of NaHCO$_3$ was added. The layers were separated and the aqueous phase was extracted with EtOAc (twice). The combined organic extracts were dried over MgSO$_4$, filtered and evaporated in vacuo. The crude mixture was purified by preparative LC (irregular SiOH, 15-40 μm, 50 g Grace Resolv™, liquid injection (heptane), mobile phase gradient: heptane/EtOAc from 100:0 to 80:20) to afford intermediate C1 (1.45 g, 88%) as a colorless oil that crystallized on standing.

Intermediate C2

Tert-butyl (4*R)-2-bromo-4-methyl-4,5,6,7-tetra-hydro-thieno[3,2-c]pyridine-5-carboxylate

C2

To a solution of intermediate C1 (1.45 g, 5.72 mmol) in MeCN (31 mL) was added NBS (1.02 g, 5.72 mmol) portionwise. The reaction mixture was stirred at rt for 18 h. The reaction mixture was diluted with EtOAc and brine. The layers were separated and the organic phase was washed with water and brine, dried over MgSO$_4$, filtered and evaporated in vacuo. The crude mixture was purified by preparative LC (irregular SiOH, 15-40 μm, 50 g GraceResolv™, dry loading (Celite®), mobile phase gradient: heptane/EtOAc from 100:0 to 90:10 to afford intermediate C2 (1.66 g, 87%) as a colorless gum.

Intermediate C3

Tert-butyl (4*R)-2-fluoro-4-methyl-4,5,6,7-tetra-hydro-thieno[3,2-c]pyridine-5-carboxylate

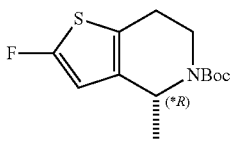

C3

Tert-butyllithium (1.9 M in pentane, 58 mL, 110 mmol) was added dropwise to a solution intermediate C2 (15.9 g, 47.9 mmol) in anhydrous THF (400 mL) at −78° C. The reaction mixture was stirred at −78° C. for 45 min and a solution of NFSI (45.3 g, 144 mmol) in THF (170 mL) was added. The reaction mixture was stirred at −78° C. for 30 min and at rt for 18 h. The reaction was quenched by the addition of a saturated aqueous solution of $NH_4Cl$ and diluted with EtOAc. The layers were separated and the organic phase was evaporated to dryness. The crude mixture was purified by preparative LC (irregular SiOH, 15-40 μm, 330 g GraceResolv™, dry loading (Celite®), mobile phase gradient: heptane/EtOAc from 100:0 to 90:10). The residue was purified by reverse phase (spherical C18, 25 μm, 300 g YMC-ODS-25, liquid injection (MeCN, 2-3 mL), mobile phase gradient: (0.2% aq. $NH_4HCO_3$)/MeCN from 50:50 to 25:75). The pure fractions were combined and evaporated in vacuo to afford intermediate C3 (6.5 g, 50%) as a colorless oil.

Intermediate C4

(4*R)-2-Fluoro-4-methyl-4,5,6,7-tetrahydro-thieno[3,2-c]pyridine hydrochloride

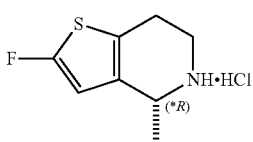

C4

Hydrochloric acid (37% in $H_2O$, 2.21 mL, 26.4 mmol) was added dropwise to a solution of intermediate C3 (2.21 g, 8.14 mol) in MeOH (10 mL). The reaction mixture was stirred at rt for 18 h. The mixture was evaporated in vacuo and the residue was co-evaporated with EtOH (twice) and $Et_2O$ to afford intermediate C4 (1.65 g, 98%) as a white solid.

Intermediate B8

2-Bromo-7-cyclopropyl-5-[(4*R)-2-fluoro-4-methyl-4,5,6,7-tetrahydro-thieno[3,2-c]pyridine-5-carbonyl]pyrazolo[1,5-a]pyrimidine

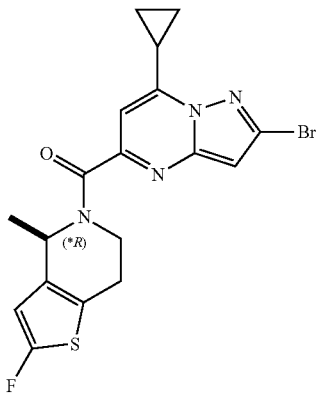

B8

A mixture of potassium 2-bromo-7-cyclopropylpyrazolo[1,5-a]pyrimidine-5-carboxylic acid [2035418-56-3] (2.31 g, 7.22 mmol), intermediate C4 (1.65 g, 7.94 mmol), HATU (5.49 g, 14.4 mmol) and DIPEA (5.00 mL, 29.0 mmol) in DMF (45 mL) was stirred at rt for 20 h. A saturated aqueous solution of $NaHCO_3$, brine and EtOAc were added. The layers were separated and the aqueous phase was extracted with EtOAc (twice). The combined organic extracts were washed with brine (4 times), dried over $MgSO_4$, filtered and evaporated in vacuo. The crude mixture was purified by preparative LC (irregular SiOH, 15-40 μm, 120 g GraceResolv™, liquid injection (DCM), mobile phase gradient: heptane/EtOAc from 90:10 to 60:40) to afford intermediate B8 (3.02 g, 96%) as a white foam.

Intermediate B9

7-Cyclopropyl-5-[(4*R)-2-fluoro-4-methyl-4,5,6,7-tetrahydro-thieno[3,2-c]pyridine-5-carbonyl]-2-(tetramethyl-1,3,2-dioxaborolan-2-yl)pyrazolo[1,5-a]pyrimidine

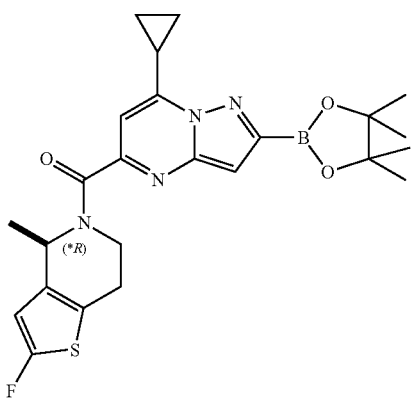

B9

Under nitrogen a sealed tube was charged with a solution of intermediate B8 (250 mg, 574 µmol) in 1,4-dioxane (2.6 mL). Bis(pinacolato)diboron (219 mg, 861 µmol) and potassium acetate (169 mg, 1.72 mmol) were added. The mixture was purged with nitrogen and [1,1'-bis(diphenylphosphino)ferrocene] dichloropalladium(II), complex with dichloromethane (47.0 mg, 57.4 µmol) was added. The mixture was purged again with nitrogen and the reaction mixture was stirred at 100° C. for 5 h. The reaction mixture was diluted with EtOAc, washed with water and brine (twice), dried over MgSO₄, filtered and concentrated under reduced pressure. The product B9 (557 mg, 51% purity) was used in the next step without further purification.

Compound 11

(1S,2S)-2-(4-{7-Cyclopropyl-5-[(4*R)-2-fluoro-4-methyl-4,5,6,7-tetrahydro-thieno[3,2-c]pyridine-5-carbonyl]pyrazolo[1,5-a]pyrimidin-2-yl}-3-fluorophenyl)cyclopropane-1-carboxamide

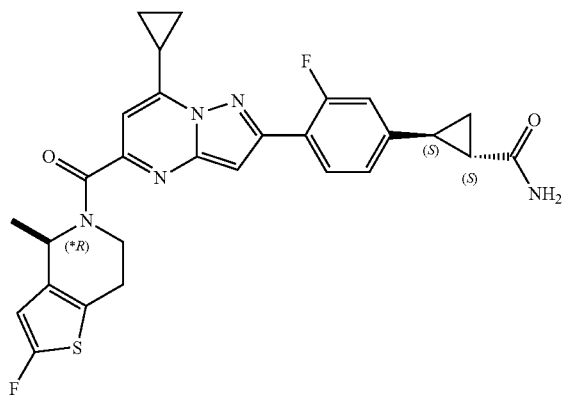

A sealed tube was charged with intermediate A14 (187 mg, 0.42 mmol, 59% purity), intermediate B9 (480 mg, 0.51 mmol, 51% purity), potassium phosphate tribasic (307 mg, 1.45 mmol), 1,4-dioxane (7.8 mL) and H₂O (2.8 mL) and purged with nitrogen. [1,1'-Bis(di-tert-butylphosphino)ferrocene]dichloropalladium(II) (30.3 mg, 46.6 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and water. The layers were separated and the organic phase was washed with brine, dried over MgSO₄, filtered and concentrated under reduced pressure. The crude mixture was purified by preparative LC (regular SiOH, 15-40 µm, 24 g GraceResolv™, dry loading (Celite®), mobile phase gradient: DCM/MeOH/aq. NH₃ from 100:0:0 to 90:10:1). The resulting solid was triturated in MeOH and filtered off. The solid was combined with mother-liquor and purified by reverse phase (spherical C18, 25 µm, 40 g YMC-ODS-25, dry loading (Celite®), mobile phase gradient: (0.2% aq. NH₄HCO₃)/MeCN from 65:35 to 0:100). The solid was triturated in MeOH, filtered off and dried under high vacuum at 50° C. for 24 h to afford an off-white solid (79 mg). Another purification was carried out by reverse phase (Stationary phase: YMC-actus Triart-C18 10 µm 30*150 mm, Mobile phase gradient: (0.2% aq. NH₄HCO₃)/MeCN from 60:40 to 0:100). The solid was triturated in MeOH, filtered off and dried under high vacuum at 50° C. for 18 h to give compound 9 (27 mg, 12%) as a white solid.

Compound 12

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-methylcyclopropane-1-carboxamide

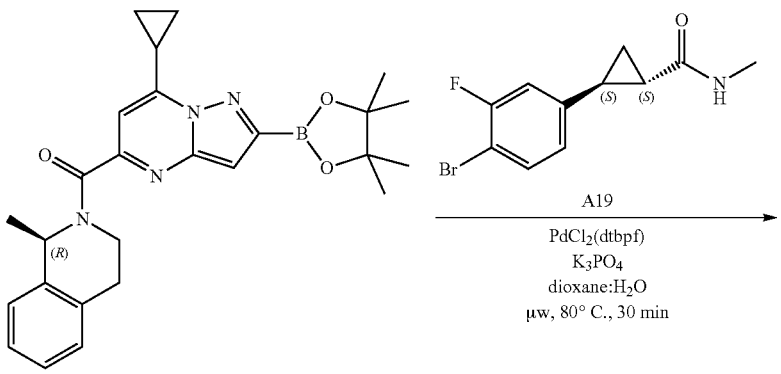

[2035421-36-2]

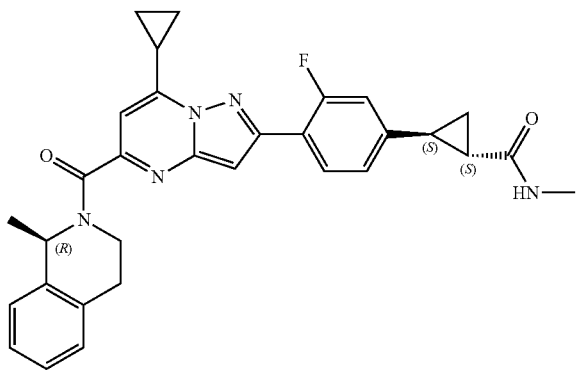

12

A sealed tube was charged with (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (448 mg, 655 µmol, 67% purity), intermediate A19 (198 mg, 656 µmol), potassium phosphate tribasic (475 mg, 2.24 mmol), 1,4-dioxane (10 mL) and H₂O (3 mL) and purged with nitrogen. [1,1'-Bis(di-tert-butylphosphino)ferrocene]dichloro-palladium(II) (47.0 mg, 72.1 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and water. The layers were separated and the aqueous phase was extracted with EtOAc. The combined organic extracts were washed with brine, dried over MgSO₄, filtered and evaporated in vacuo. The crude mixture was purified by preparative LC (irregular SiOH, 40 g Grace®, liquid injection (DCM), mobile phase gradient: DCM/MeOH from 100:0 to 90:10). The solid was triturated in MeOH, filtered off and dried under vacuum at 50° C. to give compound 12 (160 mg, 47%) as an off-white solid.

Compound 13

(1S,2S)—N-Cyano-2-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropane-1-carboxamide

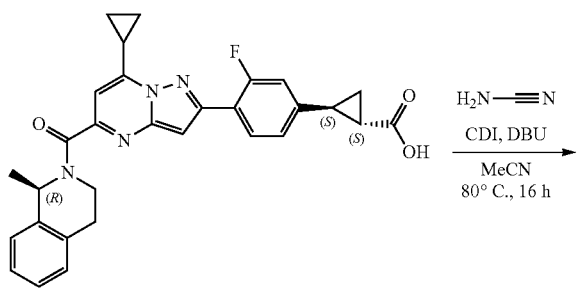

B3

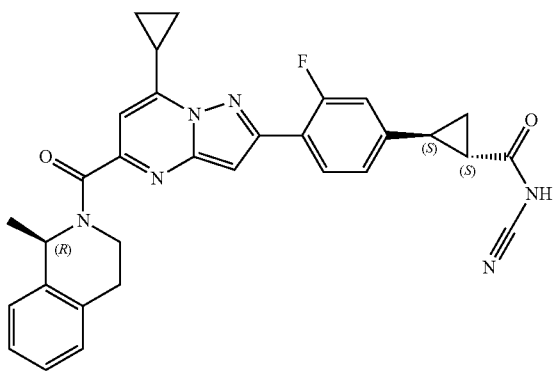

13

A mixture of intermediate B3 (200 mg, 0.39 mmol) and CDI (95.3 mg, 0.59 mmol) in MeCN (4.0 mL) was stirred at rt for 2 h. DBU (117 µL, 0.78 mmol) and cyanamide [420-04-2] (32.9 mg, 0.78 mmol) were added. The reaction mixture was stirred at 80° C. for 16 h. The solvent was evaporated in vacuo. The crude mixture was purified by preparative LC (irregular SiOH, 15-40 µm, 24 g GraceResolv™, liquid injection (DCM), mobile phase gradient: DCM/MeOH/AcOH from 100:0:0 to 95:4.5:0.5). The residue was crystallized from MeCN and dried under vacuum at 50° C. for 16 h. The solid was purified by reverse phase (Stationary phase: YMC-actus Triart C18 10 µm 30*150 mm, Mobile phase gradient: (0.2% aq. NH₄HCO₃)/MeCN from 75:25 to 35:65) to give compound 13 (70 mg, 33%).

Compound 14

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-ethylcyclopropane-1-carboxamide

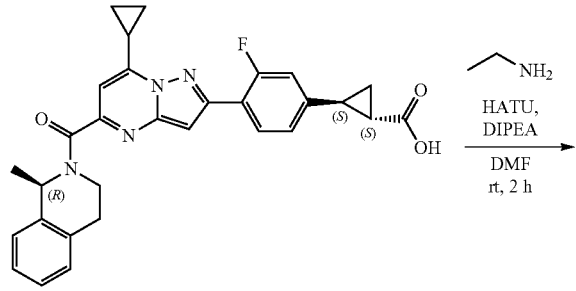

B3

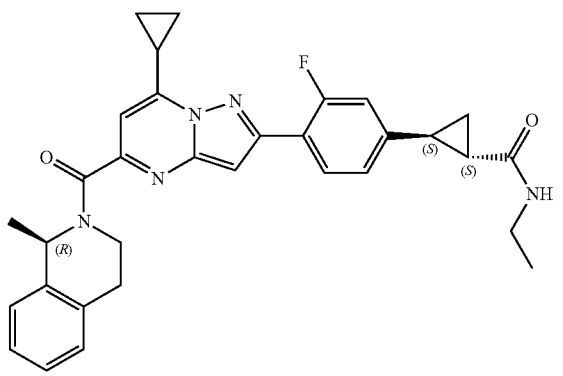

14

To a mixture of intermediate B3 (0.2 g, 0.39 mmol) in DMF (5 mL) were added DIPEA (0.20 mL, 1.18 mmol) and HATU (0.22 g, 0.59 mmol). The reaction mixture was stirred at rt for 15 min and ethylamine (2.0 M in MeOH, 1.18 mL, 2.35 mmol) was added dropwise. The reaction mixture was stirred at rt for 2 h. The reaction mixture was diluted with water and EtOAc. The layers were separated and the organic phase was washed with water and brine (3 times), dried over MgSO$_4$, filtered and evaporated to dryness. The residue was taken up in Et$_2$O. The solid was filtered off and dried under vacuum to give compound 14 (75 mg, 36%).

Compound 15

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-propylcyclopropane-1-carboxamide

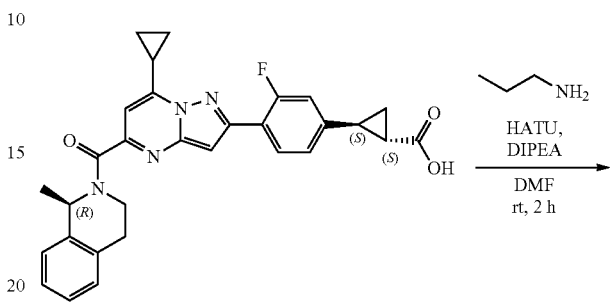

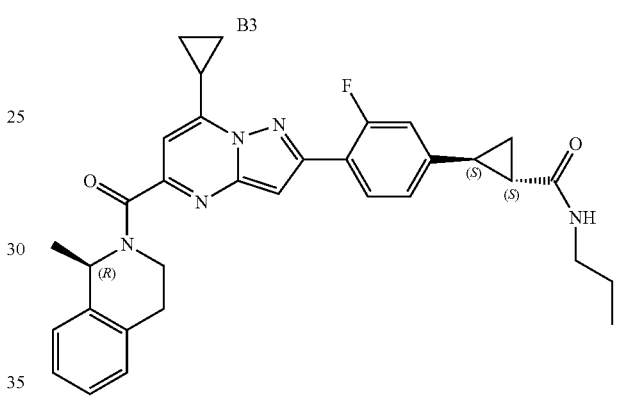

15

Compound 15 was synthesized from intermediate B3 and propylamine [107-10-8] according to the procedure reported for the synthesis of compound 14. The residue was taken up in DIPE. The solid was filtered off and dried under vacuum to give compound 15 (0.15 g, 69%) as a beige solid.

Compound 16

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-(prop-2-en-1-yl)cyclopropane-1-carboxamide

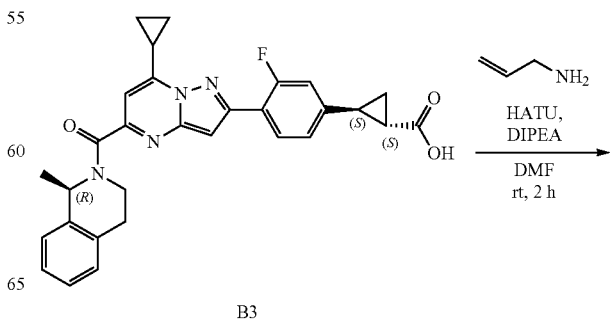

B3

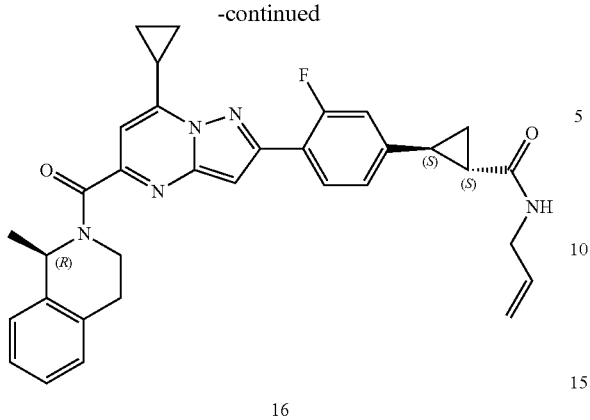

16

Compound 16 was synthesized from intermediate B3 and allylamine [107-11-9] according to the procedure reported for the synthesis of compound 14. Compound 16 (98 mg, 46%) was obtained as a beige solid.

Compound 17

(1S,2S)-2-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-(prop-2-yn-1-yl)cyclopropane-1-carboxamide

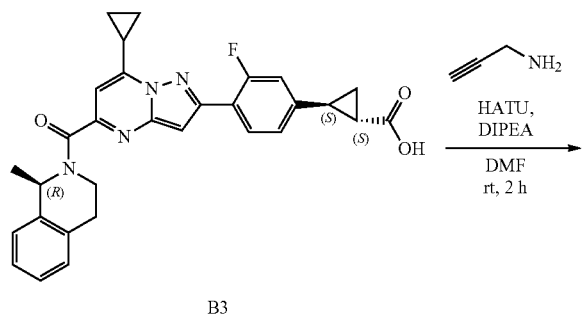

B3

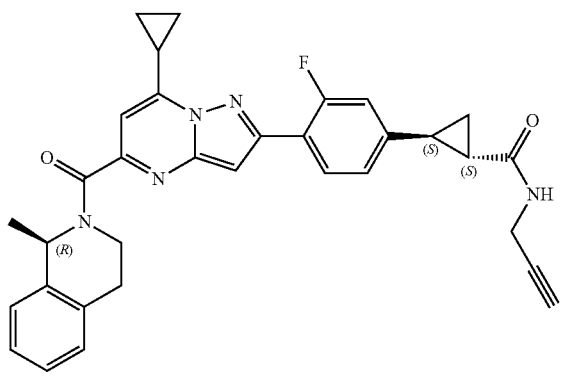

17

Compound 17 was synthesized from intermediate B3 and propargylamine [2450-71-7] according to the procedure reported for the synthesis of compound 14. Compound 17 (0.2 g, 93%) was obtained as a beige solid.

Compound 18

(1S,2S)—N-(2-Cyanoethyl)-2-(4-{7-cyclopropyl-5-[(1R)-1-methyl-1,2,3,4-tetrahydro-isoquinoline-2-carbonyl]pyrazolo[1,5-a]pyrimidin-2-yl}-3-fluorophenyl)cyclopropane-1-carboxamide

B3

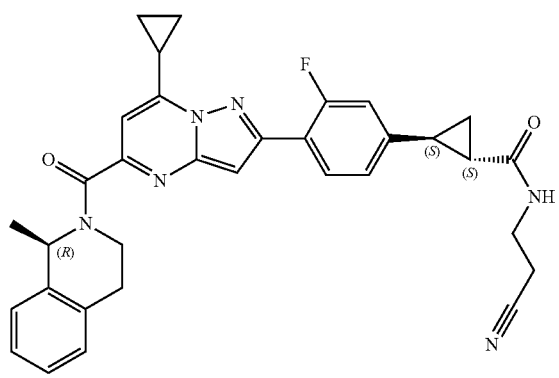

18

Compound 18 was synthesized from intermediate B3 and 3-aminopropionitrile according to the procedure reported for the synthesis of compound 14. Compound 18 (187 mg, 85%) was obtained as a beige solid.

Compound 19

(1S,2S)-2-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-(oxetan-3-yl)cyclopropane-1-carboxamide

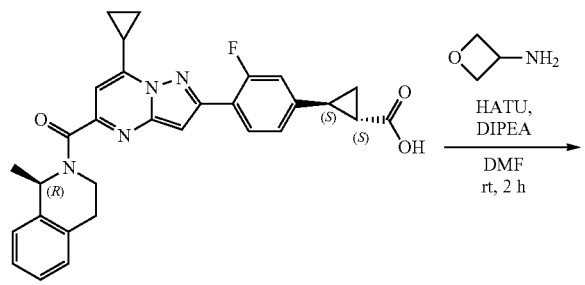

B3

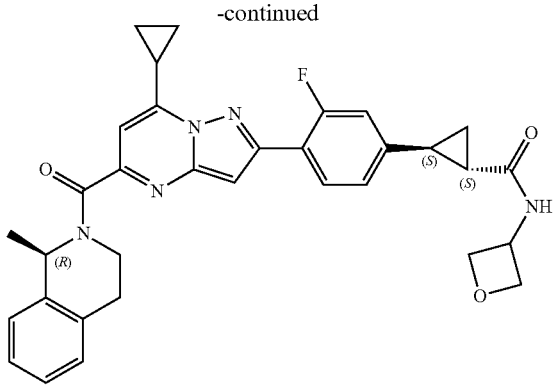

19

Compound 19 was synthesized from intermediate B3 and 3-oxetamine [21635-88-1] according to the procedure reported for the synthesis of compound 14. Compound 19 (182 mg, 82%) was obtained as a white solid.

Compound 20

(1S,2S)-2-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-(1-methylcyclopropyl)cyclopropane-1-carboxamide

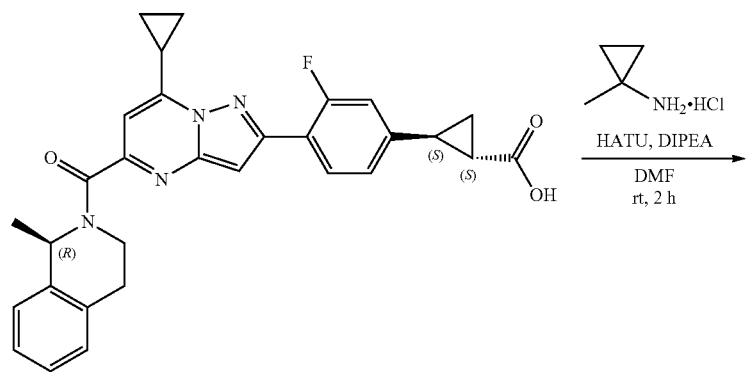

B3

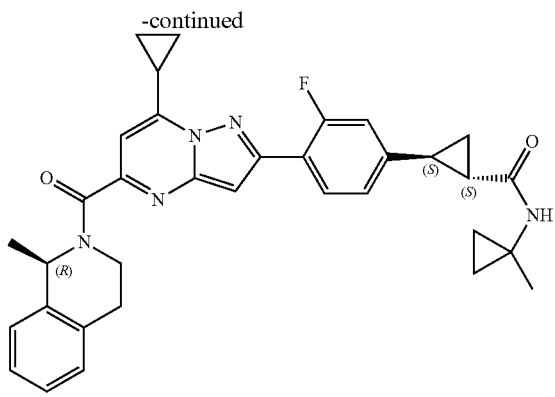

20

To a solution of intermediate B3 (0.15 g, 0.29 mmol) in DMF (5 mL) were added DIPEA (0.30 mL, 1.76 mmol) and HATU (0.17 g, 0.44 mmol). The reaction mixture was stirred at rt for 15 min and 1-methylcyclopropylamine hydrochloride [88887-87-0] (0.13 g, 1.18 mmol) was added. The reaction mixture was stirred at rt for 2 h. The reaction mixture was diluted with water and EtOAc. A precipitate was formed and filtered off to give compound 20 (100 mg, 60%) as a white solid.

Compound 21

(1S,2S)-2-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-(2-hydroxyethyl)-cyclopropane-1-carboxamide

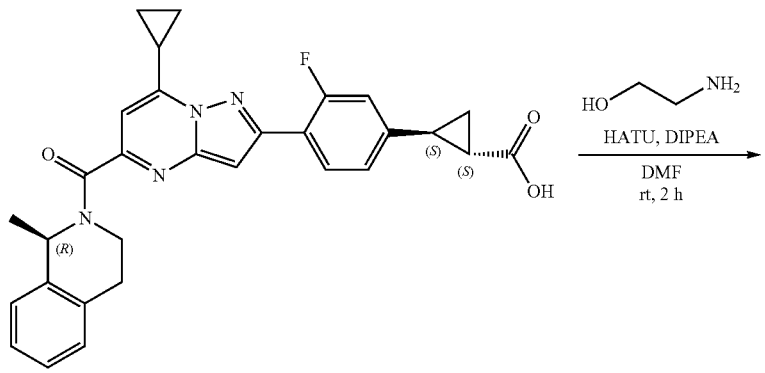

B3

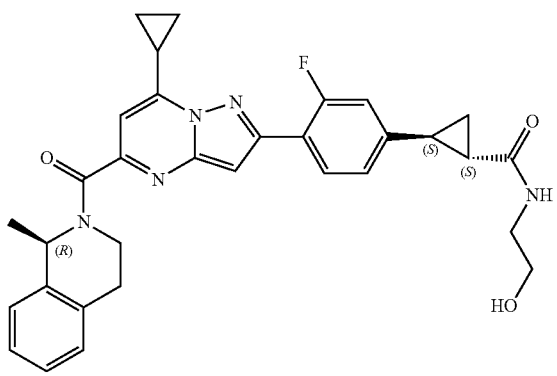

21

Compound 21 was synthesized from intermediate B3 and ethanolamine [141-43-5] according to the procedure reported for the synthesis of compound 20. Compound 21 (145 mg, 67%) was obtained as a white solid.

Compound 22

(1S,2S)-2-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N,N-dimethyl-cyclopropane-1-carboxamide

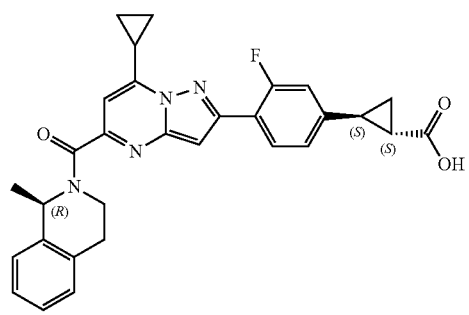

B3

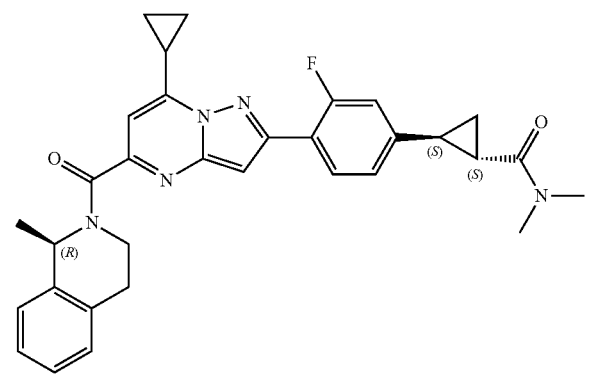

22

HATU (168 mg, 0.44 mmol) was added to a suspension of intermediate B3 (150 mg, 0.29 mmol), dimethylamine (2.0 M in THF, 740 µL, 1.48 mmol) and DIPEA (152 µL, 0.881 mmol) in DMF (2 mL). The reaction mixture was stirred at rt for 18 h. The reaction mixture was diluted with H₂O, brine and EtOAc. The layers were separated and the aqueous phase was extracted with EtOAc. The combined organic extracts were washed with brine (3 times), dried over MgSO₄, filtered and evaporated in vacuo. The crude mixture was purified by preparative LC (irregular SiOH, 15-40 µm, 12 g GraceResolv™, liquid injection (DCM), mobile phase gradient: heptane/(EtOAc/MeOH, 90:10) from 80:20 to 60:40). The residue was taken up in Et₂O and evaporated in vacuo (twice) to give compound 22 (117 mg, 74%) as an off-white solid.

Compound 23

(1R)-2-(7-Cyclopropyl-2-{2-fluoro-4-[(1S,2S)-2-(pyrrolidine-1-carbonyl)cyclopropyl]-phenyl}pyrazolo[1,5-a]pyrimidine-5-carbonyl)-1-methyl-1,2,3,4-tetrahydroisoquinoline

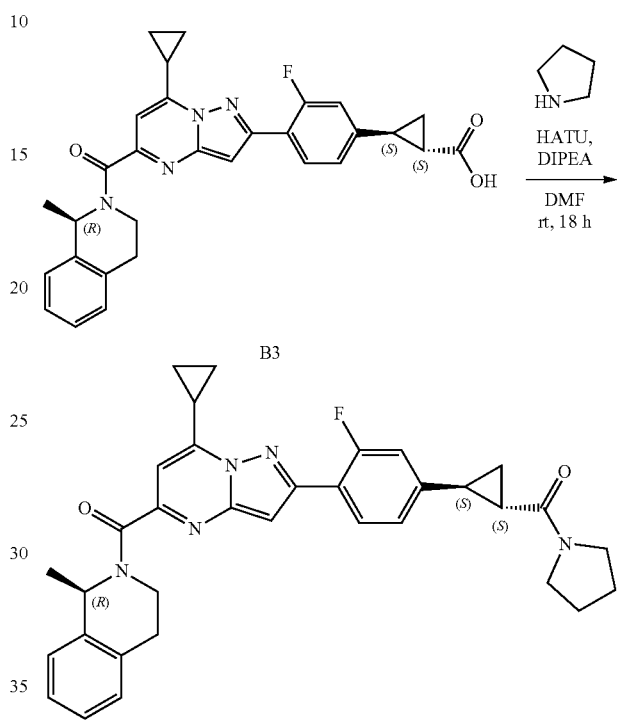

23

Compound 23 was synthesized from intermediate B3 and pyrrolidine [123-75-1] according to the procedure reported for the synthesis of compound 22. Compound 23 (112 mg, 68%) was obtained as an off-white solid.

Compound 24

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-methanesulfonyl-cyclopropane-1-carboxamide

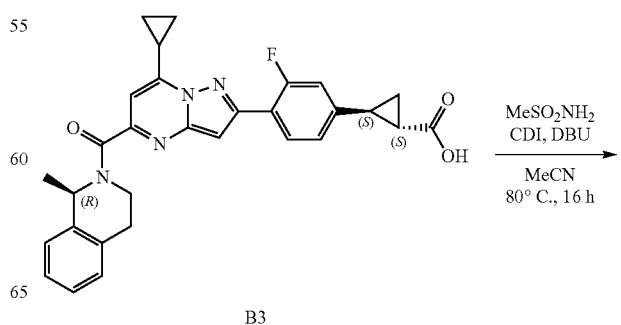

B3

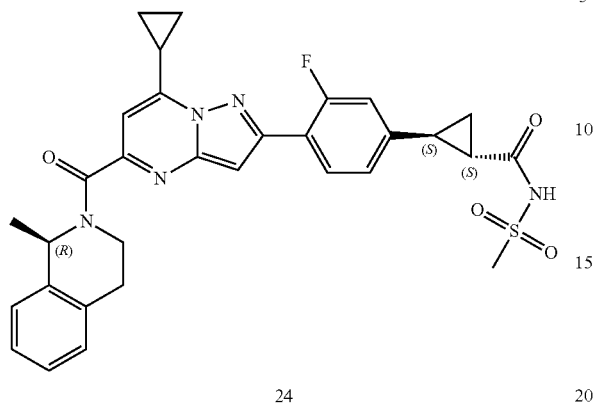

24

A mixture of intermediate B3 (200 mg, 0.39 mmol) and CDI (63.5 mg, 0.39 mmol) in MeCN (4 mL) was stirred at rt for 2 h. DBU (87.8 µL, 0.59 mmol) and methanesulfonamide [3144-09-0] (55.9 mg, 0.59 mmol) were added. The reaction mixture was stirred at 80° C. for 16 h. Brine, a 1N aqueous solution of HCl and EtOAc were added. The layers were separated and the aqueous phase was extracted with EtOAc (twice). The combined organic extracts were washed with a solution of water and brine (1:1), dried over MgSO$_4$, filtered and evaporated in vacuo. The crude mixture was purified by preparative LC (irregular SiOH, 15-40 µm, 12 g GraceResolv™, liquid injection (DCM), mobile phase gradient: DCM/MeOH from 100:0 to 98:2). The residue (206 mg) was crystallized from MeOH, filtered off and dried under high vacuum at 50° C. for 24 h to give compound 24 (192 mg, 83%) as a white solid.

Compound 25

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-(ethanesulfonyl)-cyclopropane-1-carboxamide

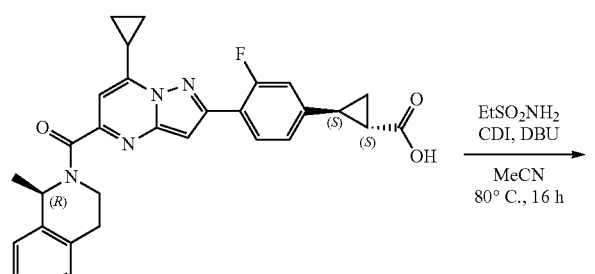

B3

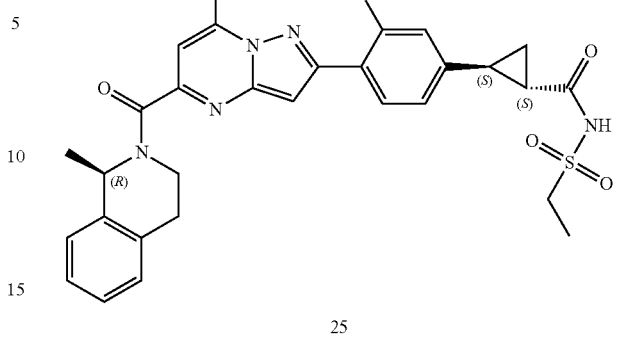

25

Compound 25 was synthesized from intermediate B3 and ethanesulfonamide [1520-70-3] according to the procedure reported for the synthesis of compound 24. Compound 25 (117 mg, 66%) was obtained as an off-white solid.

Compound 26

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-(2-methylpropanesulfonyl)-cyclopropane-1-carboxamide

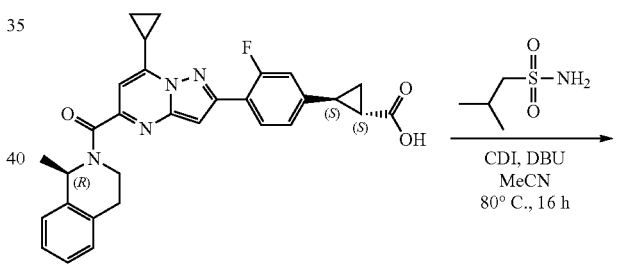

B3

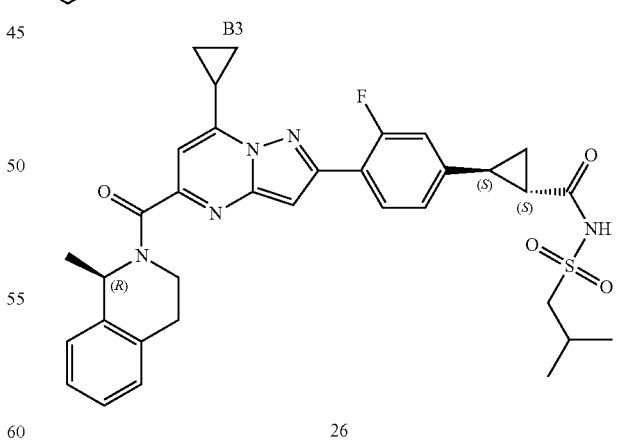

26

Compound 26 was synthesized from intermediate B3 and 2-methylpropane-1-sulfonamide [60199-80-6] according to the procedure reported for the synthesis of compound 24. Compound 26 (87 mg, 47%) was obtained as an off-white solid.

Compound 27

(1S,2S)—N-(Cyclopropanesulfonyl)-2-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-cyclopropane-1-carboxamide

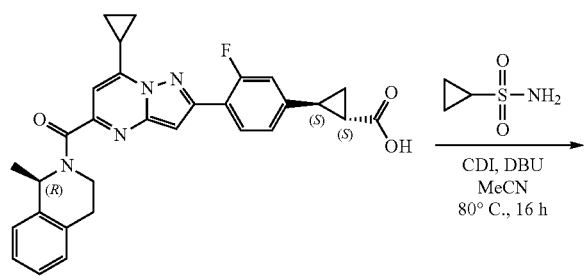

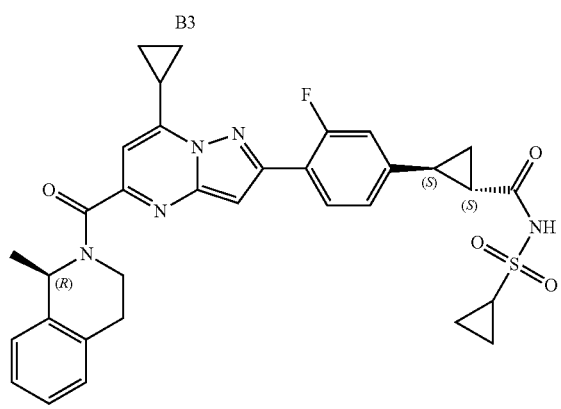

Compound 27 was synthesized from intermediate B3 and cyclopropanesulfonamide [154350-28-4] according to the procedure reported for the synthesis of compound 24. Compound 27 (106 mg, 59%) was obtained as an off-white solid.

Compound 28

(1S,2S)-2-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-N-methanesulfonyl-cyclopropane-1-carboxamide

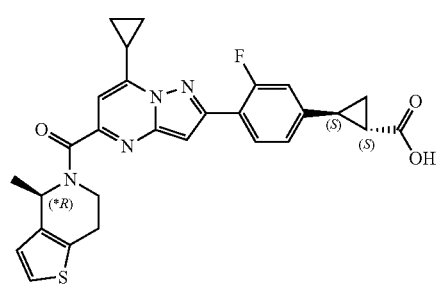

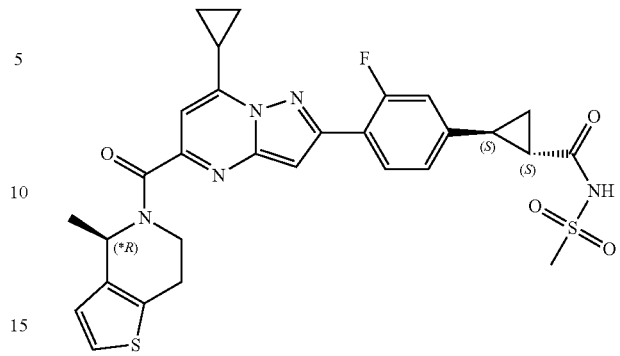

Compound 28 was synthesized from (1S,2S)-2-(4-{7-cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)cyclopropane-1-carboxylic acid [2035416-16-9] and methanesulfonamide [3144-09-0] according to the procedure reported for the synthesis of compound 24. Compound 28 (128 mg, 74%) was obtained as an off-white solid.

Compound 29

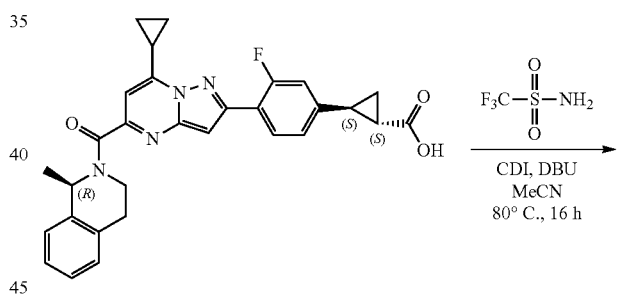

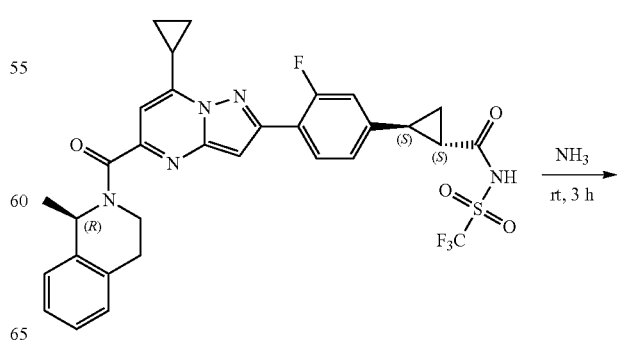

Intermediate B10

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-trifluoromethanesulfonylcyclopropane-1-carboxamide

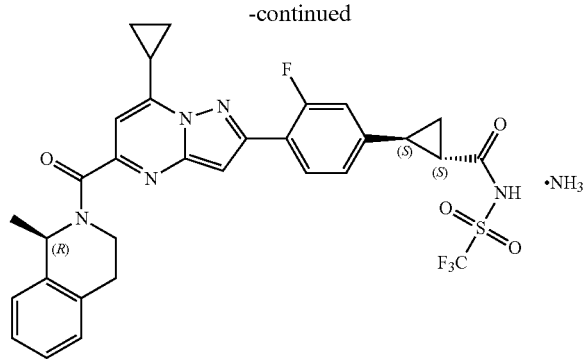

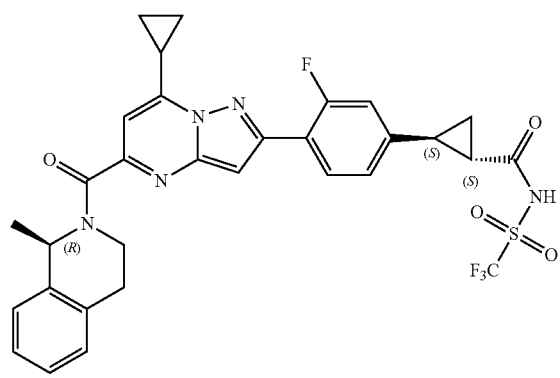

A mixture of intermediate B3 (150 mg, 0.29 mmol) and CDI (57.2 mg, 0.35 mmol) in MeCN (3 mL) was stirred at rt for 2 h. DBU (65.8 μL, 0.44 mmol) and trifluoromethanesulfonamide [421-85-2] (65.7 mg, 0.44 mmol) were added. The reaction mixture was stirred at 80° C. for 16 h. Brine, a 1N aqueous solution of HCl and DCM were added. The layers were separated and the aqueous phase was extracted with DCM (twice). The combined organic extracts were washed with a solution of water and brine (1:1), dried over MgSO₄, filtered and evaporated in vacuo. The crude mixture was purified by preparative LC (irregular SiOH, 15-40 μm, 12 g GraceResolv™, liquid injection (DCM), mobile phase gradient: DCM/(MeOH/AcOH 90:10) from 100:0 to 95:5). A second purification was performed by reverse phase (spherical C18, 25 μm, 40 g YMC-ODS-25, dry loading (Celite®), mobile phase gradient: (0.2% aq. NH₄HCO₃)/MeCN from 75:25 to 35:65). The fractions containing the product were combined and a 1N aqueous solution of HCl was added until pH 1. The layers were separated and the aqueous phase was extracted with DCM (3 times). The combined organic extracts were dried over MgSO₄, filtered and concentrated under reduced pressure to afford intermediate B10 (113 mg, 60%) as a white solid.

Compound 29

(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-trifluoromethane-sulfonylcyclopropane-1-carboxamide amine salt

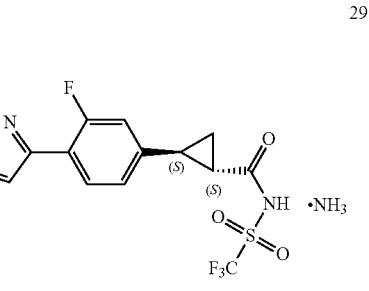

A solution of intermediate B10 (113 mg, 176 μmol) in ammonia (2.0 M in i-PrOH, 2 mL, 4.0 mmol) was stirred at rt for 3 h. The mixture was concentrated under reduced pressure. The residue was solubilized in MeOH (2 mL), extended with water (10 mL) and freeze-dried to give compound 29 (100 mg, 86%) as a white solid.

Compound 30

1-Cyclopropyl-3-[(1S,2R)-2-(4-{7-cyclopropyl-5-[(1R)-1-methyl-1,2,3,4-tetrahydro-isoquinoline-2-carbonyl]pyrazolo[1,5-a]pyrimidin-2-yl}-3-fluorophenyl)cyclopropyl]urea

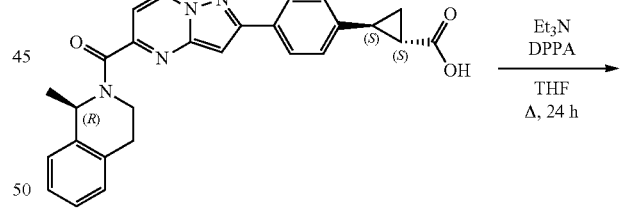

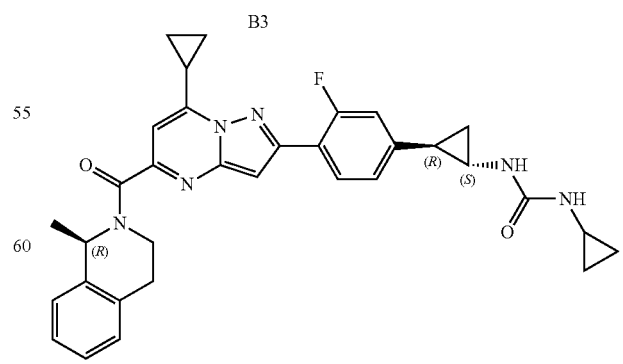

To a mixture of intermediate B3 (200 mg, 0.39 mmol) and Et₃N (55 μL, 0.40 mmol) in THF (3.2 mL) was added DPPA (127 μL, 0.59 mmol) dropwise. The reaction mixture was stirred under reflux for 2 h. After cooling down to rt, cyclopropylamine [765-30-0] (81 μL, 1.18 mmol) was added and the reaction mixture was stirred under reflux for an additional hour. Extra amount of cyclopropylamine (41 μL, 0.59 mmol) was added and the reaction mixture was stirred under reflux for 16 h. Et₃N (27 μL, 0.20 mmol) was added and the reaction mixture was stirred under reflux for 5 h. The reaction mixture was diluted with EtOAc, washed with a saturated aqueous solution of NaHCO₃, dried over MgSO₄, filtered and concentrated under reduced pressure. The crude mixture was purified by preparative LC (irregular SiOH, 15-40 μm, 12 g GraceResolv™, liquid injection (DCM), mobile phase gradient: heptane/(EtOAc/MeOH, 90:10) from 70:30 to 60:40). A second purification was carried out by reverse phase (spherical C18, 25 μm, 40 g YMC-ODS-25, dry loading (Celite®), mobile phase gradient: (0.2% aq. NH₄HCO₃)/MeCN from 60:40 to 0:100). The residue was taken up in Et₂O and evaporated in vacuo to give compound 30 (97 mg, 44%) as an off-white foam.

Compounds 31 and 32

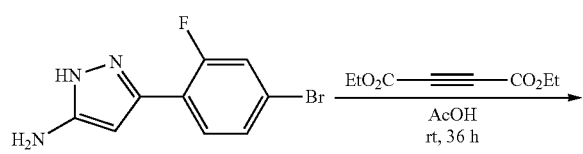

-continued

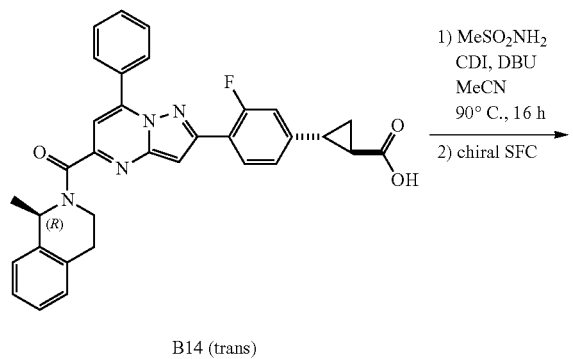

B14 (trans)

1) MeSO₂NH₂
CDI, DBU
MeCN
90° C., 16 h
2) chiral SFC

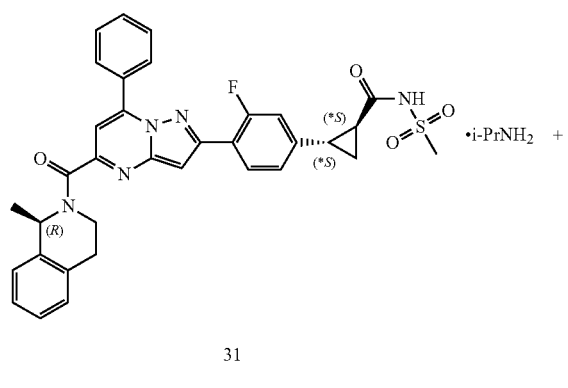

31

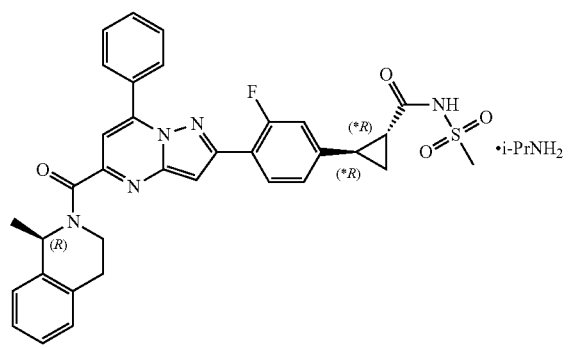

32

Intermediate C5

Ethyl 2-(4-bromo-2-fluorophenyl)-7-hydroxypyrazolo[1,5-a]pyrimidine-5-carboxylate

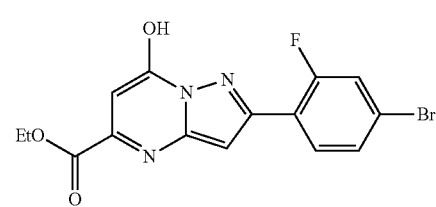

A mixture of 3-(4-bromo-2-fluorophenyl)-1H-pyrazol-5-amine [1135815-14-3] (15.0 g, 58.6 mmol) and diethyl acetylenedicarboxylate [762-21-0] (9.40 mL, 58.6 mmol) in acetic acid (110 mL) was stirred at rt for 36 h. The reaction mixture was diluted with EtOAc and heptane (30:60) (150 mL) and the mixture was stirred at rt for 30 min. The precipitate was filtered off and dried under vacuum to afford intermediate C5 (18.6 g, 84%).

Intermediate C6

Ethyl 2-(4-bromo-2-fluorophenyl)-7-chloropyrazolo[1,5-a]pyrimidine-5-carboxylate

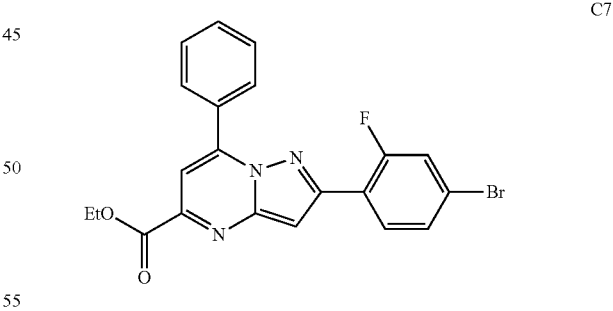

A mixture of intermediate C5 (15.0 g, 39.5 mmol) in phosphorous (V) oxychloride [10025-87-3] (147 mL) was stirred under reflux for 18 h. The solvent was evaporated to dryness. Water was added slowly and the mixture was stirred at 0° C. for 30 min. The precipitate was filtered off and dried under vacuum to afford intermediate C6 (15.3 g, 97%).

Intermediate C7

Ethyl 2-(4-bromo-2-fluorophenyl)-7-phenylpyrazolo[1,5-a]pyrimidine-5-carboxylate A mixture of intermediate C6 (1.00 g, 2.51 mmol) and 2-phenyl-4,4,5,5-tetramethyl-1,3,2-dioxaborolane [24388-23-6] (461 mg, 2.26 mmol) in THF (30 mL) was degassed with nitrogen for 10 min. [1,1'-Bis(diphenylphosphino)ferrocene]dichloropalladium(II), complex with dichloromethane (205 mg, 0.25 mmol) and potassium carbonate (2.0 M in H₂O, 3.8 mL, 7.53 mmol) were added and the reaction mixture was stirred at 70° C. for 18 h. The reaction mixture was diluted with water. The precipitate was filtered off and dried under vacuum at 60° C. to afford intermediate C7 (1.2 g, quant.).

Intermediate C8

Ethyl 2-(4-bromo-2-fluorophenyl)-7-phenylpyrazolo[1,5-a]pyrimidine-5-carboxylic acid

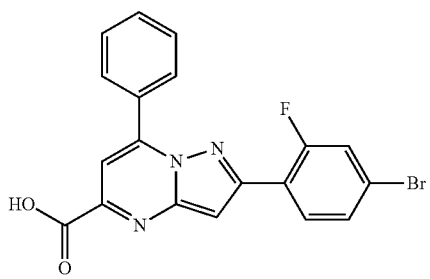

C8

A mixture of intermediate C7 (1.2 g, 2.73 mmol) and lithium hydroxide monohydrate (229 mg, 5.45 mmol) in THF (29 mL) and H₂O (0.7 mL) was stirred at rt for 18 h. The reaction mixture was diluted with water and acidified with a 3N aqueous solution of HCl. The mixture was extracted with DCM (twice). The combined organic extracts were dried over MgSO₄, filtered and the solvent was evaporated to afford intermediate C8 (1.0 g, 89%).

Intermediate B11

(1R)-2-[2-(4-Bromo-2-fluorophenyl)-7-phenylpyrazolo[1,5-a]pyrimidine-5-carbonyl]-1-methyl-1,2,3,4-tetrahydroisoquinoline

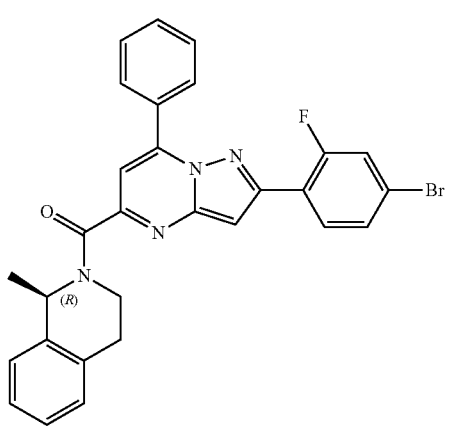

B11

DIPEA (1.27 mL, 7.29 mmol) and HATU (1.20 g, 3.15 mmol) were added to a mixture of (1R)-1-methyl-1,2,3,4-tetrahydroisoquinoline hydrochloride [84010-67-3] (535 mg, 2.91 mmol) and intermediate C8 (1.00 g, 2.43 mmol) in DMF (30 mL). The reaction mixture was stirred at rt for 48 h. The reaction mixture was poured out into water and the aqueous phase was extracted with EtOAc. The combined organic extracts were washed with brine, dried over MgSO₄, filtered and evaporated to dryness. The crude mixture was purified by flash chromatography over silica gel (40 g GraceResolv™, 15-40 μm, mobile phase gradient: heptane/EtOAc from 100:0 to 70:30). The pure fractions were collected and evaporated to dryness to afford intermediate B11 (680 mg, 52%).

Intermediate B12

Ethyl (2E)-3-(3-fluoro-4-{5-[(1R)-1-methyl-1,2,3,4-tetrahydroisoquinoline-2-carbonyl]-7-phenylpyrazolo[1,5-a]pyrimidin-2-yl}phenyl)prop-2-enoate

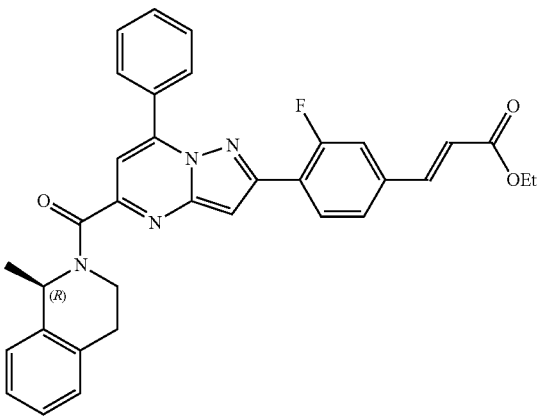

B12

A solution of intermediate B11 (0.36 g, 665 μmol) in MeCN (12 mL) was degassed with nitrogen for 10 min. Ethyl acrylate (0.36 mL, 3.33 mmol), palladium acetate (14.9 mg, 66.5 μmol), tri(o-tolyl)phosphine (30.4 mg, 99.7 μmol) and Et₃N (0.14 mL, 997 μmol) were added. The reaction mixture was heated at 120° C. using a single mode microwave (Biotage® Initiator EXP 60) with a power output ranging from 0 to 400 W for 20 min. The reaction mixture was poured out into a solution of water and DCM. The organic phase was separated (hydrophobic frit) and evaporated to dryness. The crude mixture was purified by flash chromatography over silica gel (cartridge 24 g, 15-40 μm, mobile phase gradient: heptane/EtOAc from 100:0 to 70:30). The pure fractions were collected and evaporated to dryness to afford intermediate B12 (240 mg, 64%).

Intermediate B13

Ethyl 2-(3-fluoro-4-{5-[(1R)-1-methyl-1,2,3,4-tetra-hydroisoquinoline-2-carbonyl]-7-phenylpyrazolo[1,5-a]pyrimidin-2-yl}phenyl)cyclopropane-1-carboxylate

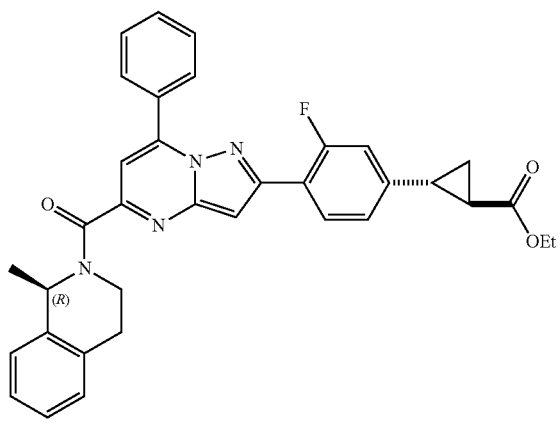

(trans)

Trimethylsulfoxonium iodide [1774-47-6] (104 mg, 0.47 mmol) was added to a solution of potassium tert-butoxide (52.8 mg, 0.47 mmol) in DMSO (6 mL). The reaction mixture was stirred at rt for 30 min. A solution of intermediate B12 (240 mg, 428 μmol) in DMSO (2 mL) was added and the reaction mixture was stirred at 60° C. for 18 h. The reaction mixture was poured out into water. The layers were separated and the aqueous phase was extracted with EtOAc. The combined organic extracts were washed with water and brine, dried over MgSO₄, filtered and evaporated to dryness. The crude mixture was purified by flash chromatography over silica gel (cartridge 24 g, 15-40 μm, mobile phase gradient: heptane/EtOAc from 100:0 to 70:30). The pure fractions were collected and evaporated to dryness to afford intermediate B13 (160 mg, 65%).

Intermediate B14

2-(3-Fluoro-4-{5-[(1R)-1-methyl-1,2,3,4-tetrahy-droisoquinoline-2-carbonyl]-7-phenylpyrazolo[1,5-a]pyrimidin-2-yl}phenyl)cyclopropane-1-carboxylic acid

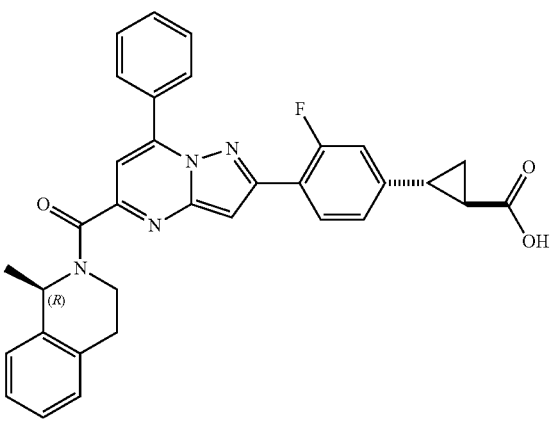

(trans)

Lithium hydroxide monohydrate (109 mg, 2.61 mmol) was added to a solution of intermediate B13 (300 mg, 522 μmol) in THF (4.3 mL) and H₂O (1.4 mL). The reaction mixture was stirred at rt for 24 h. Few drops of water were added followed by a 3N aqueous solution of HCl. The layers were separated and the aqueous phase was extracted with DCM (twice). The combined organic extracts were dried over MgSO₄, filtered and evaporated in vacuo to afford intermediate B14 (300 mg, quant).

Compounds 31 and 32

31: (1*S,2*S)-2-(3-Fluoro-4-{5-[(1R)-1-methyl-1,2,3,4-tetrahydroisoquinoline-2-carbonyl]-7-phenylpyrazolo[1,5-a]pyrimidin-2-yl}phenyl)-N-methanesulfonyl-cyclopropane-1-carboxamide; propan-2-amine salt 32: (1*R,2*R)-2-(3-Fluoro-4-{5-[(1R)-1-methyl-1,2,3,4-tetrahydroisoquinoline-2-carbonyl]-7-phenylpyrazolo[1,5-a]pyrimidin-2-yl}phenyl)-N-methanesulfonyl-cyclopropane-1-carboxamide; propan-2-amine salt

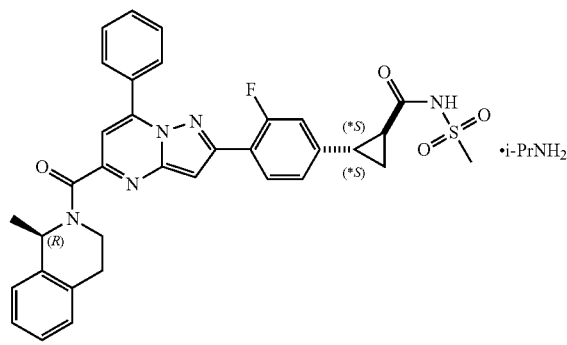

31

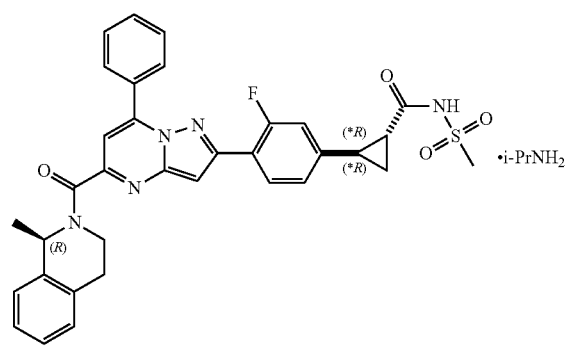

32

A mixture of intermediate B14 (300 mg, 0.55 mmol) and CDI (107 mg, 659 µmol) in MeCN (6 mL) was stirred at rt for 2 h. DBU (123 µL, 0.82 mmol) and methanesulfonamide [3144-09-0] (78.3 mg, 0.82 mmol) were added. The reaction mixture was stirred at 80° C. for 16 h. Brine, a 1N aqueous solution of HCl and DCM were added. The layers were separated and the aqueous phase was extracted with DCM (twice). The combined organic extracts were washed with a solution of water and brine (1:1), dried over MgSO₄, filtered and evaporated in vacuo (280 mg, 82%). The diastereoisomers were separated via chiral SFC (Stationary phase: Whelk-O1 (S,S) 5 µm 250*21.2 mm, Mobile phase: 40% CO₂, 60% (EtOH:DCM 80:20), 0.3% i-PrNH₂) to give compound 32 (114 mg, 37%) and compound 31 (115 mg, 38%) as yellow solids.

Compound 33

Methyl N-[(1S,2R)-2-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]carbamate

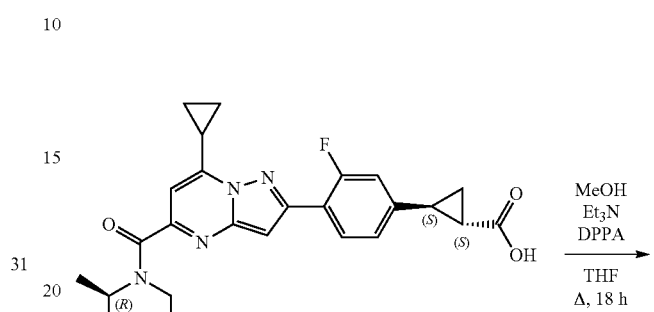

B3

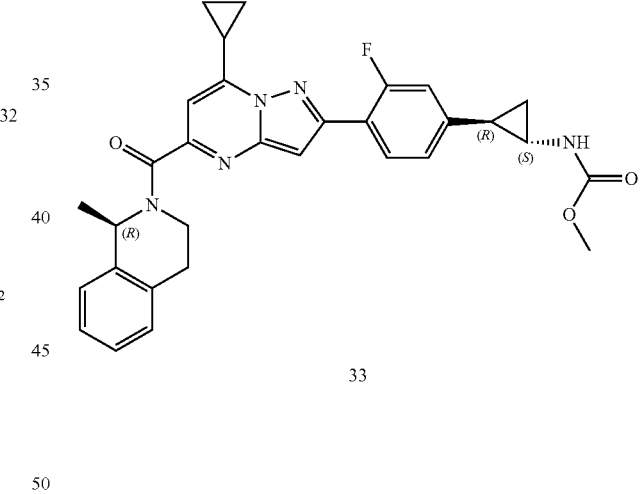

33

In a sealed tube DPPA (63.3 µL, 0.29 mmol) was added to a mixture of intermediate B3 (150 mg, 0.29 mmol) and Et₃N (53.1 µL, 0.38 mmol) in THF (3.5 mL) at rt. The reaction mixture was stirred under reflux for 1 h. MeOH (350 µL, 8.64 mmol) was added and the reaction mixture was stirred under reflux for 18 h. The reaction mixture was diluted with EtOAc, washed with a saturated aqueous solution of NaHCO₃, dried over MgSO₄, filtered and concentrated under reduced pressure. The crude mixture was purified by preparative LC (irregular SiOH, 15-40 µm, 12 g GraceResolv™, liquid injection (DCM), mobile phase gradient: heptane/EtOAc from 90:10 to 60:40). The residue was taken up in Et₂O, evaporated in vacuo (twice) and dried under high vacuum at 50° C. for 4 h to give compound 33 (69 mg, 44%) as a white solid.

Compound 34

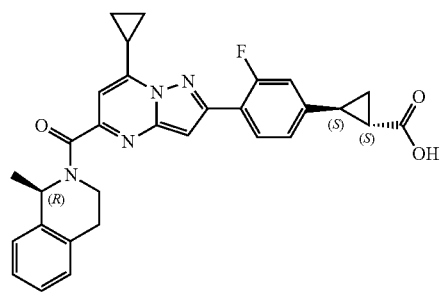

B3

Et₃N
DPPA
―――――→
t-BuOH
rt, 16 h
then 80° C.,
6 h

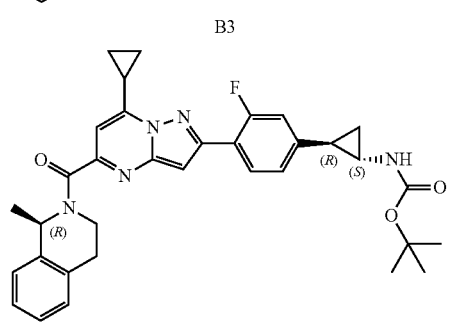

B15

TFA
―――→
DCM
0° C. to rt,
2 h

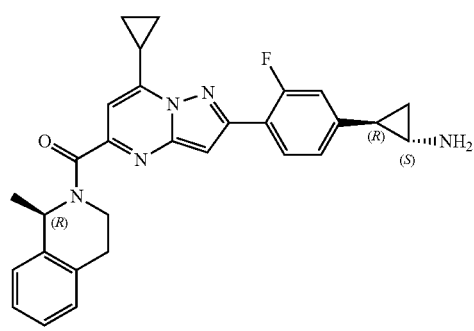

B16

AcCl
Et₃N
―――→
DCM,
rt, 24 h

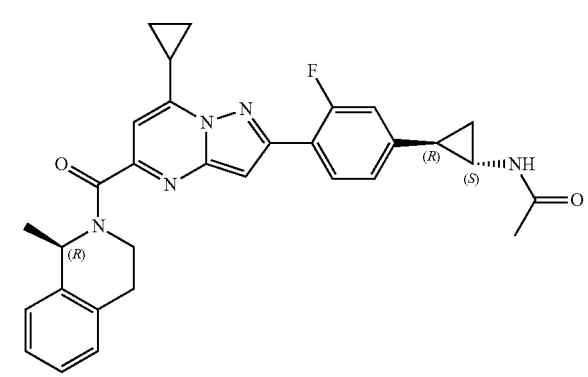

34

Intermediate B15

Tert-butyl N-[(1S,2R)-2-(4-{7-cyclopropyl-5-[(1R)-1-methyl-1,2,3,4-tetrahydroiso-quinoline-2-carbonyl]pyrazolo[1,5-a]pyrimidin-2-yl}-3-fluorophenyl)cyclopropyl]-carbamate

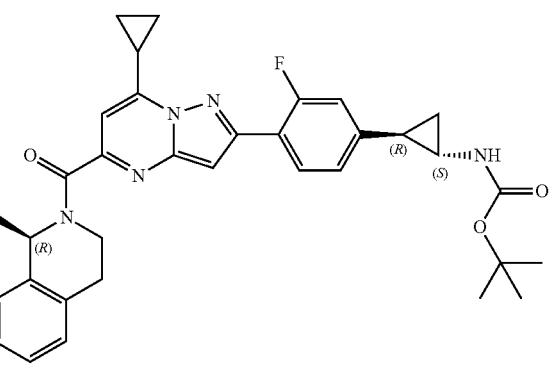

B15

A mixture of intermediate B3 (500 mg, 979 μmol), DPPA (232 μL, 1.08 mmol) and Et₃N (136 μL, 979 μmol) in t-BuOH (10 mL) was stirred at rt for 16 h and at 80° C. for 6 h. The reaction mixture was diluted with EtOAc, washed with a saturated aqueous solution of NaHCO₃, dried over MgSO₄, filtered and concentrated under reduced pressure. The crude mixture was purified by preparative LC (irregular SiOH, 15-40 μm, 12 g GraceResolv™, liquid injection (DCM), mobile phase gradient: heptane/EtOAc from 90:10 to 70:30) to afford intermediate B15 (331 mg, 58%) as a white solid.

Intermediate B16

(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropan-1-amine

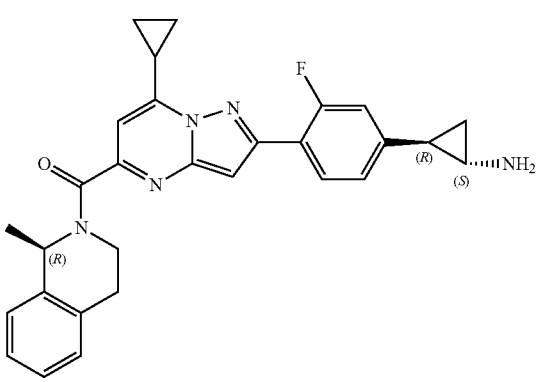

B16

To a solution of intermediate B15 (321 mg, 0.55 mmol) in DCM (7.4 mL) was added TFA (3.0 mL, 39.2 mmol) dropwise at 0° C. The reaction mixture was stirred at rt for 2 h. The reaction mixture was diluted with DCM and a 10% aqueous solution of K₂CO₃ was added. The mixture was filtered. The layers were separated and the aqueous phase was extracted with DCM (twice). The combined organic extracts were dried over MgSO₄, filtered and concentrated under reduced pressure to afford intermediate B16 (242 mg, 91%) as a white solid.

Compound 34

N-[(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]acetamide

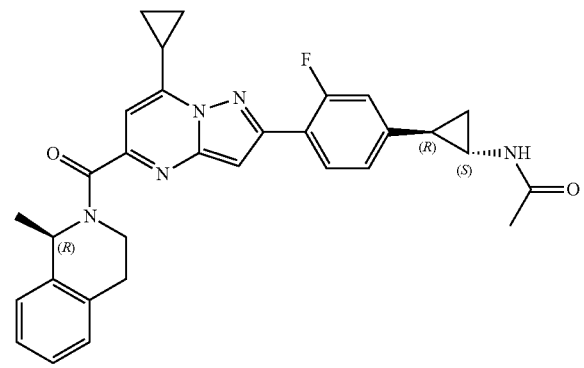

34

Acetyl chloride (39.3 µL, 0.55 mmol) was added to a mixture of intermediate B16 (242 mg, 0.50 mmol) and Et₃N (167 µL, 1.21 mmol) in DCM (1.3 mL). The reaction mixture was stirred at rt for 24 h. The reaction was quenched by the addition of an aqueous solution of NaHCO₃. The layers were separated and the aqueous phase was extracted with DCM. The combined organic extracts were dried over MgSO₄, filtered and the solvent was evaporated in vacuo. The crude mixture was purified by preparative LC (irregular SiOH, 15-40 µm, 12 g GraceResolv™, liquid injection (DCM), mobile phase gradient: DCM/MeOH from 100:0 to 98:2). The residue was crystallized from MeOH, filtered off and dried to give compound 34 (104 mg, 40%) as a white solid.

Compound 35

N-[(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]cyclopropane-carboxamide

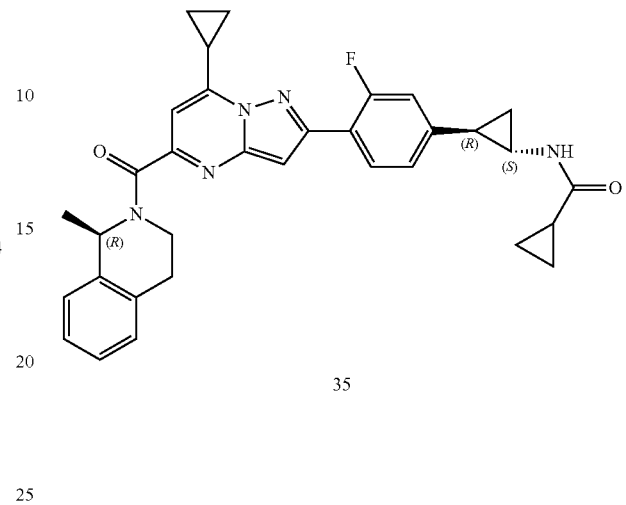

35

In a sealed tube DIPEA (178 µL, 1.02 mmol) was added to a solution of intermediate B16 (158 mg, 0.31 mmol) in DCM (4 mL) at 5° C. The mixture was stirred for 15 min and cyclopropanecarbonyl chloride [4023-34-1] (30.8 µL, 339 µmol) was added. The reaction mixture was stirred at rt overnight. The reaction mixture was poured out into cold water. The layers were separated and the aqueous phase was extracted with DCM. The combined organic extracts were dried over MgSO₄, filtered and evaporated to dryness. The crude mixture was purified by preparative LC (irregular SiOH, 15-40 µm, 12 g GraceResolv™, liquid injection (DCM), mobile phase gradient: DCM/EtOAc from 100:0 to 70:30). The residue was crystallized from MeOH, filtered off and dried under high vacuum at 50° C. for 3 h to give compound 35 (87 mg, 51%) as an off-white solid.

Compound 36

N-[(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]methanesulfonamide

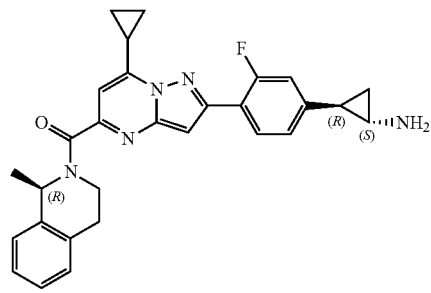 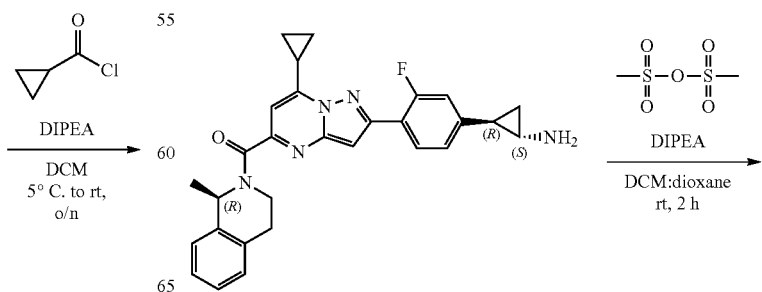

B16

B16

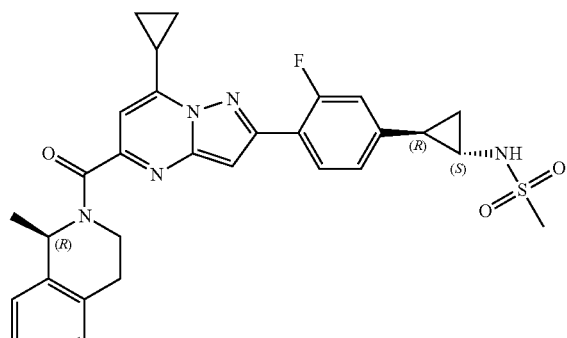

36

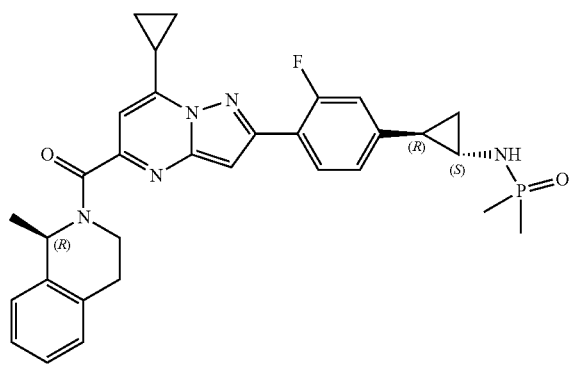

37

To a mixture of intermediate B16 (134 mg, 267 μmol) and DIPEA (55.2 μL, 0.32 mmol) in 1,4-dioxane (1 mL) under nitrogen was added a solution of methanesulfonic anhydride [7143-01-3] (51.2 mg, 0.29 mmol) in DCM (1 mL) dropwise. The reaction mixture was stirred at rt for 2 h. The reaction mixture was diluted with DCM and washed with a saturated aqueous solution of NaHCO₃, dried over MgSO₄, filtered and evaporated in vacuo. The crude mixture was purified by preparative LC (irregular SiOH, 15-40 μm, 12 g Grace®, dry loading (Celite®), mobile phase gradient: DCM/EtOAc from 100:0 to 95:5). The residue was crystallized from MeOH, filtered off and dried under high vacuum at 50° C. for 20 h to give compound 36 (68 mg, 45%) as a white solid.

Compound 37

(1R)-2-(7-Cyclopropyl-2-{4-[(1R,2S)-2-[(dimethylphosphoryl)amino]cyclopropyl]-2-fluorophenyl}pyrazolo[1,5-a]pyrimidine-5-carbonyl)-1-methyl-1,2,3,4-tetrahydroisoquinoline Dimethylphosphinic chloride [1111-92-8] (41.0 mg, 0.36 mmol) was added to a mixture of intermediate B16 (158 mg, 0.33 mmol), DIPEA (113 μL, 0.66 mmol) and DMAP (4.0 mg, 33.0 μmol) in anhydrous DCM (3.2 mL). The reaction mixture was stirred at rt for 2 h. An additional amount of dimethylphosphinic chloride (18.0 mg, 0.16 mmol) and DIPEA (57.0 μL, 0.33 mmol) were added and the reaction mixture was stirred for another 18 h. The reaction mixture was diluted with DCM, washed with a 10% aqueous solution of NaHCO₃, dried over MgSO₄, filtered and evaporated in vacuo. The crude mixture was purified by preparative LC (irregular SiOH, 15-40 μm, 12 g GraceResolv™, liquid injection (DCM), mobile phase gradient: DCM/MeOH from 100:0 to 96:4). The product was solubilized in MeCN (2 mL), extended with water (10 mL) and freeze-dried to give compound 37 (30 mg, 16%) as a white solid.

Compound 38

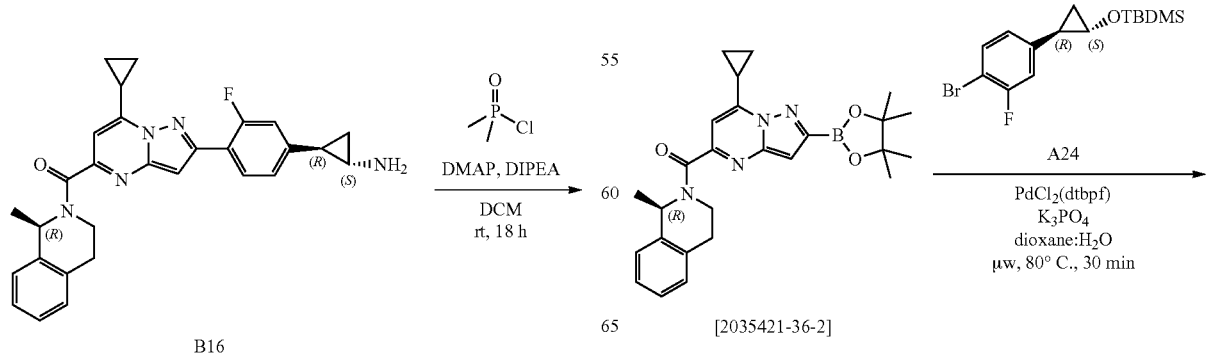

-continued

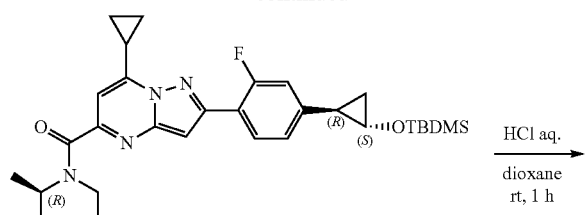

B17

Intermediate B17

(1R)-2-(2-{4-[(1R,2S)-2-[(Tert-butyldimethylsilyl)oxy]cyclopropyl]-2-fluorophenyl}-7-cyclopropylpyrazolo[1,5-a]pyrimidine-5-carbonyl)-1-methyl-1,2,3,4-tetrahydroisoquinoline

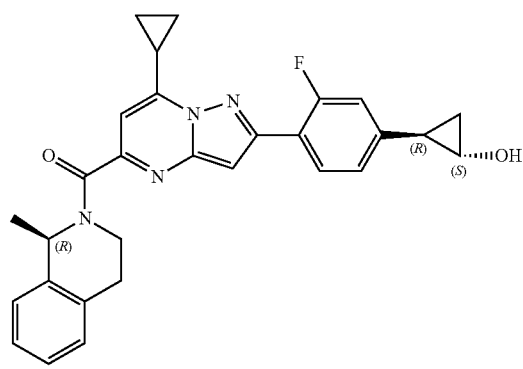

B17

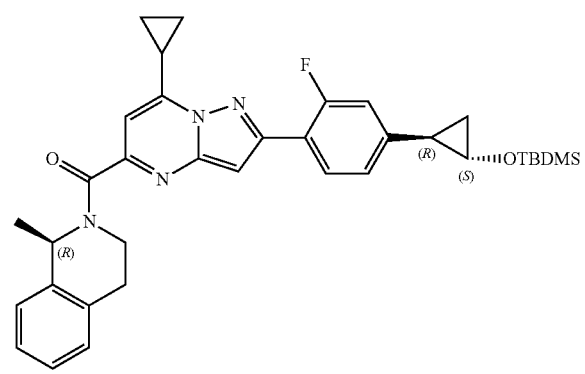

A sealed tube was charged with intermediate A24 (120 mg, 347 µmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (253 mg, 347 µmol, 63% purity), potassium phosphate tribasic (225 mg 1.06 mmol), 1,4-dioxane (3.5 mL) and H₂O (1.0 mL) and purged with nitrogen. [1,1'-Bis(di-tert-butylphosphino)ferrocene]-dichloropalladium(II) (11.3 mg, 17.4 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with water and EtOAc. The layers were separated and the aqueous phase was extracted with EtOAc (twice). The combined organic extracts were dried over MgSO₄, filtered and the solvent was evaporated in vacuo. The crude mixture was purified by preparative LC (irregular SiOH, 15-40 µm, 24 g GraceResolv™, liquid injection (DCM), mobile phase gradient: heptane/EtOAc from 99:1 to 40:60) to give intermediate B17 (170 mg, 82%).

Compound 38

(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropan-1-ol

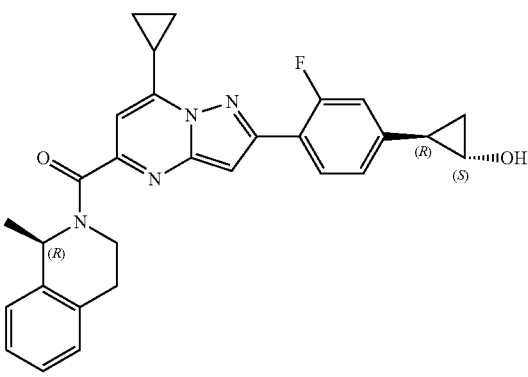

38

Hydrochloric acid (1.0 M in H₂O, 2.00 mL, 2.00 mmol) was added dropwise to a solution of intermediate B17 (140 mg, 235 µmol) in 1,4-dioxane (2 mL). The reaction mixture was stirred at rt for 1 h. The reaction mixture was concentrated under reduced pressure. The crude mixture was purified by preparative LC (irregular SiOH, 15-40 µm, 24 g GraceResolv™, liquid injection (DCM), mobile phase gradient: heptane/EtOAc from 99:1 to 40:60). The residue was taken up in acetone, evaporated in vacuo and dried under vacuum at 50° C. for 16 h to give compound 38 (88 mg, 88%) as a white solid.

Compound 39

(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl carbamate

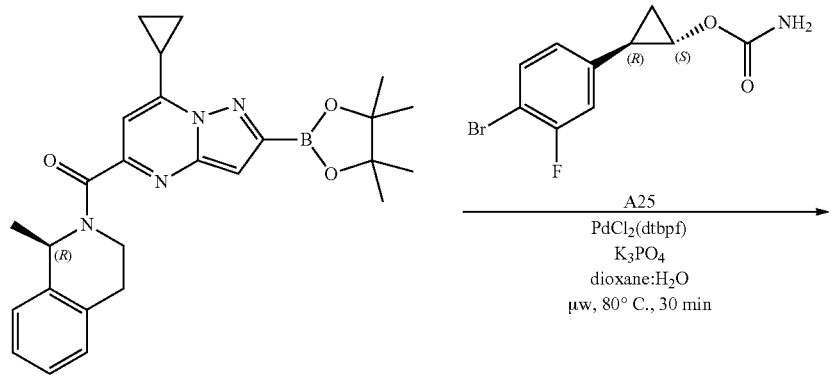

[2035421-36-2]

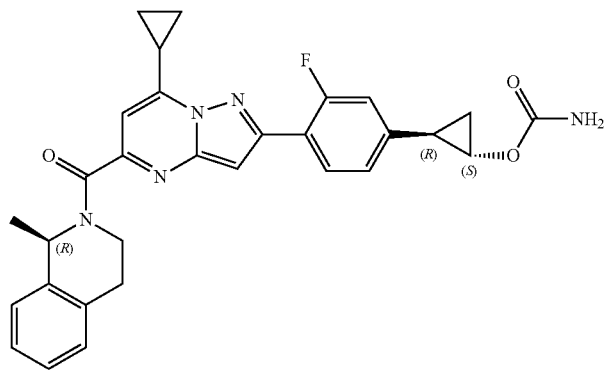

39

A sealed tube was charged with intermediate A25 (78.0 mg, 285 µmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (207 mg, 285 µmol, 63% purity), potassium phosphate tribasic (184 mg, 0.87 mmol), 1,4-dioxane (2.9 mL) and H₂O (0.8 mL) and purged with nitrogen. [1,1'-Bis(di-tert-butylphosphino)ferrocene]-dichloropalladium(II) (9.27 mg, 14.2 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with water and EtOAc. The layers were separated and the aqueous phase was extracted with EtOAc (twice). The combined organic extracts were dried over MgSO₄, filtered and the solvent was evaporated in vacuo. The crude mixture was purified by preparative LC (irregular SiOH, 15-40 µm, 12 g GraceResolv™, liquid injection (DCM), mobile phase gradient: heptane/EtOAc from 80:20 to 40:60). A second purification was carried out by preparative LC (spherical C18 25 µm, 40 g YMC-ODS-25, dry loading (Celite®), mobile phase gradient (0.2% aq. NH₄HCO₃)/MeCN from 60:40 to 0:100). The residue was taken up in EtOH, evaporated in vacuo and dried under vacuum at 50° C. for 16 h to give compound 39 (75 mg, 50%) as a white solid.

Compound 40

(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl N-methylcarbamate

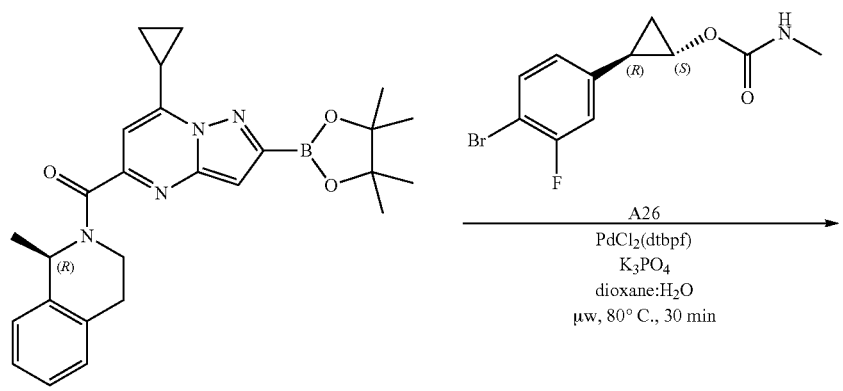

[2035421-36-2]

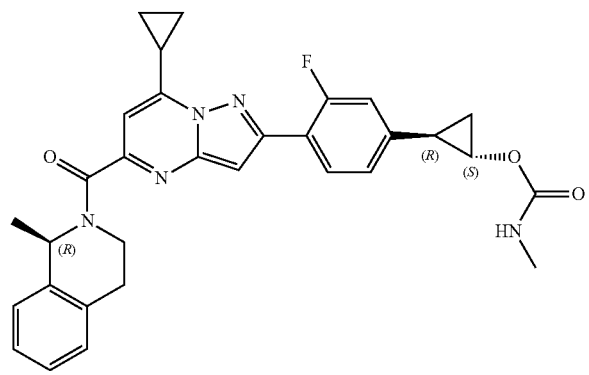

40

Compound 40 was synthesized from intermediate A26 and (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] according to the procedure reported for the synthesis of compound 39. Compound 40 (120 mg, 56%) was obtained as a white solid.

Compound 49

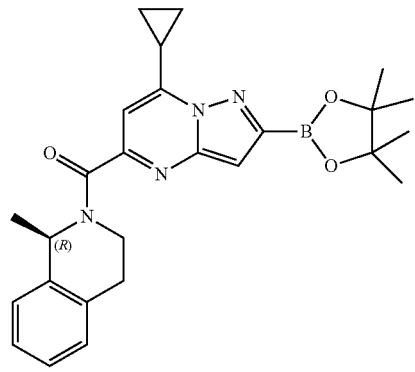

[2035421-36-2]

+

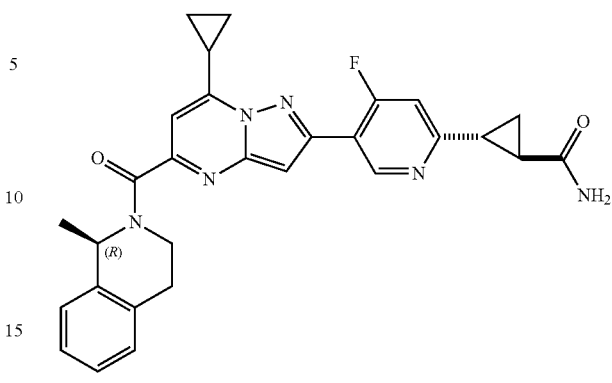

49 (trans)

Intermediate B18

Ethyl trans-2-(5-{7-cyclopropyl-5-[(1R)-1-methyl-1,2,3,4-tetrahydroisoquinoline-2-carbonyl]pyrazolo[1,5-a]pyrimidin-2-yl}-4-fluoropyridin-2-yl)cyclopropane-1-carboxylate

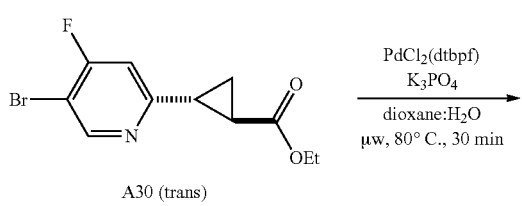

A30 (trans)

PdCl$_2$(dtbpf)
K$_3$PO$_4$
dioxane:H$_2$O
μw, 80° C., 30 min

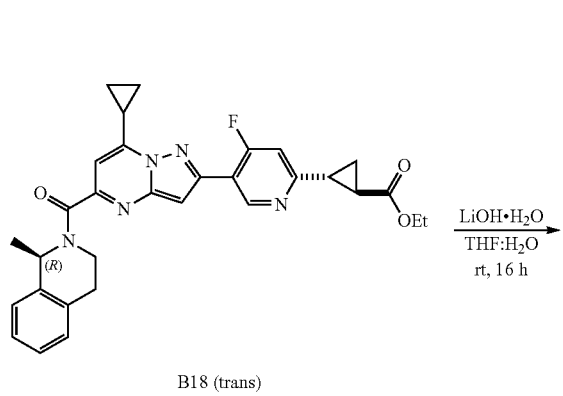

B18 (trans)

LiOH·H$_2$O
THF:H$_2$O
rt, 16 h

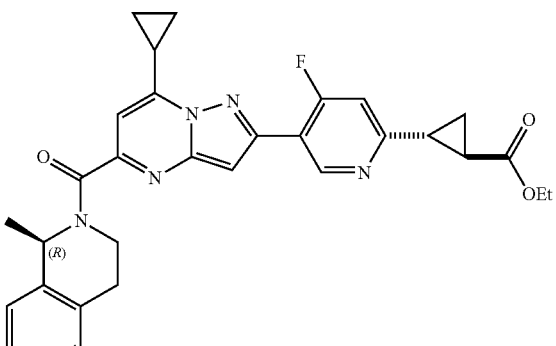

B18 (trans)

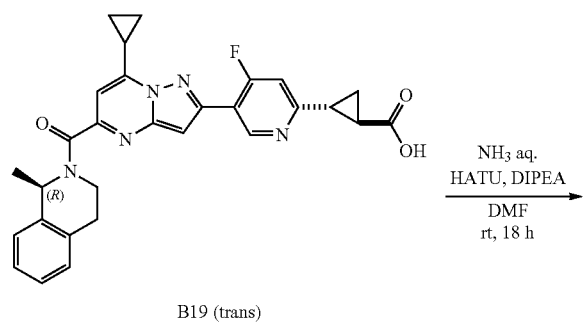

B19 (trans)

NH$_3$ aq.
HATU, DIPEA
DMF
rt, 18 h

A sealed tube was charged with intermediate A30 (111 mg, 385 μmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (285 mg, 385 μmol, 62% purity), potassium phosphate tribasic (245 mg, 1.16 mmol), 1,4-dioxane (2.7 mL) and H$_2$O (0.7 mL) and purged with nitrogen. [1,1'-Bis(di-tert-butylphosphino)ferrocene]dichloropalladium(II) (25.1 mg, 38.5 μmol) was added. The mixture was purged again with nitrogen and heated at 80° C. using a single mode microwave (Biotage® Initiator EXP 60) with a power output ranging from 0 to 400 W for 30 min. The reaction mixture was diluted with EtOAc. The organic phase was washed with brine, dried over MgSO₄, filtered and evaporated in vacuo. The crude mixture was purified by preparative LC (irregular SiOH, 30 μm, 24 g GraceResolv™, liquid injection (DCM), mobile phase gradient: heptane/EtOAc from 80:20 to 20:80) to afford intermediate B18 (182 mg, 88%).

Intermediate B19

Trans-2-(5-{7-Cyclopropyl-5-[(1R)-1-methyl-1,2,3,4-tetrahydroisoquinoline-2-carbonyl]pyrazolo[1,5-a]pyrimidin-2-yl}-4-fluoropyridin-2-yl)cyclopropane-1-carboxylic acid

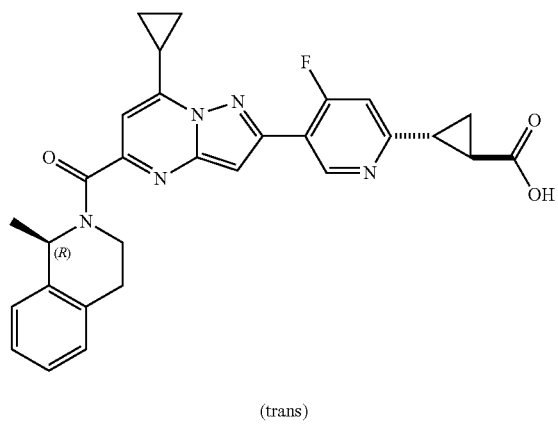

B19

(trans)

Lithium hydroxide monohydrate (42.0 mg, 1.00 mmol) was added to a solution of intermediate B18 (180 mg, 334 μmol) in THF (2.9 mL) and H₂O (0.9 mL). The reaction mixture was stirred at rt for 16 h. A 10% aqueous solution of KHSO₄ was added until pH 6 and the aqueous phase was extracted with EtOAc. The combined organic extracts were washed with water, dried over MgSO₄, filtered and concentrated in vacuo. The crude mixture was purified by preparative LC (irregular SiOH, 15-40 μm, 24 g GraceResolv™, liquid injection (DCM), mobile phase gradient: heptane/EtOAc/AcOH from 50:48.75:1.25 to 0:97.5:2.5). The residue was taken up in MeCN and the product was dried under vacuum at 50° C. for 16 h to afford intermediate B19 (140 mg, 82%).

Compound 49

Trans-2-(5-{7-Cyclopropyl-5-[(1R)-1-methyl-1,2,3,4-tetrahydroisoquinoline-2-carbonyl]pyrazolo[1,5-a]pyrimidin-2-yl}-4-fluoropyridin-2-yl)cyclopropane-1-carboxamide

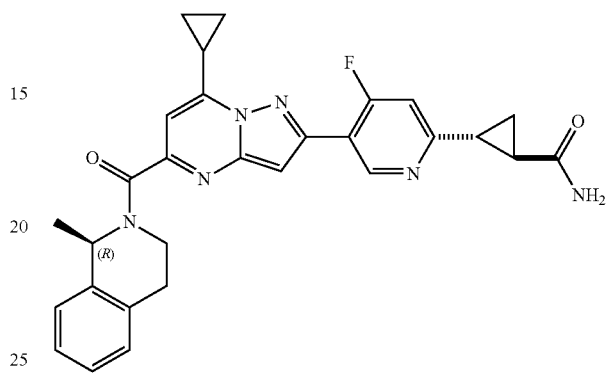

49

(trans)

A mixture of intermediate B19 (66.0 mg, 129 μmol), HATU (73.6 mg, 194 μmol) and DIPEA (66.7 μL, 387 μmol) in DMF (3.5 mL) was stirred at rt for 1 h. Ammonia (28% in H₂O, 43.6 μL, 645 μmol) was added and the reaction mixture was stirred at rt for 18 h. The reaction mixture was diluted with water and EtOAc. The layers were separated and the aqueous phase was extracted with EtOAc. The combined organic extracts were dried over MgSO₄, filtered and evaporated in vacuo. The crude mixture was purified by reverse phase (spherical C18 25 μm, 40 g YMC-ODS-25, dry loading (Celite®), mobile phase gradient: (0.2% aq. NH₄HCO₃/MeCN from 65:35 to 25:75) to give after freeze-drying (MeCN/H₂O) compound 49 (52 mg, 79%) as a white solid.

Compound 50

Trans-2-(5-{7-Cyclopropyl-5-[(1R)-1-methyl-1,2,3,4-tetrahydroisoquinoline-2-carbonyl]pyrazolo[1,5-a]pyrimidin-2-yl}-4-fluoropyridin-2-yl)-N-methanesulfonylcyclopropane-1-carboxamide

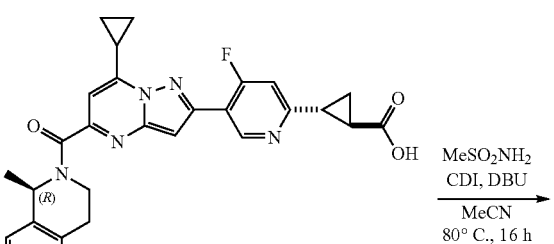

B19 (trans)

109
-continued

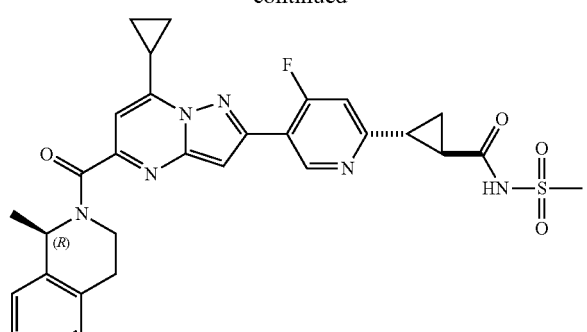

50 (trans)

A mixture of intermediate B19 (63.0 mg, 123 µmol) and CDI (30.0 mg, 185 µmol) in MeCN (1.2 mL) was stirred at rt for 2 h. DBU (36.8 µL, 246 µmol) and methanesulfonamide (23.4 mg, 246 µmol) were added. The reaction mixture was stirred at 80° C. for 16 h. Brine, a 1N aqueous solution of HCl and EtOAc were added. The layers were separated and the aqueous phase was extracted with EtOAc (twice). The combined organic extracts were washed with a solution of water and brine (1:1), dried over MgSO$_4$, filtered and evaporated in vacuo. The crude mixture was purified by preparative LC (irregular SiOH, 15-40 µm, 12 g GraceResolv™, liquid injection (DCM), mobile phase gradient: DCM/i-PrOH from 99:1 to 80:20) to give after freeze drying (MeCN/H$_2$O) compound 50 (55 mg, 76%).

Compound 51

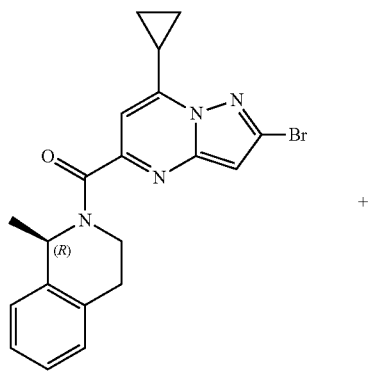

[2035421-35-1]

+

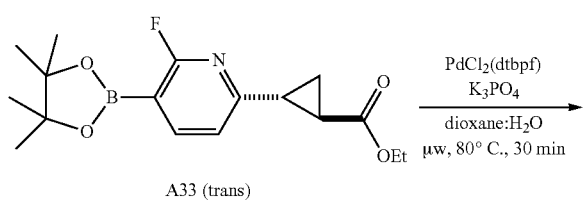

A33 (trans)

PdCl$_2$(dtbpf)
K$_3$PO$_4$
dioxane:H$_2$O
µw, 80° C., 30 min

110
-continued

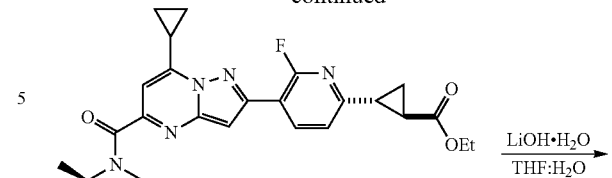

B20 (trans)

LiOH·H$_2$O
THF:H$_2$O
rt, 20 h

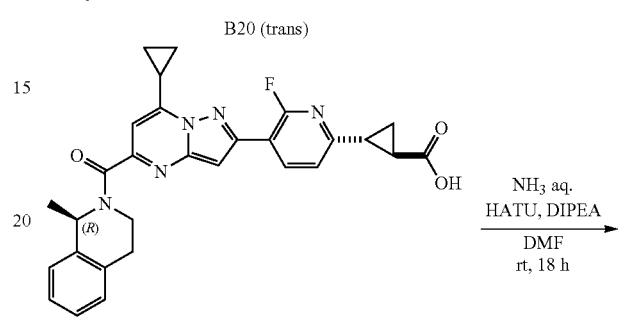

B21 (trans)

NH$_3$ aq.
HATU, DIPEA
DMF
rt, 18 h

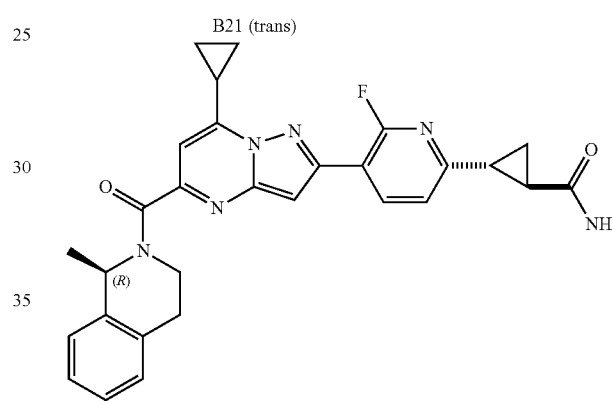

51 (trans)

Intermediate B20

Ethyl trans-2-(5-{7-cyclopropyl-5-[(1R)-1-methyl-1,2,3,4-tetrahydroisoquinoline-2-carbonyl]pyrazolo[1,5-a]pyrimidin-2-yl}-6-fluoropyridin-2-yl)cyclopropane-1-carboxylate

B20

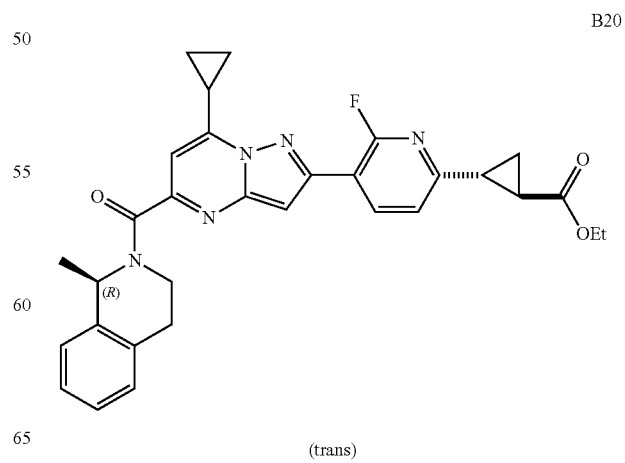

(trans)

A sealed tube was charged with (1R)-2-{2-bromo-7-cyclopropylpyrazolo[1,5-a]pyrimidine-5-carbonyl}-1-methyl-1,2,3,4-tetrahydroisoquinoline [2035421-35-1] (95.6 mg, 226 μmol), intermediate A33 (91.0 mg, 271 μmol), potassium phosphate tribasic (164 mg, 773 μmol), 1,4-dioxane (3.5 mL) and H₂O (1.2 mL) and purged with nitrogen. [1,1'-Bis(di-tert-butylphosphino)ferrocene]dichloropalladium(II) (16.2 mg, 24.9 μmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and water. The layers were separated and the organic phase was washed with brine, dried over MgSO₄, filtered and concentrated under reduced pressure. The crude mixture was purified by preparative LC (irregular SiOH, 15-40 μm, 12 g GraceResolv™, dry loading (Celite®), mobile phase gradient: heptane/EtOAc from 80:20 to 50:50) to afford intermediate B20 (128 mg, 98%) as an off-white solid.

Intermediate B21

Trans-2-(5-{7-Cyclopropyl-5-[(1R)-1-methyl-1,2,3,4-tetrahydroisoquinoline-2-carbonyl]pyrazolo[1,5-a]pyrimidin-2-yl}-6-fluoropyridin-2-yl)cyclopropane-1-carboxylic acid

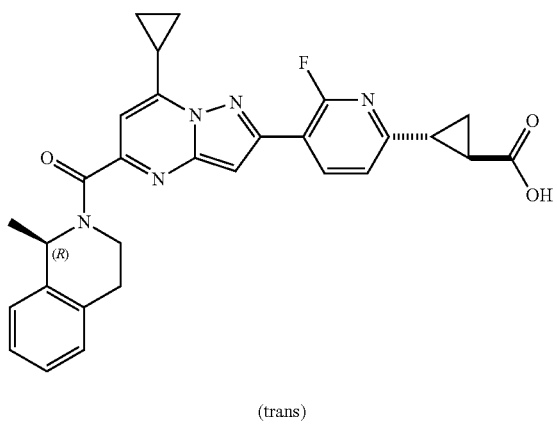

B21

(trans)

Lithium hydroxide monohydrate (24.6 mg, 587 μmol) was added to a solution of intermediate B20 (113 mg, 195 μmol) in H₂O (1.5 mL) and THF (3.2 mL). The reaction mixture was stirred at rt for 20 h. A 10% aqueous solution of KHSO₄ was added and the mixture was diluted with DCM. The layers were separated and the aqueous phase was extracted with DCM (twice). The combined organic extracts were washed with a solution of water and brine (1:1), dried over MgSO₄, filtered and evaporated in vacuo. The residue (102 mg) was taken up in toluene and evaporated (twice) to afford intermediate B21 (111 mg, 95%, 85% purity) as a yellowish gum.

Compound 51

Trans-2-(5-{7-Cyclopropyl-5-[(1R)-1-methyl-1,2,3,4-tetrahydroisoquinoline-2-carbonyl]pyrazolo[1,5-a]pyrimidin-2-yl}-6-fluoropyridin-2-yl)cyclopropane-1-carboxamide

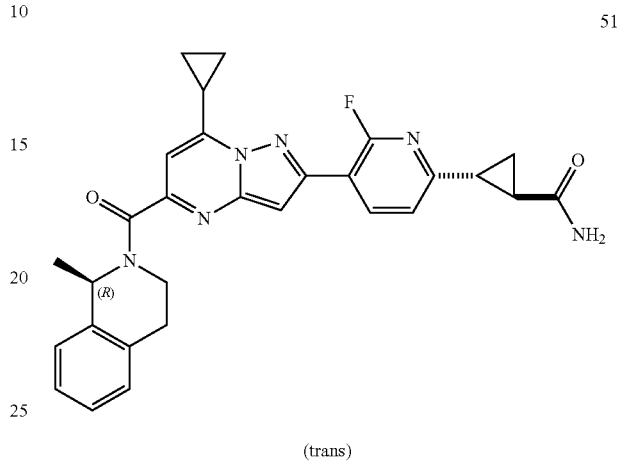

51

(trans)

A mixture of intermediate B21 (55.0 mg, 91.4 μmol, 85% purity), HATU (52.1 mg, 137 μmol) and DIPEA (50 μL, 0.29 mmol) in DMF (2.5 mL) was stirred at rt for 1 h. Ammonia (28% in H₂O, 32 μL, 474 μmol) was added and the reaction mixture was stirred at rt for 18 h. The reaction mixture was diluted with water and EtOAc. The layers were separated and the aqueous phase was extracted with EtOAc (twice). The combined organic extracts were washed with brine (3 times), dried over MgSO₄, filtered and evaporated in vacuo. The crude mixture was purified by preparative LC (irregular SiOH, 15-40 μm, 12 g GraceResolv™, liquid injection (DCM), mobile phase gradient: DCM/MeOH from 100:0 to 98:2). The residue (34 mg) was solubilized in MeOH (2 mL), extended with water (10 mL) and freeze-dried to give compound 51 (29 mg, 62%) as a white solid.

Compound 52

Trans-2-(5-{7-Cyclopropyl-5-[(1R)-1-methyl-1,2,3,4-tetrahydroisoquinoline-2-carbonyl]pyrazolo[1,5-a]pyrimidin-2-yl}-6-fluoropyridin-2-yl)-N-methanesulfonylcyclopropane-1-carboxamide

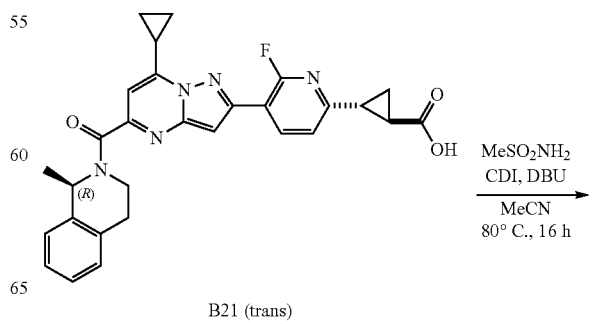

B21 (trans)

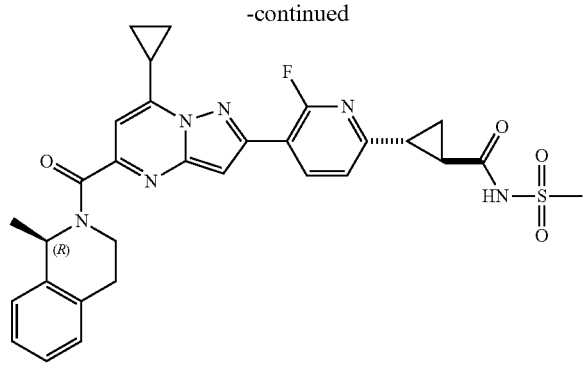

52 (trans)

A mixture of intermediate B21 (55.0 mg, 91.4 μmol, 85% purity) and CDI (17.8 mg, 0.11 mmol) in MeCN (1 mL) was stirred at rt for 2 h. DBU (20.5 μL, 137 μmol) and methanesulfonamide (13.0 mg, 137 μmol) were added. The reaction mixture was stirred at 80° C. for 16 h. Brine, a 1N aqueous solution of HCl and DCM were added. The layers were separated and the aqueous phase was extracted with DCM (twice). The combined organic extracts were washed with a solution of water and brine (1:1), dried over MgSO₄, filtered and evaporated in vacuo. The crude mixture was purified by preparative LC (irregular SiOH, 15-40 μm, 12 g GraceResolv™, liquid injection (DCM), mobile phase gradient: DCM/MeOH from 100:0 to 99:1). The residue was crystallized from MeOH. The solid was filtered off and dried under high vacuum at 50° C. for 18 h. The product (40 mg) was solubilized in MeCN (2 mL), extended with water (10 mL) and freeze-dried. The residue (36 mg) was purified by reverse phase (spherical C18, 25 μm, 40 g YMC-ODS-25, dry loading (Celite®), mobile phase gradient: (0.2% aq. NH₄HCO₃/MeCN from 85:15 to 55:45) and freeze-dried to give compound 52 (26 mg, 48%) as a white solid.

B.2. Preparation of Compounds of Formula (I) with n=2

B.2.1. Synthesis of Intermediates

B.2.1.1. Synthesis of Intermediates D4 and D5

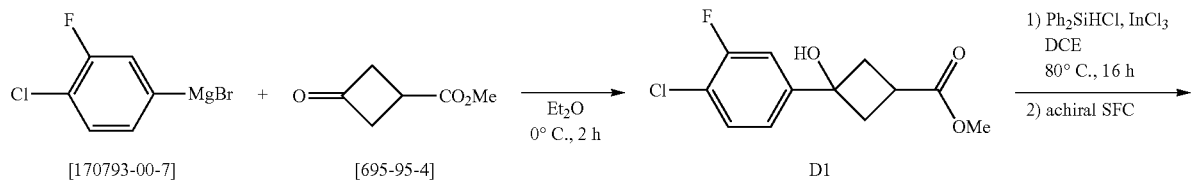

[170793-00-7]    [695-95-4]    D1

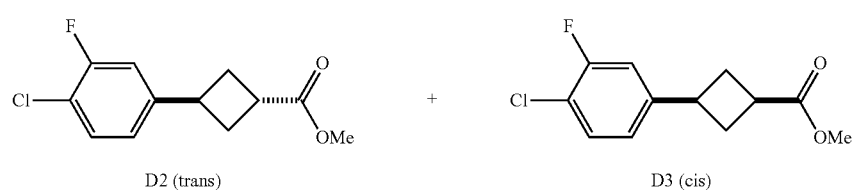

D2 (trans)    D3 (cis)

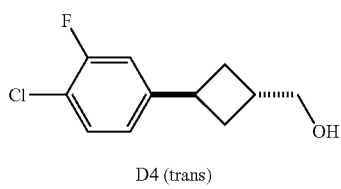    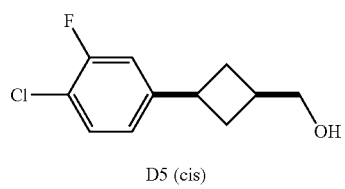

D4 (trans)    D5 (cis)

Intermediate D1

Methyl 3-(4-chloro-3-fluorophenyl)-3-hydroxycyclobutane-1-carboxylate

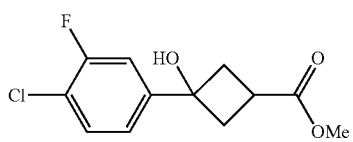

4-Chloro-3-fluorophenylmagnesium bromide [170793-00-7] (0.5 M in THF, 13.6 mL, 6.83 mmol) was added to a solution of methyl 3-oxocyclobutanecarboxylate [695-95-4] (0.74 mL, 7.04 mmol) in Et$_2$O (70 mL) at 0° C. The reaction mixture was stirred at 0° C. for 2 h. A saturated aqueous solution of NH$_4$Cl was added and the mixture was diluted with EtOAc. The layers were separated and the organic phase was washed with water, dried over MgSO$_4$ and concentrated in vacuo to afford intermediate D1 (1.47 g, 83%) as a yellow oil.

Intermediates D2 and D3

D2: Methyl trans-3-(4-chloro-3-fluorophenyl)cyclobutane-1-carboxylate

D3: Methyl cis-3-(4-chloro-3-fluorophenyl)cyclobutane-1-carboxylate

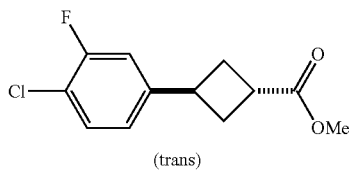

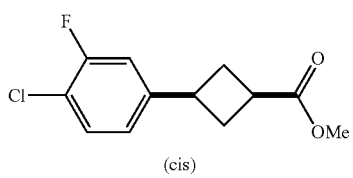

Diphenylchlorosilane (2.30 mL, 11.7 mmol) was added to a mixture of intermediate D1 (1.47 g, 5.68 mmol) and indium chloride (65.2 mg, 295 μmol) in DCE (8 mL). The reaction mixture was stirred at 80° C. for 16 h. The mixture was poured out into a solution of EtOAc and water. The layers were separated and the aqueous phase was extracted with EtOAc. The combined organic extracts were dried over MgSO$_4$, filtered and evaporated in vacuo. The crude mixture was purified by preparative LC (regular SiOH, 15-30 μm, 40 g Interchim®, dry loading (SiOH), mobile phase gradient: heptane/EtOAc from 100:0 to 50:50) to afford intermediate D3 (266 mg, 19%) and two fractions A (268 mg) and B (536 mg) as a mixture of diastereoisomers. Fraction B was purified by preparative LC (Stationary phase: irregular bare silica 150 g, mobile phase: heptane/EtOAc 95:5) to afford a mixture of diastereoisomers (210 mg). The residue was combined with fraction A and the mixture was purified via achiral SFC (Stationary phase: Chiralpak IG 5 μm 250*20 mm, Mobile phase: 95% CO$_2$, 5% MeOH) to give intermediate D2 (300 mg, 22%) and intermediate D3 (67 mg, 5%) as colorless oils.

Intermediate D4

[trans-3-(4-Chloro-3-fluorophenyl)cyclobutyl]methanol

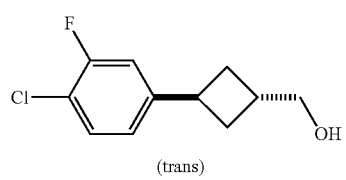

Lithium aluminium hydride (1.0 M in THF, 0.95 mL, 0.95 mmol) was added dropwise to a solution of intermediate D2 (225 mg, 927 μmol) in THF (9 mL) at 0° C. The reaction mixture was stirred at 0° C. for 3 h. The reaction was quenched by the careful addition of water (32 μL) at 0° C. followed by a 3M aqueous solution of NaOH (32 μL) and water (64 μL). The mixture was subsequently diluted with EtOAc. A solution of Rochelle salt was added and the layers were separated. The organic phase was washed with brine, dried over MgSO$_4$, filtered and concentrated to dryness to afford intermediate D4 (286 mg, quant. 70% purity) as a colorless oil.

Intermediate D5

[cis-3-(4-Chloro-3-fluorophenyl)cyclobutyl]methanol

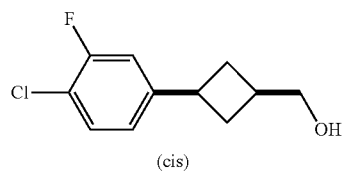

Intermediate D5 was synthesized from intermediate D3 according to the procedure reported for the synthesis of intermediate D4. Intermediate D5 (221 mg, quant.) was obtained as a colorless oil.

B.2.1.2. Synthesis of Intermediates D7 and D8

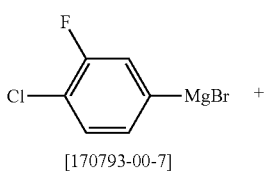

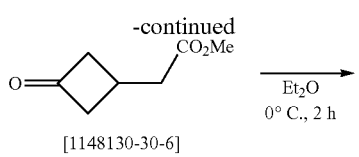

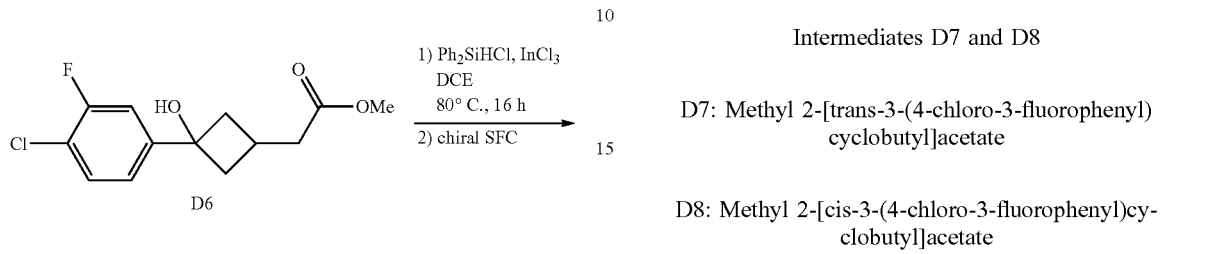

Intermediate D6

Methyl 2-[3-(4-chloro-3-fluorophenyl)-3-hydroxycyclobutyl]acetate

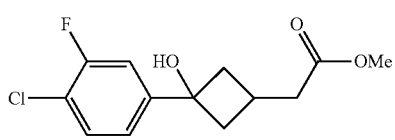

4-Chloro-3-fluorophenylmagnesium bromide [170793-00-7] (13.7 mL, 6.83 mmol) was added to a solution of methyl 2-(3-oxocyclobutyl)acetate [1148130-30-6] (1.00 g, 7.04 mmol) in Et$_2$O (70 mL) at 0° C. The reaction mixture was stirred at 0° C. for 2 h. A saturated aqueous solution of NH$_4$Cl was added and the mixture was diluted with EtOAc. The layers were separated and the organic phase was washed with water, dried over MgSO$_4$ and concentrated in vacuo. The crude mixture was purified by preparative LC (regular SiOH, 15-30 μm, 40 g GraceResolv™, dry loading (SiOH), mobile phase gradient: heptane/EtOAc from 90:10 to 50:50) to afford intermediate D6 (1.15 g, 61%) as a colorless oil.

Intermediates D7 and D8

D7: Methyl 2-[trans-3-(4-chloro-3-fluorophenyl)cyclobutyl]acetate

D8: Methyl 2-[cis-3-(4-chloro-3-fluorophenyl)cyclobutyl]acetate

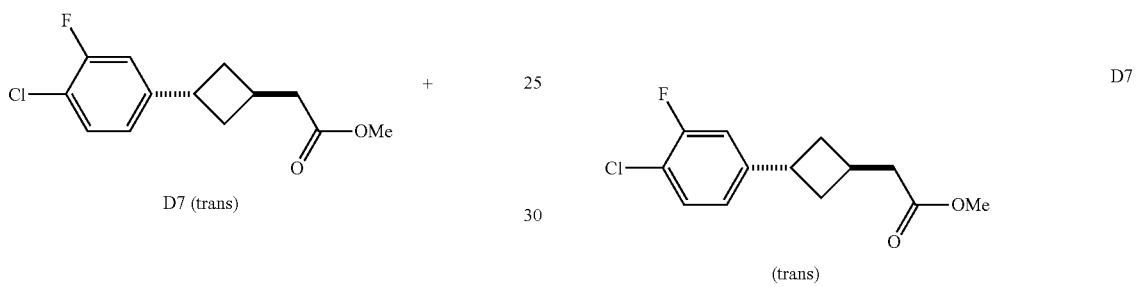

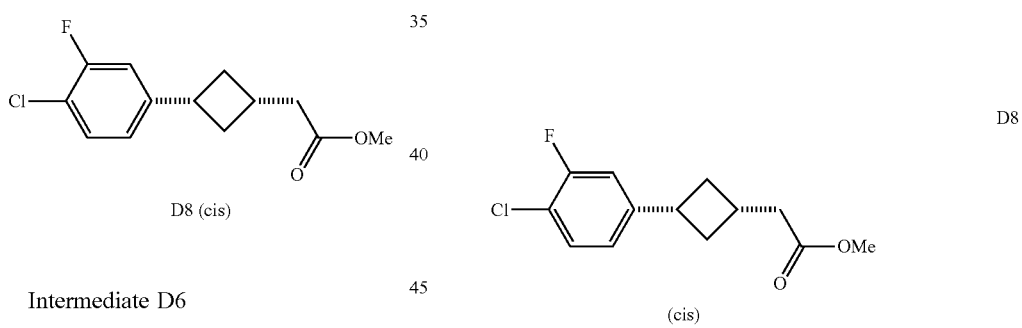

Diphenylchlorosilane (1.70 mL, 8.65 mmol) was added to a mixture of intermediate D6 (1.15 g, 4.22 mmol) and indium chloride (48.4 mg, 219 μmol) in DCE (6 mL). The reaction mixture was stirred at 80° C. for 16 h. The resulting mixture was poured out into a solution of EtOAc and water. The layers were separated and the aqueous phase was extracted with EtOAc. The combined organic extracts were dried over MgSO$_4$, filtered and evaporated in vacuo. The crude mixture was purified by preparative LC (regular SiOH, 15-30 μm, 80 g Interchim®, dry loading (SiOH), mobile phase gradient: heptane/EtOAc from 100:0 to 50:50). The diastereoisomers (684 mg) were separated by chiral SFC (Stationary phase: Lux Cellulose-2 5 μm 250*30 mm, Mobile phase: 96% CO$_2$, 4% i-PrOH) to afford intermediate D8 (313 mg, 29%) and intermediate D7 (158 mg, 15%).

B.2.2. Synthesis of Final Compounds

Compound 41

[trans-3-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]methanol

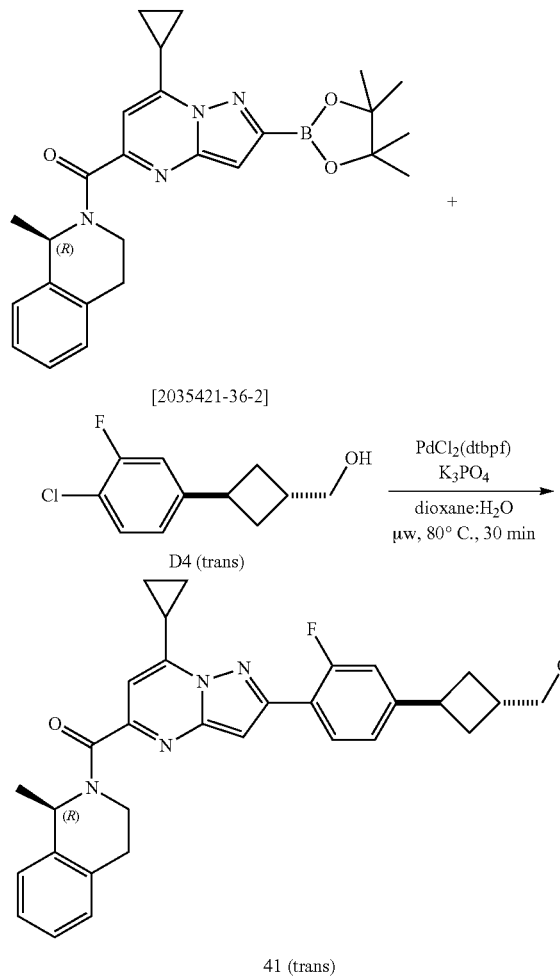

A sealed tube was charged with (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (392 mg, 582 μmol, 68% purity), intermediate D4 (200 mg, 932 μmol), potassium phosphate tribasic (551 mg, 2.60 mmol), 1,4-dioxane (7 mL) and H$_2$O (3 mL) and purged with nitrogen. [1,1'-Bis(di-tert-butylphosphino)ferrocene]dichloro-palladium(II) (84.7 mg, 130 μmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and water and filtered over a pad of Celite®. The filtrate was decanted and the organic phase was washed with brine (twice), dried over MgSO$_4$, filtered and concentrated to dryness. The crude mixture was purified by flash chromatography (irregular SiOH, 15-40 μm, 25 g GraceResolv™, dry loading (SiOH), mobile phase gradient: heptane/EtOAc from 90:10 to 20:80). The residue was purified by reverse phase (spherical C18, 25 μm, 40 g YMC-ODS-25, liquid injection (MeCN), mobile phase gradient: (0.2% aq. NH$_4$HCO$_3$)/MeCN, from 60:40 to 0:100). The fractions containing pure product were combined, concentrated to dryness and co-evaporated with MeCN to give compound 41 (116 mg, 39%) as a white foam.

Compound 42

[cis-3-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)cyclobutyl]methanol

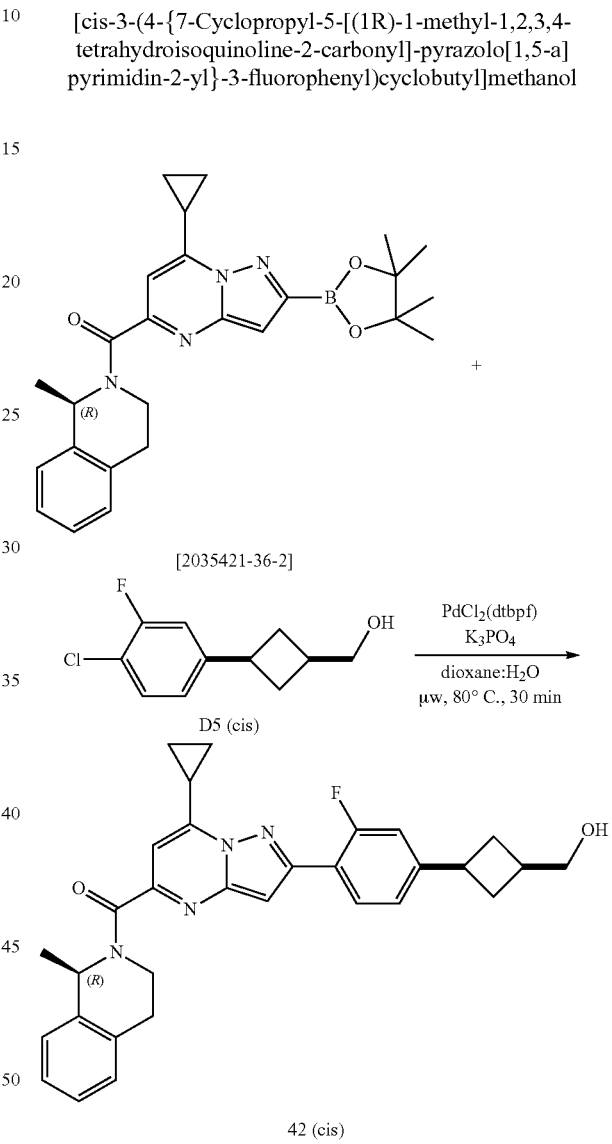

Compound 42 was synthesized from intermediate D5 and (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] according to the procedure reported for the synthesis of compound 41. The crude mixture was purified by flash chromatography (irregular SiOH, 15-40 μm, 25 g GraceResolv™, dry loading (SiOH), mobile phase gradient: heptane/EtOAc from 90:10 to 20:80). The residue was purified by reverse phase (spherical C18, 25 μm, 40 g YMC-ODS-25, liquid injection (MeCN), mobile phase gradient: (0.2% aq. NH$_4$HCO$_3$)/MeCN from 60:40 to 0:100). The fractions containing pure product were combined, concentrated to dryness, co-evaporated with MeCN and dried under high vacuum at 60° C. for 16 h to give compound 42 (154 mg, 52%) as a white solid.

Compound 43

[trans-3-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]methyl carbamate

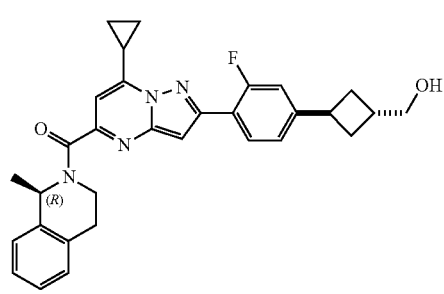

41 (trans)

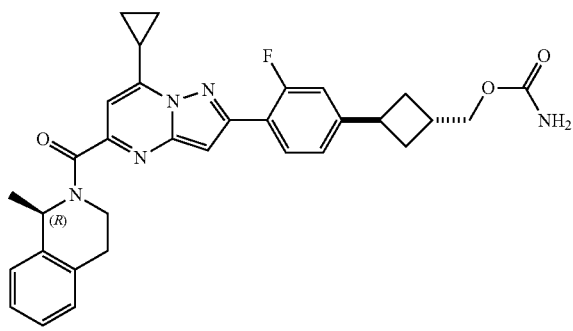

43 (trans)

Compound 44

[cis-3-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]methyl carbamate

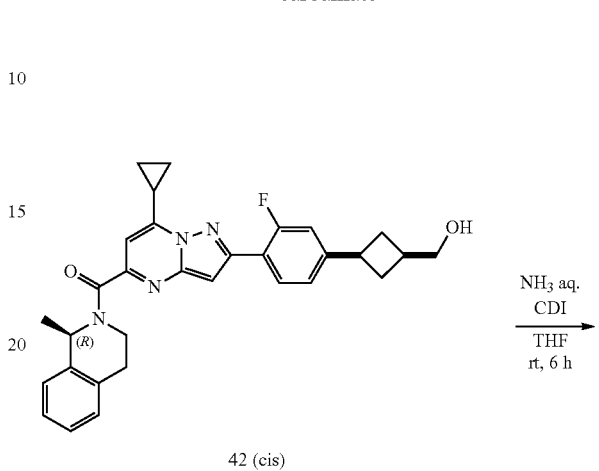

42 (cis)

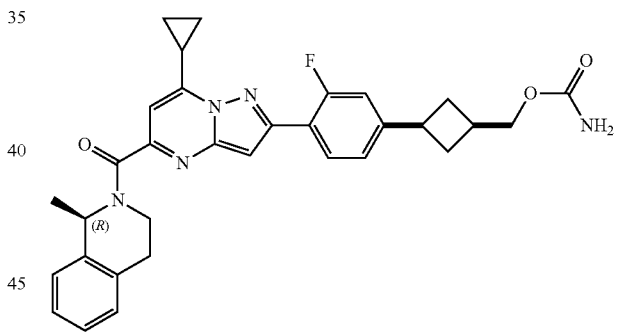

44 (cis)

CDI (41.9 mg, 259 µmol) was added to a solution of compound 41 (66.0 mg, 129 µmol) in THF (0.8 mL) and the reaction mixture was stirred at rt for 4 h. Ammonia (28% in H$_2$O, 484 µL, 7.16 mmol) was added and the reaction mixture was stirred at rt for 2 h. The reaction mixture was diluted with EtOAc. The layers were separated and the organic phase was washed with a saturated aqueous solution of NH$_4$Cl (twice), water and brine (twice), dried over MgSO$_4$, filtered and concentrated in vacuo. The residue was dried under high vacuum at 60° C. for 16 h to give compound 43 (42 mg, 59%) as a white solid.

CDI (46.4 mg, 286 µmol) was added to a solution of compound 42 (73.0 mg, 143 µmol) in THF (0.9 mL) and the reaction mixture was stirred at rt for 4 h. Ammonia (28% in H$_2$O, 535 µL, 7.92 mmol) was added and the reaction mixture was stirred at rt for 2 h. The reaction mixture was combined with another sample (20.0 mg, 39.2 µmol) and diluted with EtOAc, water and brine. The layers were separated and the organic phase was washed with a saturated aqueous solution of NH$_4$Cl (twice) and brine, dried over MgSO$_4$, filtered and concentrated in vacuo. The residue was taken up in MeCN (twice) and concentrated to dryness. The product was dried under high vacuum at 60° C. for 16 h to give compound 44 (52 mg, 52%) as a white solid.

Compound 45
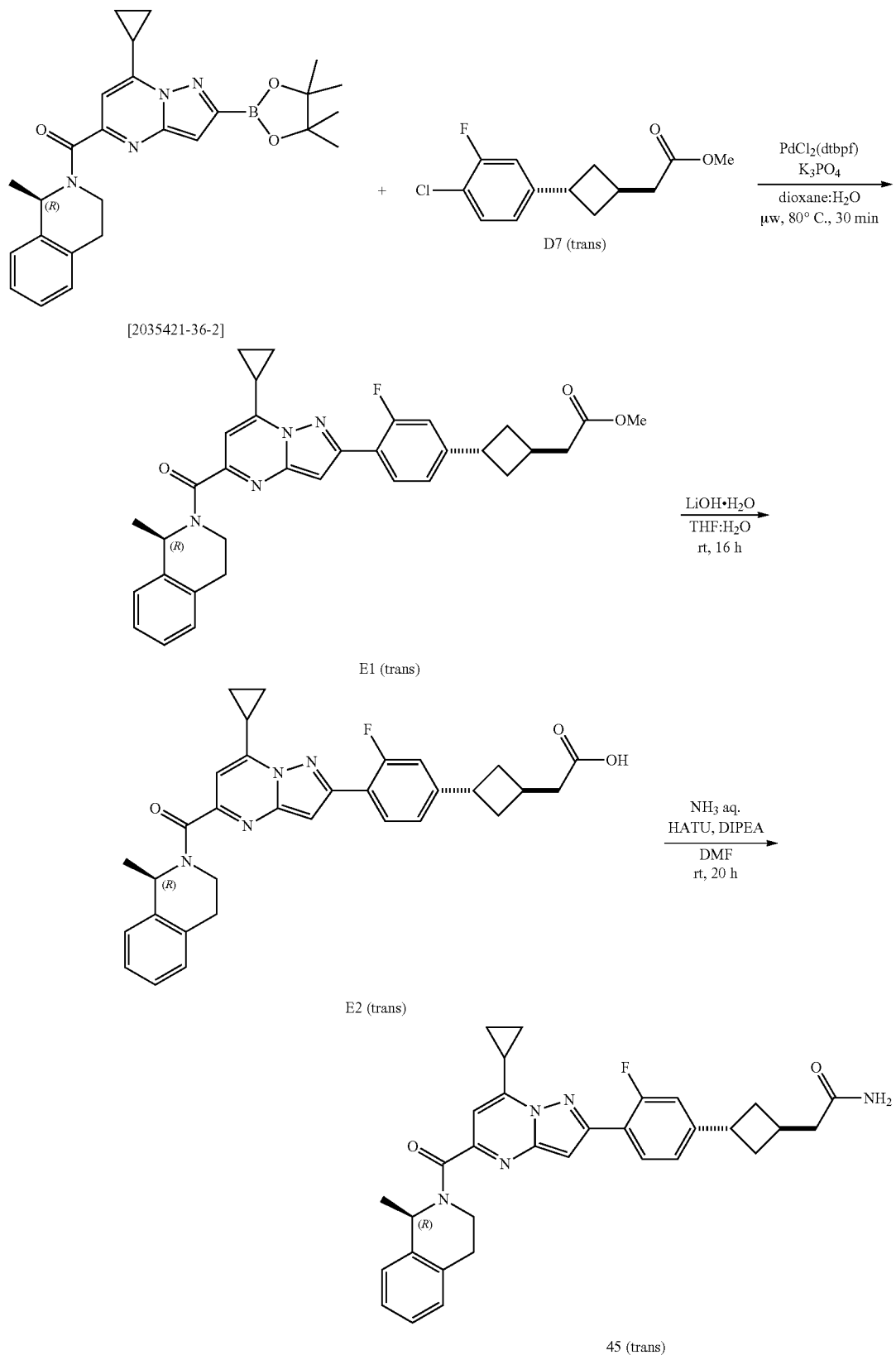

Intermediate E1

Methyl 2-[trans-3-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]acetate

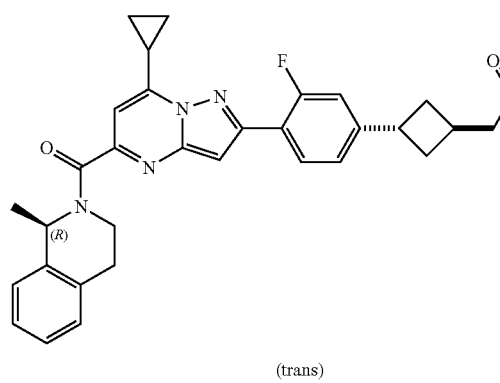

(trans)

A sealed tube was charged with (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (284 mg, 385 mmol, 62% purity), intermediate D7 (158 mg, 615 μmop, potassium phosphate tribasic (364 mg, 1.71 mmol), 1,4-dioxane (3.5 mL) and H₂O (1.4 mL) and purged with nitrogen. [1,1'-Bis(di-tert-butylphosphino)ferrocene]dichloro-palladium(II) (56.0 mg, 85.9 μmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc. The organic layer was washed with an aqueous solution of NaHCO₃ and brine, dried over MgSO₄, filtered and evaporated in vacuo. The crude mixture was purified by preparative LC (regular SiOH, 30 μm, 25 g Interchim®, liquid injection (DCM), mobile phase gradient: heptane/EtOAc from 90:10 to 30:70) to afford intermediate E1 (138 mg, 65%) as a yellow foam.

Intermediate E2

2-[trans-3-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]acetic acid

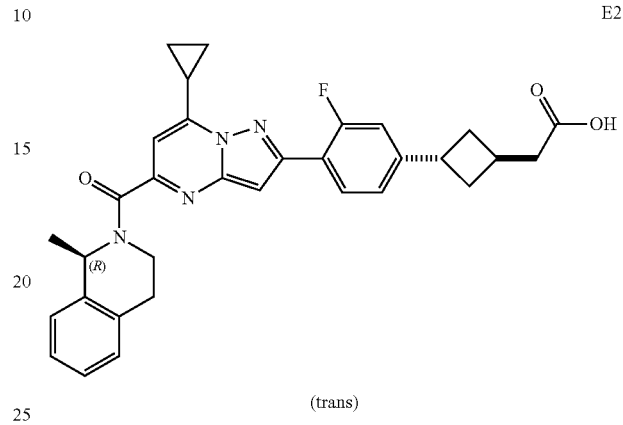

(trans)

Lithium hydroxide monohydrate (32.3 mg, 0.77 mmol) was added to a solution of intermediate E1 (138 mg, 0.25 mmol) in THF (2.2 mL) and H₂O (0.77 mL). The reaction mixture was stirred at rt for 16 h. A 10% aqueous solution of KHSO₄ was added until pH 3 and the mixture was diluted with EtOAc. The layers were separated and the organic phase was washed with brine and water (twice), dried over MgSO₄, filtered and concentrated to dryness to afford intermediate E2 (140 mg, 94%) as a yellow solid.

Compound 45

2-[trans-3-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]acetamide

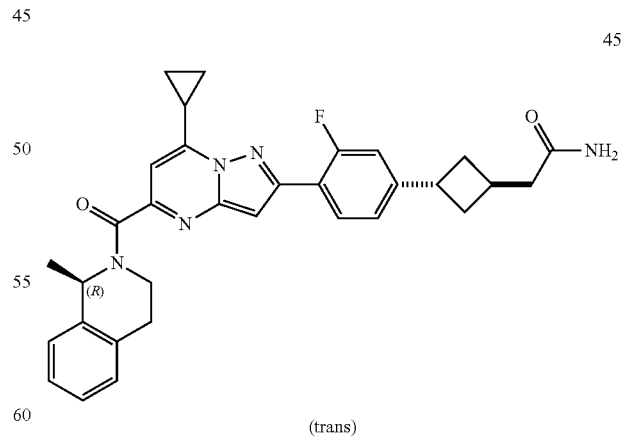

(trans)

In a screw cap vial HATU (66.7 mg, 175 μmol) was added to a mixture of intermediate E2 (70.0 mg, 117 μmol) and DIPEA (60.5 μL, 0.35 mmol) in DMF (1.1 mL). The reaction mixture was stirred at rt for 10 min. Ammonia (30% in H₂O, 221 μL, 3.51 mmol) was added and the reaction mixture was stirred at rt for 20 h. The reaction mixture was diluted with water, brine and EtOAc. The layers were separated and the organic phase was washed with brine (3 times), dried over MgSO$_4$, filtered and concentrated under reduced pressure. The crude mixture was purified by flash chromatography (irregular SiOH, 15-40 μm, 12 g GraceResolv™, liquid injection (DCM), mobile phase gradient: heptane/EtOAc from 50:50 to 0:100). The residue (30 mg) was diluted with EtOAc and sonicated. A precipitate was observed. The suspension was concentrated to dryness and dried under high vacuum at 60° C. for 16 h to give compound 45 (28 mg, 45%) as a white solid.

Compound 46

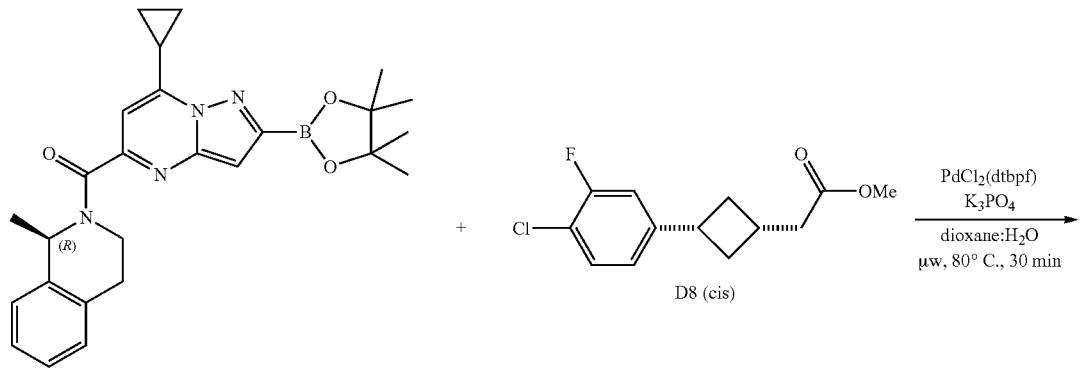

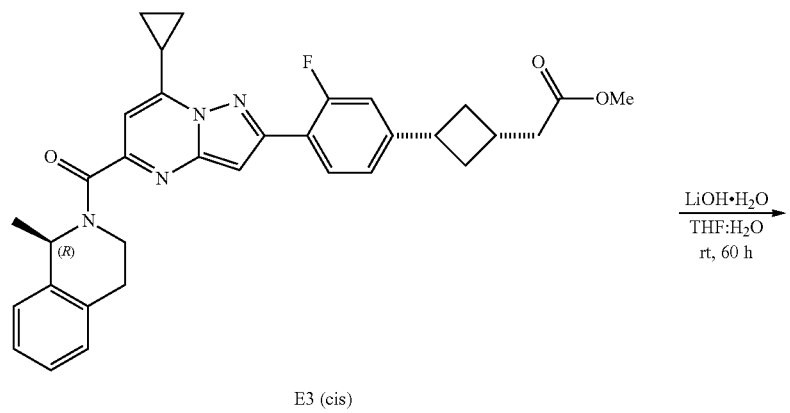

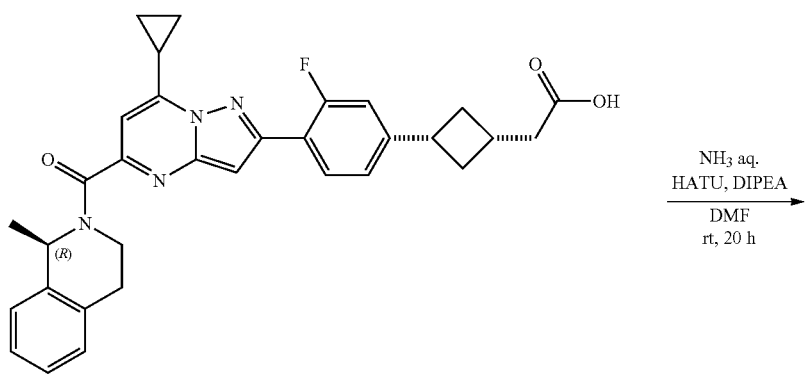

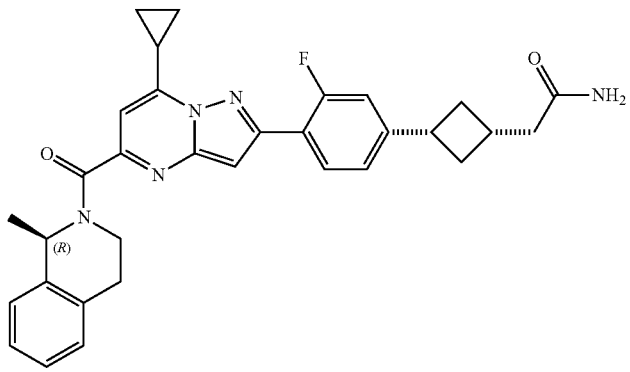

46 (cis)

Intermediate E3

Methyl 2-[cis-3-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]acetate

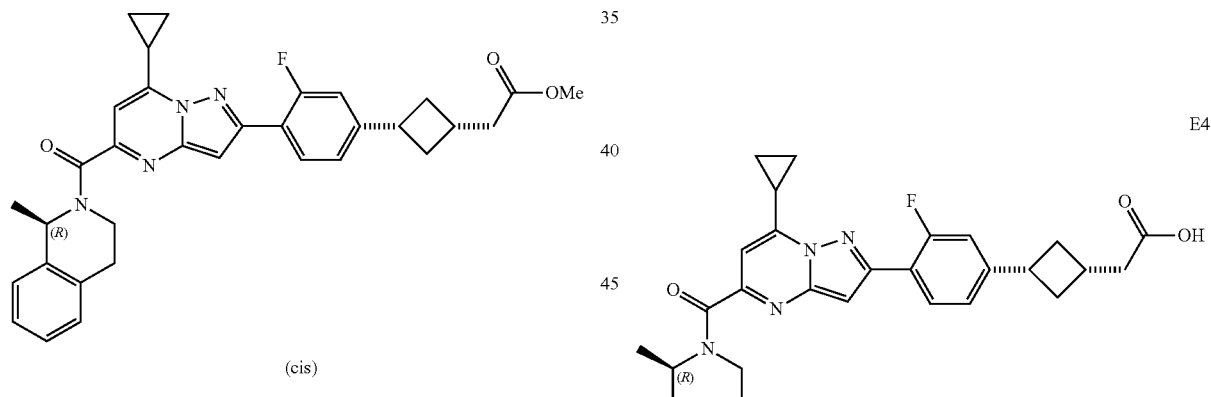

(cis)

E3

A sealed tube was charged with (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (563 mg, 762 μmol, 62% purity), intermediate D8 (313 mg, 1.22 mmol), potassium phosphate tribasic (721 mg, 3.40 mmol), 1,4-dioxane (10.4 mL) and H₂O (2.7 mL) and purged with nitrogen. [1,1'Bis(di-tert-butylphosphino)ferrocene]dichloro-palladium(II) (111 mg, 170 μmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and the organic phase was washed with an aqueous solution of NaHCO₃ and brine, dried over MgSO₄, filtered and evaporated in vacuo. The crude mixture was purified by preparative LC (regular SiOH, 30 μm, 25 g Interchim®, dry loading (SiOH), mobile phase gradient: heptane/EtOAc from 90:10 to 30:70) to afford intermediate E3 (227 mg, 54%) as a beige foam.

Intermediate E4

2-[cis-3-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]acetic acid

E4

(cis)

Lithium hydroxide monohydrate (52.7 mg, 1.26 mmol) was added to a solution of intermediate E3 (225 mg, 407 μmol) in THF (3.6 mL) and H₂O (1.2 mL). The reaction mixture was stirred at rt for 60 h. A 10% aqueous solution of KHSO₄ was added until pH 3 and the mixture was diluted with EtOAc. The layers were separated and the organic phase was washed with brine and water (twice), dried over MgSO₄, filtered and concentrated to dryness to afford intermediate E4 (221 mg, 93%) as a yellow solid.

Compound 46

2-[cis-3-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]acetamide

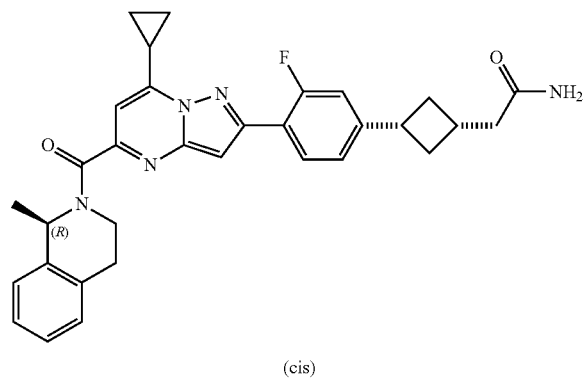

(cis)

In a screw cap vial HATU (107 mg, 282 µmol) was added to a mixture of intermediate E4 (110 mg, 188 µmol, 92% purity) and DIPEA (97.1 µL, 564 µmol) in DMF (1.8 mL). The reaction mixture was stirred at rt for 10 min. Ammonia (30% in $H_2O$, 356 µL, 5.64 mmol) was added and the reaction mixture was stirred at rt for 20 h. The reaction mixture was diluted with water, brine and EtOAc. The layers were separated and the organic phase was washed with brine (3 times), dried over $MgSO_4$, filtered and concentrated under reduced pressure. The crude mixture was purified by flash chromatography (irregular SiOH, 15-40 µm, 12 g GraceResolv™, liquid injection (DCM), mobile phase gradient: heptane/EtOAc from 50:50 to 0:100). The residue (61 mg) was diluted with $Et_2O$ and the solution was sonicated. A precipitate was formed. The suspension was concentrated to dryness and dried under high vacuum at 60° C. for 16 h to give compound 46 (58 mg, 57%) as a white solid.

Compound 47

N-methyl-2-[trans-3-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]acetamide

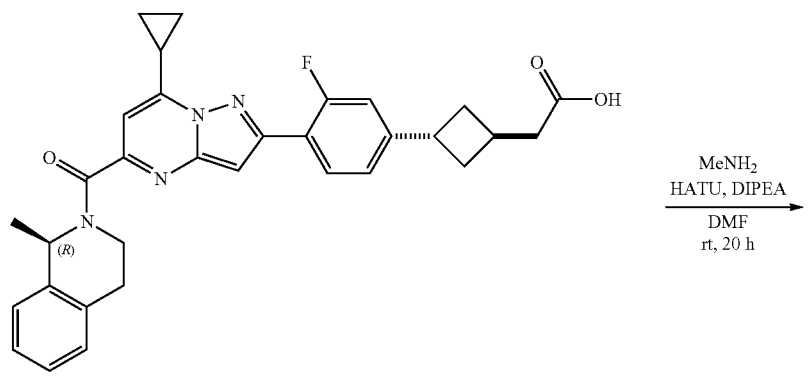

E2 (trans)

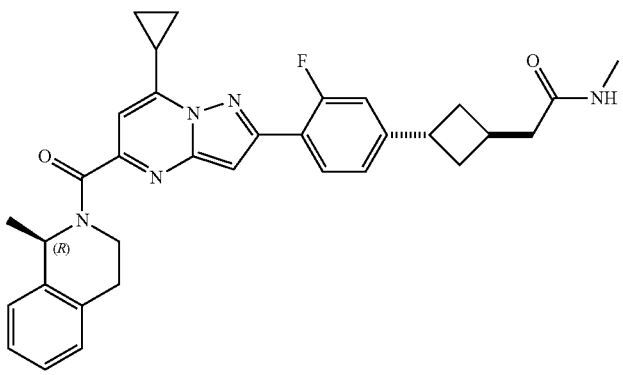

47 (trans)

In a screw cap vial HATU (66.7 mg, 175 μmol) was added to a mixture of intermediate E2 (70.0 mg, 117 μmol) and DIPEA (70.5 μL, 409 μmol) in DMF (1.1 mL). The reaction mixture was stirred at rt for 10 min. Methylamine (2.0 M in THF, 409 μL, 818 μmol) was added and the reaction mixture was stirred at rt for 20 h. The reaction mixture was diluted with water, brine and EtOAc. The layers were separated and the organic phase was washed with brine (3 times), dried over MgSO$_4$, filtered and concentrated under reduced pressure. The crude mixture was purified by flash chromatography (irregular SiOH, 15-40 μm, 12 g GraceResolv™, liquid injection (DCM), mobile phase gradient: heptane/EtOAc from 50:50 to 0:100). Et$_2$O was added to the residue (37 mg). The mixture was sonicated. A precipitate was formed and the suspension was concentrated to dryness. The product was dried under high vacuum at 60° C. for 16 h to give compound 47 (36 mg, 56%) as a white solid.

Compound 48

N-methyl-2-[cis-3-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclobutyl]acetamide Compound 48 was synthesized from intermediate E4 according to the procedure reported for the synthesis of compound 47. The crude mixture was purified by flash chromatography (irregular SiOH, 15-40 μm, 12 g GraceResolv™, liquid injection (DCM), mobile phase gradient: heptane/EtOAc from 50:50 to 0:100). Et$_2$O was added to the residue (80 mg) and sonicated. A precipitate was formed. The suspension was concentrated to dryness and dried under high vacuum at 60° C. for 16 h to give compound 48 (75 mg, 72%) as a white solid.

C. Compound Identification $^1$H-NMR $^1$H-NMR spectra were recorded on a Bruker Avance DRX 400 spectrometer using internal deuterium lock and equipped with reverse double-resonance ($^1$H, $^{13}$C, SEI) probe head with z gradients and operating at 400 MHz for proton and 100 MHz for carbon and a Bruker Avance 500 MHz spectrometer equipped with a Bruker 5 mm BBFO probe head with z gradients and operating at 500 MHz for proton and 125 MHz for carbon. NMR spectra were recorded at ambient temperature unless otherwise stated.

Data are reported as follow: chemical shift in parts per million (ppm) relative to TMS (δ=0 ppm) which was used as

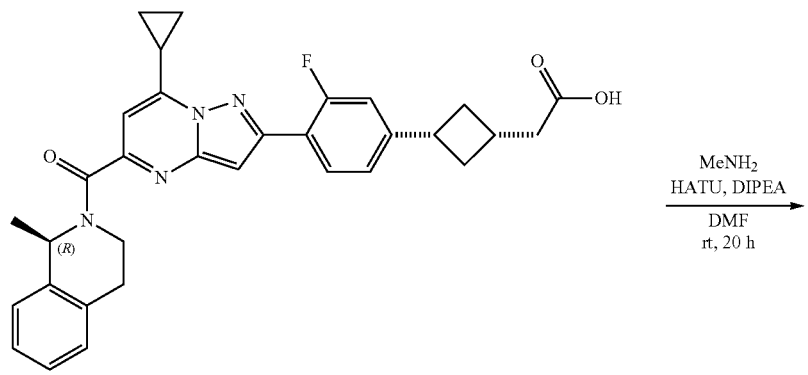

E4 (cis)

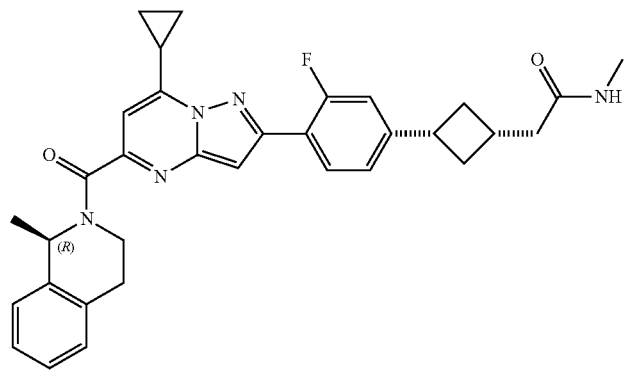

48 (cis)

internal standard, integration, multiplicity (s=singulet, d=doublet, t=triplet, q=quartet, quin=quintuplet, sex=sextuplet, m=multiplet, b=broad, or a combination of these), coupling constant(s) J in Hertz (Hz).

Compound 1

Major Rotamer (65%)
$^1$H-NMR (500 MHz, DMSO-d6) δ ppm 8.06 (t, J=8.2 Hz, 1H), 7.32 (d, J=7.3 Hz, 1H), 7.05-7.25 (m, 6H), 6.89 (s, 1H), 5.59 (q, J=6.6 Hz, 1H), 4.67 (t, J=5.7 Hz, 1H), 3.81 (br dd, J=13.4, 4.3 Hz, 1H), 3.42-3.54 (m, 2H), 3.34-3.41 (m, 1H), 2.83-3.05 (m, 2H), 2.71 (br d, J=16.4 Hz, 1H), 1.88-1.93 (m, 1H), 1.52 (d, J=6.6 Hz, 3H), 1.22-1.44 (m, 5H), 0.98 (t, J=6.9 Hz, 2H).
Minor Rotamer (35%)
$^1$H-NMR (500 MHz, DMSO-d6) δ ppm 8.06 (t, J=8.2 Hz, 1H), 7.05-7.25 (m, 7H), 6.85 (s, 1H), 4.96 (q, J=6.9 Hz, 1H), 4.67 (t, J=5.7 Hz, 1H), 4.55 (br d, J=12.0 Hz, 1H), 3.42-3.54 (m, 1H), 3.34-3.41 (m, 1H), 3.23-3.30 (m, 1H), 2.83-3.05 (m, 3H), 1.88-1.93 (m, 1H), 1.55 (d, J=6.6 Hz, 3H), 1.22-1.44 (m, 5H), 0.98 (t, J=6.9 Hz, 2H).

Compound 2

Major Rotamer (65%)
$^1$H-NMR (500 MHz, DMSO-d6) δ ppm 11.13 (br s, 1H), 8.11 (br t, J=7.4 Hz, 1H), 7.06-7.36 (m, 7H), 6.90 (s, 1H), 5.88 (s, 1H), 5.59 (q, J=6.6 Hz, 1H), 3.81 (br d, J=10.1 Hz, 1H), 3.47 (br t, J=11.8 Hz, 1H), 2.82-3.07 (m, 2H), 2.72 (br d, J=16.4 Hz, 1H), 1.63 (br t, J=6.9 Hz, 2H), 1.53 (br d, J=6.3 Hz, 3H), 1.21-1.39 (m, 4H), 1.11-1.20 (m, 2H).
Minor Rotamer (35%)
$^1$H-NMR (500 MHz, DMSO-d6) δ ppm 11.13 (br s, 1H), 8.11 (br t, J=7.4 Hz, 1H), 7.06-7.36 (m, 7H), 6.87 (s, 1H), 5.88 (s, 1H), 4.96 (q, J=6.3 Hz, 1H), 4.56 (br d, J=11.3 Hz, 1H), 3.19-3.28 (m, 1H), 2.82-3.07 (m, 3H), 1.63 (br t, J=6.9 Hz, 2H), 1.55 (br d, J=6.6 Hz, 3H), 1.21-1.39 (m, 4H), 1.11-1.20 (m, 2H).

Compound 3

Major Rotamer (65%)
$^1$H-NMR (500 MHz, DMSO-d6) δ ppm 8.12 (t, J=7.9 Hz, 1H), 7.32 (d, J=7.3 Hz, 1H), 7.10-7.29 (m, 6H), 6.91 (s, 1H), 5.59 (q, J=6.4 Hz, 1H), 3.81 (br dd, J=13.6, 3.8 Hz, 1H), 3.41-3.51 (m, 1H), 2.87-3.05 (m, 2H), 2.80-2.86 (m, 1H), 2.71 (br d, J=16.1 Hz, 1H), 2.17-2.23 (m, 1H), 1.71 (dt, J=9.3, 5.4 Hz, 1H), 1.58-1.65 (m, 1H), 1.52 (d, J=6.6 Hz, 3H), 1.32-1.38 (m, 2H), 1.24-1.31 (m, 2H).
Minor Rotamer (35%)
$^1$H-NMR (500 MHz, DMSO-d6) δ ppm 8.12 (t, J=7.9 Hz, 1H), 7.10-7.29 (m, 6H), 7.07 (d, J=7.6 Hz, 1H), 6.87 (s, 1H), 4.96 (q, J=6.8 Hz, 1H), 4.52-4.59 (m, 1H), 3.23-3.30 (m, 1H), 2.87-3.05 (m, 3H), 2.80-2.86 (m, 1H), 2.17-2.23 (m, 1H), 1.71 (dt, J=9.3, 5.4 Hz, 1H), 1.58-1.65 (m, 1H), 1.55 (d, J=6.6 Hz, 3H), 1.32-1.38 (m, 2H), 1.24-1.31 (m, 2H).

Compound 4

Major Rotamer (65%)
$^1$H-NMR (400 MHz, DMSO-d6) δ ppm 8.13 (br s, 1H), 7.05-7.38 (m, 7H), 6.90 (s, 1H), 5.59 (q, J=6.4 Hz, 1H), 3.81 (br dd, J=12.6, 3.5 Hz, 1H), 3.40-3.52 (m, 2H), 2.85-3.08 (m, 2H), 2.68-2.76 (m, 1H), 2.57-2.65 (m, 1H), 1.78 (br s, 2H), 1.52 (d, J=6.6 Hz, 3H), 1.22-1.40 (m, 4H).
Minor Rotamer (35%)
$^1$H-NMR (400 MHz, DMSO-d6) δ ppm 8.13 (br s, 1H), 7.05-7.38 (m, 7H), 6.86 (s, 1H), 4.96 (q, J=6.7 Hz, 1H), 4.56 (br d, J=13.1 Hz, 1H), 3.40-3.52 (m, 2H), 2.85-3.08 (m, 3H), 2.57-2.65 (m, 1H), 1.78 (br s, 2H), 1.55 (br d, J=6.6 Hz, 3H), 1.22-1.40 (m, 4H).

Compound 5

Major Rotamer (65%)
$^1$H-NMR (400 MHz, DMSO-d6) δ ppm 12.28 (br s, 1H), 8.12 (t, J=8.1 Hz, 1H), 7.04-7.35 (m, 7H), 6.90 (s, 1H), 5.59 (q, J=6.6 Hz, 1H), 4.34 (br t, J=5.1 Hz, 1H), 3.81 (br dd, J=13.4, 4.6 Hz, 1H), 2.82-3.08 (m, 2H), 2.71 (br d, J=16.2 Hz, 1H), 2.56-2.64 (m, 1H), 2.25-2.34 (m, 1H), 1.66 (t, J=7.3 Hz, 2H), 1.52 (d, J=6.6 Hz, 3H), 1.22-1.40 (m, 4H).
Minor Rotamer (35%)
$^1$H-NMR (400 MHz, DMSO-d6) δ ppm 12.28 (br s, 1H), 8.12 (t, J=8.1 Hz, 1H), 7.04-7.35 (m, 7H), 6.87 (s, 1H), 4.96 (q, J=6.9 Hz, 1H), 4.51-4.60 (m, 1H), 3.22-3.29 (m, 1H), 2.82-3.08 (m, 3H), 2.56-2.64 (m, 1H), 2.25-2.34 (m, 1H), 1.66 (t, J=7.3 Hz, 2H), 1.55 (br d, J=7.1 Hz, 3H), 1.22-1.40 (m, 4H).

Compound 7

Major Rotamer (65%)
$^1$H-NMR (400 MHz, DMSO-d6) δ ppm 8.09 (t, J=8.1 Hz, 1H), 7.61 (br s, 1H), 7.32 (d, J=7.6 Hz, 1H), 7.05-7.26 (m, 6H), 6.95 (br s, 1H), 6.89 (s, 1H), 5.59 (q, J=6.9 Hz, 1H), 3.81 (br dd, J=13.4, 3.8 Hz, 1H), 3.41-3.52 (m, 1H), 2.82-3.07 (m, 2H), 2.72 (br d, J=16.2 Hz, 1H), 2.29-2.35 (m, 1H), 1.90-1.98 (m, 1H), 1.52 (d, J=7.1 Hz, 3H), 1.23-1.44 (m, 6H).
Minor Rotamer (35%)
$^1$H-NMR (400 MHz, DMSO-d6) δ ppm 8.09 (t, J=8.1 Hz, 1H), 7.61 (br s, 1H), 7.05-7.26 (m, 7H), 6.95 (br s, 1H), 6.85 (s, 1H), 4.96 (q, J=6.6 Hz, 1H), 4.52-4.60 (m, 1H), 3.22-3.29 (m, 1H), 2.82-3.07 (m, 3H), 2.29-2.35 (m, 1H), 1.90-1.98 (m, 1H), 1.55 (d, J=7.1 Hz, 3H), 1.23-1.44 (m, 6H).

Compound 8

Major Rotamer (65%)
$^1$H-NMR (500 MHz, DMSO-d6) δ ppm 8.19 (br t, J=7.9 Hz, 1H), 7.74 (br s, 1H), 7.45 (br d, J=8.2 Hz, 1H), 7.41 (br d, J=12.0 Hz, 1H), 7.32 (br d, J=7.3 Hz, 1H), 7.06-7.27 (m, 4H), 6.98 (br s, 1H), 6.93 (s, 1H), 5.59 (q, J=6.6 Hz, 1H), 3.82 (dd, J=13.4, 3.9 Hz, 1H), 3.42-3.54 (m, 1H), 2.83-3.07 (m, 2H), 2.72 (br d, J=16.1 Hz, 1H), 2.56-2.66 (m, 1H), 1.90-1.97 (m, 1H), 1.73-1.85 (m, 1H), 1.53 (br d, J=6.9 Hz, 3H), 1.26-1.40 (m, 4H).
Minor Rotamer (35%)
$^1$H-NMR (500 MHz, DMSO-d6) δ ppm 8.19 (br t, J=7.9 Hz, 1H), 7.74 (br s, 1H), 7.45 (br d, J=8.2 Hz, 1H), 7.41 (br d, J=12.0 Hz, 1H), 7.06-7.27 (m, 5H), 6.98 (br s, 1H), 6.89 (s, 1H), 4.98 (q, J=6.6 Hz, 1H), 4.56 (br dd, J=12.3, 3.8 Hz, 1H), 3.23-3.31 (m, 1H), 2.83-3.07 (m, 2H), 2.56-2.66 (m, 2H), 1.90-1.97 (m, 1H), 1.73-1.85 (m, 1H), 1.56 (br d, J=6.6 Hz, 3H), 1.26-1.40 (m, 4H).

Compound 9

Major Rotamer (65%)
$^1$H-NMR (500 MHz, DMSO-d6) δ ppm 8.17 (br t, J=7.6 Hz, 1H), 7.60 (br s, 1H), 7.22-7.33 (m, 3H), 6.98-7.20 (m, 5H), 6.85 (s, 1H), 5.53 (q, J=6.6 Hz, 1H), 3.75 (br d, J=9.8

Hz, 1H), 3.40 (br t, J=11.2 Hz, 1H), 2.76-3.01 (m, 2H), 2.65 (br d, J=16.1 Hz, 1H), 2.23-2.29 (m, 1H), 2.06 (dt, J=20.8, 7.3 Hz, 1H), 1.61-1.72 (m, 1H), 1.46 (br d, J=6.6 Hz, 3H), 1.26-1.34 (m, 2H), 1.14-1.25 (m, 2H).
Minor Rotamer (35%)
$^1$H-NMR (500 MHz, DMSO-d6) δ ppm 8.17 (br t, J=7.6 Hz, 1H), 7.60 (br s, 1H), 7.22-7.33 (m, 2H), 6.98-7.20 (m, 6H), 6.81 (s, 1H), 4.91 (q, J=6.3 Hz, 1H), 4.49 (br d, J=10.4 Hz, 1H), 3.15-3.22 (m, 1H), 2.76-3.01 (m, 3H), 2.23-2.29 (m, 1H), 2.06 (dt, J=20.8, 7.3 Hz, 1H), 1.61-1.72 (m, 1H), 1.49 (br d, J=6.9 Hz, 3H), 1.26-1.34 (m, 2H), 1.14-1.25 (m, 2H).

Compound 10

Major Rotamer (65%)
$^1$H-NMR (500 MHz, DMSO-d6) δ ppm 8.09 (br t, J=8.0 Hz, 1H), 7.63 (br s, 1H), 7.38 (d, J=5.4 Hz, 1H), 7.15-7.21 (m, 2H), 7.08-7.12 (m, 1H), 7.02 (d, J=5.0 Hz, 1H), 6.97 (br s, 1H), 6.89 (s, 1H), 5.54 (q, J=6.8 Hz, 1H), 3.92 (br dd, J=13.7, 5.2 Hz, 1H), 3.37-3.46 (m, 1H), 2.91-3.00 (m, 2H), 2.72-2.77 (m, 1H), 2.29-2.35 (m, 1H), 1.91-1.97 (m, 1H), 1.46 (d, J=6.9 Hz, 3H), 1.40 (br dt, J=9.4, 4.6 Hz, 1H), 1.25-1.38 (m, 5H).
Minor Rotamer (35%)
$^1$H-NMR (500 MHz, DMSO-d6) δ ppm 8.08 (br t, J=8.0 Hz, 1H), 7.63 (br s, 1H), 7.29 (d, J=5.0 Hz, 1H), 7.15-7.21 (m, 2H), 7.08-7.12 (m, 1H), 6.97 (br s, 1H), 6.87 (s, 1H), 6.79 (d, J=5.4 Hz, 1H), 4.90 (q, J=6.2 Hz, 1H), 4.71 (br dd, J=13.2, 5.0 Hz, 1H), 3.18-3.25 (m, 1H), 2.91-3.00 (m, 3H), 2.29-2.35 (m, 1H), 1.91-1.97 (m, 1H), 1.50 (d, J=6.6 Hz, 3H), 1.40 (br dt, J=9.4, 4.6 Hz, 1H), 1.25-1.38 (m, 5H).

Compound 11

Major Rotamer (65%)
$^1$H-NMR (500 MHz, DMSO-d6) δ ppm 8.09 (br t, J=8.0 Hz, 1H), 7.63 (br s, 1H), 7.14-7.22 (m, 2H), 7.10 (d, J=3.5 Hz, 1H), 6.97 (br s, 1H), 6.89 (s, 1H), 6.68 (d, J=1.6 Hz, 1H), 5.38 (q, J=6.4 Hz, 1H), 3.91 (br dd, J=13.7, 4.9 Hz, 1H), 3.39-3.49 (m, 1H), 2.92-3.00 (m, 1H), 2.72-2.92 (m, 1H), 2.59 (br dd, J=15.9, 1.7 Hz, 1H), 2.30-2.35 (m, 1H), 1.91-1.97 (m, 1H), 1.43 (d, J=6.9 Hz, 3H), 1.23-1.41 (m, 6H).
Minor Rotamer (35%)
$^1$H-NMR (500 MHz, DMSO-d6) δ ppm 8.08 (br t, J=7.9 Hz, 1H), 7.63 (br s, 1H), 7.14-7.22 (m, 2H), 7.10 (d, J=3.5 Hz, 1H), 6.97 (br s, 1H), 6.88 (s, 1H), 6.43 (d, J=1.6 Hz, 1H), 4.76 (q, J=4.8 Hz, 1H), 4.65-4.71 (m, 1H), 3.20-3.28 (m, 1H), 2.92-3.00 (m, 1H), 2.72-2.92 (m, 2H), 2.30-2.35 (m, 1H), 1.91-1.97 (m, 1H), 1.47 (d, J=6.6 Hz, 3H), 1.23-1.41 (m, 6H).

Compound 12

Major Rotamer (65%)
$^1$H-NMR (400 MHz, DMSO-d6) δ ppm 8.04-8.13 (m, 2H), 7.32 (d, J=7.6 Hz, 1H), 7.05-7.26 (m, 6H), 6.89 (s, 1H), 5.59 (q, J=6.6 Hz, 1H), 3.81 (ddd, J=13.6, 5.1, 1.3 Hz, 1H), 3.41-3.52 (m, 1H), 2.85-3.06 (m, 2H), 2.65-2.76 (m, 1H), 2.63 (d, J=4.6 Hz, 3H), 2.30-2.38 (m, 1H), 1.88-1.96 (m, 1H), 1.52 (d, J=7.1 Hz, 3H), 1.42 (dt, J=9.1, 4.6 Hz, 1H), 1.19-1.39 (m, 5H).
Minor Rotamer (35%)
$^1$H-NMR (400 MHz, DMSO-d6) δ ppm 8.04-8.13 (m, 2H), 7.05-7.26 (m, 7H), 6.86 (s, 1H), 4.96 (q, J=6.6 Hz, 1H), 4.51-4.59 (m, 1H), 3.22-3.29 (m, 1H), 2.85-3.06 (m, 3H), 2.63 (d, J=4.6 Hz, 3H), 2.30-2.38 (m, 1H), 1.88-1.96 (m, 1H), 1.54 (d, J=7.1 Hz, 3H), 1.42 (dt, J=9.1, 4.6 Hz, 1H), 1.19-1.39 (m, 5H).

Compound 13

Major Rotamer (65%)
$^1$H-NMR (500 MHz, DMSO-d6) δ ppm 8.08 (t, J=8.0 Hz, 1H), 7.32 (d, J=7.6 Hz, 1H), 7.05-7.26 (m, 6H), 6.97 (br s, 1H), 6.89 (s, 1H), 5.59 (q, J=6.5 Hz, 1H), 3.82 (br dd, J=13.6, 3.8 Hz, 1H), 3.42-3.51 (m, 1H), 2.83-3.06 (m, 2H), 2.72 (br d, J=16.1 Hz, 1H), 2.42 (br s, 1H), 1.88 (br s, 1H), 1.52 (d, J=6.9 Hz, 3H), 1.47 (dt, J=9.2, 4.7 Hz, 1H), 1.32-1.42 (m, 3H), 1.23-1.31 (m, 2H).
Minor Rotamer (35%)
$^1$H-NMR (500 MHz, DMSO-d6) δ ppm 8.08 (t, J=8.0 Hz, 1H), 7.05-7.26 (m, 7H), 6.97 (br s, 1H), 6.85 (s, 1H), 4.96 (q, J=6.6 Hz, 1H), 4.52-4.59 (m, 1H), 3.42-3.51 (m, 1H), 2.83-3.06 (m, 3H), 2.42 (br s, 1H), 1.88 (br s, 1H), 1.55 (d, J=6.9 Hz, 3H), 1.47 (dt, J=9.2, 4.7 Hz, 1H), 1.32-1.42 (m, 3H), 1.23-1.31 (m, 2H).

Compound 14

Major Rotamer (65%)
$^1$H-NMR (400 MHz, DMSO-d6) δ ppm 8.14 (br t, J=5.1 Hz, 1H), 8.09 (br t, J=8.1 Hz, 1H), 7.32 (br d, J=7.1 Hz, 1H), 7.05-7.26 (m, 6H), 6.89 (s, 1H), 5.59 (q, J=6.2 Hz, 1H), 3.81 (br dd, J=13.9, 4.3 Hz, 1H), 3.41-3.52 (m, 1H), 3.07-3.16 (m, 2H), 2.82-3.07 (m, 2H), 2.71 (br d, J=15.7 Hz, 1H), 2.29-2.37 (m, 1H), 1.88-1.97 (m, 1H), 1.52 (d, J=7.1 Hz, 3H), 1.41 (dt, J=8.8, 4.7 Hz, 1H), 1.22-1.38 (m, 5H), 1.03 (t, J=7.3 Hz, 3H).
Minor Rotamer (35%)
$^1$H-NMR (400 MHz, DMSO-d6) δ ppm 8.14 (br t, J=5.1 Hz, 1H), 8.09 (br t, J=8.1 Hz, 1H), 7.05-7.26 (m, 7H), 6.86 (s, 1H), 4.96 (q, J=7.1 Hz, 1H), 4.55 (d, J=12.1 Hz, 1H), 3.21-3.30 (m, 1H), 3.07-3.16 (m, 2H), 2.82-3.07 (m, 3H), 2.29-2.37 (m, 1H), 1.88-1.97 (m, 1H), 1.55 (d, J=7.1 Hz, 3H), 1.41 (dt, J=8.8, 4.7 Hz, 1H), 1.22-1.38 (m, 5H), 1.03 (t, J=7.3 Hz, 3H).

Compound 15

Major Rotamer (65%)
$^1$H-NMR (400 MHz, DMSO-d6) δ ppm 8.14 (br t, J=5.1 Hz, 1H), 8.09 (br t, J=7.8 Hz, 1H), 7.32 (br d, J=7.1 Hz, 1H), 7.04-7.26 (m, 6H), 6.89 (s, 1H), 5.59 (q, J=7.1 Hz, 1H), 3.81 (br dd, J=13.1, 3.0 Hz, 1H), 3.42-3.52 (m, 1H), 2.82-3.14 (m, 4H), 2.71 (br d, J=16.7 Hz, 1H), 2.29-2.38 (m, 1H), 1.92-2.01 (m, 1H), 1.48-1.58 (m, 3H), 1.38-1.47 (m, 3H), 1.23-1.38 (m, 5H), 0.86 (t, J=7.3 Hz, 3H).
Minor Rotamer (35%)
$^1$H-NMR (400 MHz, DMSO-d6) δ ppm 8.14 (br t, J=5.1 Hz, 1H), 8.09 (br t, J=7.8 Hz, 1H), 7.04-7.26 (m, 7H), 6.86 (s, 1H), 4.96 (q, J=6.1 Hz, 1H), 4.55 (br d, J=11.6 Hz, 1H), 3.22-3.30 (m, 1H), 2.82-3.14 (m, 5H), 2.29-2.38 (m, 1H), 1.92-2.01 (m, 1H), 1.48-1.58 (m, 3H), 1.38-1.47 (m, 3H), 1.23-1.38 (m, 5H), 0.86 (t, J=7.3 Hz, 3H).

Compound 16

Major Rotamer (70%)
$^1$H-NMR (500 MHz, DMSO-d6) δ ppm 8.31 (br s, 1H), 8.09 (br t, J=7.7 Hz, 1H), 7.32 (br d, J=7.3 Hz, 1H), 7.13-7.26 (m, 5H), 7.05-7.13 (m, 1H), 6.89 (s, 1H), 5.75-5.89 (m, 1H), 5.54-5.65 (m, 1H), 5.16 (br d, J=17.0 Hz, 1H), 5.07 (br d, J=10.4 Hz, 1H), 3.70-3.85 (m, 3H), 3.43-3.52 (m, 1H), 2.83-3.06 (m, 2H), 2.72 (br d, J=16.7 Hz, 1H), 2.36 (s, 1H), 2.00-2.05 (m, 1H), 1.53 (d, J=6.6 Hz, 3H), 1.41-1.47 (m, 1H), 1.23-1.39 (m, 5H).

Minor Rotamer (30%)

$^1$H-NMR (500 MHz, DMSO-d6) δ ppm 8.31 (br s, 1H), 8.09 (br t, J=7.7 Hz, 1H), 7.13-7.26 (m, 5H), 7.05-7.13 (m, 2H), 6.85 (s, 1H), 5.75-5.89 (m, 1H), 5.16 (br d, J=17.0 Hz, 1H), 5.07 (br d, J=10.4 Hz, 1H), 4.94-5.00 (m, 1H), 4.55 (br d, J=10.7 Hz, 1H), 3.70-3.85 (m, 2H), 3.43-3.52 (m, 1H), 2.83-3.06 (m, 3H), 2.36 (s, 1H), 2.00-2.05 (m, 1H), 1.55 (d, J=6.9 Hz, 3H), 1.41-1.47 (m, 1H), 1.23-1.39 (m, 5H).

Compound 17

Major Rotamer (65%)

$^1$H-NMR (400 MHz, DMSO-d6) δ ppm 8.64 (br t, J=5.1 Hz, 1H), 8.09 (br t, J=8.1 Hz, 1H), 7.32 (br d, J=7.6 Hz, 1H), 7.04-7.26 (m, 6H), 6.89 (s, 1H), 5.59 (q, J=6.6 Hz, 1H), 3.88-3.96 (m, 2H), 3.81 (br dd, J=13.6, 3.5 Hz, 1H), 3.42-3.51 (m, 1H), 3.13 (t, J=2.3 Hz, 1H), 2.82-3.06 (m, 2H), 2.71 (br d, J=16.2 Hz, 1H), 2.34-2.41 (m, 1H), 1.96-2.03 (m, 1H), 1.52 (d, J=7.1 Hz, 3H), 1.44 (dt, J=9.1, 4.6 Hz, 1H), 1.31-1.41 (m, 3H), 1.22-1.31 (m, 2H).

Minor Rotamer (35%)

$^1$H-NMR (400 MHz, DMSO-d6) δ ppm 8.64 (br t, J=5.1 Hz, 1H), 8.09 (br t, J=8.1 Hz, 1H), 7.04-7.26 (m, 7H), 6.86 (s, 1H), 4.96 (q, J=6.4 Hz, 1H), 4.55 (br d, J=12.1 Hz, 1H), 3.88-3.96 (m, 2H), 3.21-3.30 (m, 1H), 3.13 (t, J=2.3 Hz, 1H), 2.82-3.06 (m, 3H), 2.34-2.41 (m, 1H), 1.96-2.03 (m, 1H), 1.52 (d, J=7.1 Hz, 3H), 1.44 (dt, J=9.1, 4.6 Hz, 1H), 1.31-1.41 (m, 3H), 1.22-1.31 (m, 2H).

Compound 18

Major Rotamer (65%)

$^1$H-NMR (400 MHz, DMSO-d6) δ ppm 8.56 (br t, J=5.3 Hz, 1H), 8.10 (br t, J=7.8 Hz, 1H), 7.32 (br d, J=7.6 Hz, 1H), 7.04-7.26 (m, 6H), 6.89 (s, 1H), 5.59 (q, J=6.6 Hz, 1H), 3.81 (br dd, J=14.1, 4.0 Hz, 1H), 3.42-3.52 (m, 1H), 3.28-3.41 (m, 2H partially obscured by H$_2$O peak), 2.82-3.07 (m, 2H), 2.68-2.76 (m, 1H), 2.67 (br t, J=6.6 Hz, 2H), 2.34-2.41 (m, 1H), 1.96-2.04 (m, 1H), 1.49-1.58 (m, 3H), 1.45 (dt, J=9.1, 4.6 Hz, 1H), 1.31-1.41 (m, 3H), 1.23-1.31 (m, 2H).

Minor Rotamer (35%)

$^1$H-NMR (400 MHz, DMSO-d6) δ ppm 8.56 (br t, J=5.3 Hz, 1H), 8.10 (br t, J=7.8 Hz, 1H), 7.04-7.26 (m, 7H), 6.86 (s, 1H), 4.96 (q, J=6.6 Hz, 1H), 4.55 (br d, J=11.6 Hz, 1H), 3.28-3.41 (m, 2H partially obscured by H$_2$O peak), 3.21-3.30 (m, 1H), 2.82-3.07 (m, 3H), 2.67 (br t, J=6.6 Hz, 2H), 2.34-2.41 (m, 1H), 1.96-2.04 (m, 1H), 1.49-1.58 (m, 3H), 1.45 (dt, J=9.1, 4.6 Hz, 1H), 1.31-1.41 (m, 3H), 1.23-1.31 (m, 2H).

Compound 19

Major Rotamer (65%)

$^1$H-NMR (500 MHz, DMSO-d6) δ ppm 8.94 (br d, J=6.9 Hz, 1H), 8.10 (br t, J=8.0 Hz, 1H), 7.32 (d, J=7.6 Hz, 1H), 7.05-7.26 (m, 6H), 6.90 (s, 1H), 5.60 (q, J=6.6 Hz, 1H), 4.85 (sxt, J=6.9 Hz, 1H), 4.68-4.77 (m, 2H), 4.43 (t, J=6.1 Hz, 2H), 3.82 (br dd, J=13.9, 4.1 Hz, 1H), 3.43-3.52 (m, 1H), 2.83-3.06 (m, 2H), 2.72 (br d, J=15.8 Hz, 1H), 2.33-2.39 (m, 1H), 1.93-2.01 (m, 1H), 1.53 (d, J=6.6 Hz, 3H), 1.44 (dt, J=9.0, 4.7 Hz, 1H), 1.32-1.41 (m, 3H), 1.24-1.31 (m, 2H).

Minor Rotamer (35%)

$^1$H-NMR (500 MHz, DMSO-d6) δ ppm 8.94 (br d, J=6.9 Hz, 1H), 8.10 (br t, J=8.0 Hz, 1H), 7.05-7.26 (m, 7H), 6.86 (s, 1H), 4.97 (q, J=6.5 Hz, 1H), 4.85 (sxt, J=6.9 Hz, 1H), 4.68-4.77 (m, 2H), 4.56 (br d, J=12.6 Hz, 1H), 4.43 (t, J=6.1 Hz, 2H), 3.23-3.31 (m, 1H), 2.83-3.06 (m, 3H), 2.33-2.39 (m, 1H), 1.93-2.01 (m, 1H), 1.55 (br d, J=6.6 Hz, 3H), 1.44 (dt, J=9.0, 4.7 Hz, 1H), 1.32-1.41 (m, 3H), 1.24-1.31 (m, 2H).

Compound 20

Major Rotamer (65%)

$^1$H-NMR (500 MHz, DMSO-d6, 77° C.) δ ppm 8.01-8.17 (m, 2H), 7.00-7.33 (m, 7H), 6.76-6.87 (m, 1H), 5.60 (br d, J=2.8 Hz, 1H), 3.85 (br dd, J=8.8, 2.2 Hz, 1H), 3.44-3.55 (m, 1H), 2.87-2.97 (m, 2H), 2.70-2.79 (m, 1H), 2.33 (br d, J=3.5 Hz, 1H), 1.89 (br s, 1H), 1.53 (br d, J=5.0 Hz, 3H), 1.17-1.45 (m, 9H), 0.65 (br s, 2H), 0.51 (br s, 2H).

Minor Rotamer (35%)

$^1$H-NMR (500 MHz, DMSO-d6, 77° C.) δ ppm 8.01-8.17 (m, 2H), 7.00-7.33 (m, 7H), 6.76-6.87 (m, 1H), 4.98-5.10 (m, 1H), 4.48-4.61 (m, 1H), 3.24-3.36 (m, 1H), 2.87-2.97 (m, 3H), 2.33 (br d, J=3.5 Hz, 1H), 1.89 (br s, 1H), 1.53 (br d, J=5.0 Hz, 3H), 1.17-1.45 (m, 9H), 0.65 (br s, 2H), 0.51 (br s, 2H).

Compound 21

Major Rotamer (65%)

$^1$H-NMR (500 MHz, DMSO-d6) δ ppm 8.17 (br t, J=4.9 Hz, 1H), 8.09 (br t, J=7.7 Hz, 1H), 7.32 (br d, J=7.3 Hz, 1H), 7.05-7.26 (m, 6H), 6.89 (s, 1H), 5.59 (q, J=6.6 Hz, 1H), 4.68 (br t, J=5.0 Hz, 1H), 3.82 (br dd, J=12.9, 3.8 Hz, 1H), 3.45-3.51 (m, 1H), 3.42 (q, J=5.4 Hz, 2H), 3.17 (q, J=5.5 Hz, 2H), 2.90-3.06 (m, 2H), 2.72 (br d, J=16.4 Hz, 1H), 2.32-2.38 (m, 1H), 2.00-2.06 (m, 1H), 1.53 (br d, J=6.6 Hz, 3H), 1.42 (dt, J=8.7, 4.5 Hz, 1H), 1.24-1.39 (m, 5H).

Minor Rotamer (35%)

$^1$H-NMR (500 MHz, DMSO-d6) δ ppm 8.17 (br t, J=4.9 Hz, 1H), 8.09 (br t, J=7.7 Hz, 1H), 7.05-7.26 (m, 7H), 6.85 (s, 1H), 4.97 (q, J=6.6 Hz, 1H), 4.68 (br t, J=5.0 Hz, 1H), 4.55 (br d, J=14.8 Hz, 1H), 3.42 (q, J=5.4 Hz, 2H), 3.24-3.29 (m, 1H), 3.17 (q, J=5.5 Hz, 2H), 2.90-3.06 (m, 2H), 2.83-2.90 (m, 1H), 2.32-2.38 (m, 1H), 2.00-2.06 (m, 1H), 1.55 (br d, J=6.9 Hz, 3H), 1.42 (dt, J=8.7, 4.5 Hz, 1H), 1.24-1.39 (m, 5H).

Compound 22

Major Rotamer (65%)

$^1$H-NMR (400 MHz, DMSO-d6) δ ppm 8.07 (br t, J=7.8 Hz, 1H), 7.32 (br d, J=7.1 Hz, 1H), 7.06-7.28 (m, 6H), 6.90 (s, 1H), 5.59 (q, J=7.1 Hz, 1H), 3.77-3.86 (m, 1H), 3.42-3.53 (m, 1H), 3.12 (s, 3H), 2.90-3.06 (m, 2H), 2.87 (s, 3H), 2.71 (br d, J=16.7 Hz, 1H), 2.39 (t, J=6.6 Hz, 2H), 1.52 (br d, J=7.1 Hz, 3H), 1.41-1.49 (m, 1H), 1.20-1.39 (m, 5H).

Minor Rotamer (35%)

$^1$H-NMR (400 MHz, DMSO-d6) δ ppm 8.07 (br t, J=7.8 Hz, 1H), 7.06-7.28 (m, 7H), 6.86 (s, 1H), 4.96 (q, J=6.6 Hz, 1H), 4.51-4.60 (m, 1H), 3.20-3.30 (m, 1H), 3.12 (s, 3H), 2.90-3.06 (m, 2H), 2.83-2.90 (m, 1H), 2.87 (s, 3H), 2.39 (t, J=6.6 Hz, 2H), 1.55 (br d, J=7.1 Hz, 3H), 1.41-1.49 (m, 1H), 1.20-1.39 (m, 5H).

Compound 23

Major Rotamer (65%)
¹H-NMR (400 MHz, DMSO-d6) δ ppm 8.07 (t, J=8.3 Hz, 1H), 7.32 (d, J=7.1 Hz, 1H), 7.05-7.27 (m, 6H), 6.90 (s, 1H), 5.59 (q, J=6.6 Hz, 1H), 3.81 (br dd, J=13.6, 4.0 Hz, 1H), 3.59-3.68 (m, 1H), 3.42-3.55 (m, 2H), 3.28-3.34 (m, 2H partially obscured by H₂O peak), 2.86-3.06 (m, 2H), 2.71 (br d, J=16.7 Hz, 1H), 2.36-2.43 (m, 1H), 2.21 (dt, J=8.5, 4.6 Hz, 1H), 1.84-1.93 (m, 2H), 1.74-1.83 (m, 2H), 1.52 (d, J=6.6 Hz, 3H), 1.43-1.49 (m, 1H), 1.21-1.39 (m, 5H).
Minor Rotamer (35%)
¹H-NMR (400 MHz, DMSO-d6) δ ppm 8.07 (t, J=8.3 Hz, 1H), 7.05-7.27 (m, 7H), 6.86 (s, 1H), 4.96 (q, J=6.4 Hz, 1H), 4.55 (br d, J=12.1 Hz, 1H), 3.59-3.68 (m, 1H), 3.42-3.55 (m, 1H), 3.28-3.34 (m, 2H partially obscured by H₂O peak), 3.22-3.29 (m, 1H), 2.86-3.06 (m, 3H), 2.36-2.43 (m, 1H), 2.21 (dt, J=8.5, 4.6 Hz, 1H), 1.84-1.93 (m, 2H), 1.74-1.83 (m, 2H), 1.55 (br d, J=6.6 Hz, 3H), 1.43-1.49 (m, 1H), 1.21-1.39 (m, 5H).

Compound 24

Major Rotamer (35%)
¹H-NMR (500 MHz, DMSO-d6) δ ppm 12.06 (s, 1H), 8.12 (t, J=8.0 Hz, 1H), 7.32 (d, J=7.3 Hz, 1H), 7.10-7.29 (m, 6H), 6.91 (s, 1H), 5.59 (q, J=6.6 Hz, 1H), 3.81 (br dd, J=13.9, 4.4 Hz, 1H), 3.43-3.51 (m, 1H), 3.29 (s, 3H), 2.83-3.06 (m, 2H), 2.72 (br d, J=16.1 Hz, 1H), 2.53-2.59 (m, 1H), 2.11-2.18 (m, 1H), 1.56-1.62 (m, 2H), 1.52 (d, J=6.9 Hz, 3H), 1.32-1.38 (m, 2H), 1.22-1.31 (m, 2H).
Minor Rotamer (65%)
¹H-NMR (500 MHz, DMSO-d6) δ ppm 12.06 (s, 1H), 8.12 (t, J=8.0 Hz, 1H), 7.10-7.29 (m, 6H), 7.07 (br d, J=7.1 Hz, 1H), 6.87 (s, 1H), 4.96 (q, J=6.6 Hz, 1H), 4.55 (br dd, J=12.3, 3.8 Hz, 1H), 3.29 (s, 3H), 3.24-3.28 (m, 1H), 2.83-3.06 (m, 3H), 2.53-2.59 (m, 1H), 2.11-2.18 (m, 1H), 1.56-1.62 (m, 2H), 1.55 (d, J=6.6 Hz, 3H), 1.32-1.38 (m, 2H), 1.22-1.31 (m, 2H).

Compound 25

Major Rotamer (65%)
¹H-NMR (400 MHz, DMSO-d6) δ ppm 11.96 (s, 1H), 8.12 (t, J=7.8 Hz, 1H), 7.32 (d, J=7.6 Hz, 1H), 7.05-7.29 (m, 6H), 6.90 (s, 1H), 5.59 (q, J=6.6 Hz, 1H), 3.81 (br dd, J=12.6, 4.0 Hz, 1H), 3.43-3.51 (m, 1H), 3.40 (q, J=7.1 Hz, 2H), 2.82-3.06 (m, 2H), 2.71 (br d, J=16.2 Hz, 1H), 2.53-2.58 (m, 1H partially obscured by DMSO peak), 2.12-2.19 (m, 1H), 1.50-1.63 (m, 2H), 1.52 (d, J=7.1 Hz, 3H), 1.25-1.39 (m, 4H), 1.23 (t, J=7.3 Hz, 3H).
Minor Rotamer (35%)
¹H-NMR (400 MHz, DMSO-d6) δ ppm 11.96 (s, 1H), 8.12 (t, J=7.8 Hz, 1H), 7.05-7.29 (m, 7H), 6.87 (s, 1H), 4.96 (q, J=7.1 Hz, 1H), 4.51-4.59 (m, 1H), 3.40 (q, J=7.1 Hz, 2H), 3.22-3.30 (m, 1H), 2.82-3.06 (m, 3H), 2.53-2.58 (m, 1H partially obscured by DMSO peak), 2.12-2.19 (m, 1H), 1.50-1.63 (m, 2H), 1.55 (br d, J=7.1 Hz, 3H), 1.25-1.39 (m, 4H), 1.23 (t, J=7.3 Hz, 3H).

Compound 26

Major Rotamer (65%)
¹H-NMR (400 MHz, DMSO-d6) δ ppm 12.01 (s, 1H), 8.11 (t, J=8.1 Hz, 1H), 7.32 (d, J=7.6 Hz, 1H), 7.05-7.28 (m, 6H), 6.90 (s, 1H), 5.59 (q, J=6.7 Hz, 1H), 3.81 (br dd, J=13.9, 3.8 Hz, 1H), 3.42-3.51 (m, 1H), 3.33 (s, 1H), 2.83-3.06 (m, 2H), 2.71 (br d, J=16.7 Hz, 1H), 2.53-2.57 (m, 1H partially obscured by DMSO peak), 2.06-2.18 (m, 2H), 1.50-1.63 (m, 2H), 1.52 (d, J=6.6 Hz, 3H), 1.21-1.39 (m, 5H), 1.03 (d, J=6.6 Hz, 6H).
Minor Rotamer (35%)
¹H-NMR (400 MHz, DMSO-d6) δ ppm 12.01 (s, 1H), 8.11 (t, J=8.1 Hz, 1H), 7.05-7.28 (m, 7H), 6.87 (s, 1H), 4.96 (q, J=6.2 Hz, 1H), 4.52-4.59 (m, 1H), 3.33 (s, 1H), 3.22-3.30 (m, 1H), 2.83-3.06 (m, 3H), 2.53-2.57 (m, 1H partially obscured by DMSO peak), 2.06-2.18 (m, 2H), 1.50-1.63 (m, 2H), 1.55 (d, J=6.6 Hz, 3H), 1.21-1.39 (m, 5H), 1.03 (d, J=6.6 Hz, 6H).

Compound 27

Major Rotamer (65%)
¹H-NMR (400 MHz, DMSO-d6) δ ppm 12.02 (s, 1H), 8.12 (br t, J=8.1 Hz, 1H), 7.04-7.34 (m, 7H), 6.90 (s, 1H), 5.59 (q, J=6.2 Hz, 1H), 3.77-3.84 (m, 1H), 3.41-3.51 (m, 1H), 2.85-3.06 (m, 3H), 2.68-2.76 (m, 1H), 2.11-2.18 (m, 1H), 1.49-1.62 (m, 2H), 1.52 (d, J=7.1 Hz, 3H), 1.21-1.39 (m, 5H), 1.05-1.13 (m, 4H).
Minor Rotamer (35%)
¹H-NMR (400 MHz, DMSO-d6) δ ppm 12.02 (s, 1H), 8.12 (br t, J=8.1 Hz, 1H), 7.04-7.34 (m, 7H), 6.87 (s, 1H), 4.96 (q, J=6.7 Hz, 1H), 4.51-4.59 (m, 1H), 3.22-3.31 (m, 1H), 2.85-3.06 (m, 4H), 2.11-2.18 (m, 1H), 1.49-1.62 (m, 2H), 1.55 (d, J=6.6 Hz, 3H), 1.21-1.39 (m, 5H), 1.05-1.13 (m, 4H).

Compound 28

Major Rotamer (65%)
¹H-NMR (400 MHz, DMSO-d6) δ ppm 12.07 (s, 1H), 8.12 (t, J=8.1 Hz, 1H), 7.38 (d, J=5.6 Hz, 1H), 7.26 (br d, J=12.6 Hz, 1H), 7.20 (d, J=9.1 Hz, 1H), 7.09-7.13 (m, 1H), 7.02 (d, J=5.6 Hz, 1H), 6.90 (s, 1H), 5.53 (q, J=6.6 Hz, 1H), 3.92 (br dd, J=13.9, 4.8 Hz, 1H), 3.36-3.46 (m, 1H), 3.28 (s, 3H), 2.82-3.01 (m, 2H), 2.74 (br dd, J=15.9, 2.8 Hz, 1H), 2.53-2.59 (m, 1H partially obscured by DMSO peak), 2.10-2.18 (m, 1H), 1.53-1.62 (m, 2H), 1.46 (d, J=6.6 Hz, 3H), 1.32-1.39 (m, 2H), 1.21-1.31 (m, 2H).
Minor Rotamer (35%)
¹H-NMR (400 MHz, DMSO-d6) δ ppm 12.07 (s, 1H), 8.11 (t, J=8.1 Hz, 1H), 7.29 (d, J=5.6 Hz, 1H), 7.26 (br d, J=12.6 Hz, 1H), 7.20 (d, J=9.1 Hz, 1H), 7.09-7.13 (m, 1H), 6.88 (s, 1H), 6.79 (d, J=5.1 Hz, 1H), 4.89 (q, J=6.1 Hz, 1H), 4.71 (br dd, J=12.6, 4.5 Hz, 1H), 3.28 (s, 3H), 3.15-3.26 (m, 1H), 2.82-3.01 (m, 3H), 2.53-2.59 (m, 1H partially obscured by DMSO peak), 2.10-2.18 (m, 1H), 1.53-1.62 (m, 2H), 1.50 (d, J=6.6 Hz, 3H), 1.32-1.39 (m, 2H), 1.21-1.31 (m, 2H).

Compound 29

Major Rotamer (65%)
¹H-NMR (400 MHz, DMSO-d6) δ ppm 8.07 (t, J=8.1 Hz, 1H), 7.32 (d, J=7.1 Hz, 1H), 7.05-7.25 (m, 6H), 6.94 (s, 1H), 6.88 (s, 1H), 5.59 (q, J=7.1 Hz, 1H), 3.82 (br dd, J=13.1, 4.5 Hz, 1H), 3.41-3.48 (m, 1H partially obscured by H₂O peak), 2.85-3.06 (m, 2H), 2.71 (br d, J=17.7 Hz, 1H), 2.26-2.32 (m, 1H), 1.85-1.92 (m, 1H), 1.52 (d, J=7.1 Hz, 3H), 1.31-1.42 (m, 3H), 1.19-1.30 (m, 3H).
Minor Rotamer (35%)
¹H-NMR (400 MHz, DMSO-d6) δ ppm 8.07 (t, J=8.1 Hz, 1H), 7.05-7.25 (m, 7H), 6.94 (s, 1H), 6.84 (s, 1H), 4.96 (q, J=6.6 Hz, 1H), 4.52-4.59 (m, 1H), 3.22-3.32 (m, 1H), 2.85-3.06 (m, 3H), 2.26-2.32 (m, 1H), 1.85-1.92 (m, 1H), 1.54 (br d, J=6.6 Hz, 3H), 1.31-1.42 (m, 3H), 1.19-1.30 (m, 3H).

Compound 30

Major Rotamer (65%)
¹H-NMR (400 MHz, DMSO-d6) δ ppm 8.07 (t, J=8.1 Hz, 1H), 7.32 (d, J=7.1 Hz, 1H), 7.06-7.25 (m, 6H), 6.89 (s, 1H), 6.33 (d, J=3.0 Hz, 1H), 6.14 (d, J=2.0 Hz, 1H), 5.59 (q, J=6.6 Hz, 1H), 3.81 (br dd, J=12.6, 5.1 Hz, 1H), 3.41-3.51 (m, 1H), 2.85-3.06 (m, 2H), 2.71-2.79 (m, 1H), 2.67-2.71 (m, 1H), 2.37-2.44 (m, 1H), 1.94-2.02 (m, 1H), 1.52 (d, J=6.6 Hz, 3H), 1.18-1.40 (m, 6H), 0.53-0.59 (m, 2H), 0.31-0.36 (m, 2H).
Minor Rotamer (35%)
¹H-NMR (400 MHz, DMSO-d6) δ ppm 8.07 (t, J=8.1 Hz, 1H), 7.06-7.25 (m, 7H), 6.85 (s, 1H), 6.33 (d, J=3.0 Hz, 1H), 6.14 (d, J=2.0 Hz, 1H), 4.96 (q, J=6.9 Hz, 1H), 4.55 (br d, J=10.5 Hz, 1H), 3.22-3.31 (m, 1H), 2.85-3.06 (m, 2H), 2.71-2.79 (m, 2H), 2.37-2.44 (m, 1H), 1.94-2.02 (m, 1H), 1.55 (d, J=6.6 Hz, 3H), 1.18-1.40 (m, 6H), 0.53-0.59 (m, 2H), 0.31-0.36 (m, 2H).

Compound 31

Major Rotamer (65%)
¹H-NMR (500 MHz, DMSO-d6) δ ppm 8.29 (dd, J=6.6, 3.2 Hz, 2H), 7.98 (t, J=8.0 Hz, 1H), 7.61-7.71 (m, 4H), 7.45 (s, 1H), 7.34 (d, J=7.6 Hz, 1H), 7.08-7.27 (m, 6H), 5.64 (q, J=6.6 Hz, 1H), 4.00 (br dd, J=13.9, 3.8 Hz, 1H), 3.50-3.58 (m, 1H), 3.03-3.11 (m, 1H), 2.77 (s, 3H), 2.73-2.77 (m, 1H), 2.25 (dt, J=8.8, 4.7 Hz, 1H), 1.74-1.80 (m, 1H), 1.56 (d, J=6.6 Hz, 3H), 1.32-1.38 (m, 1H), 1.10-1.15 (m, 1H).
Minor Rotamer (35%)
¹H-NMR (500 MHz, DMSO-d6) δ ppm 8.26 (dd, J=6.6, 2.8 Hz, 2H), 7.98 (t, J=8.0 Hz, 1H), 7.61-7.71 (m, 4H), 7.41 (s, 1H), 7.08-7.27 (m, 7H), 5.14 (q, J=6.6 Hz, 1H), 4.60 (br dd, J=12.9, 4.1 Hz, 1H), 3.50-3.58 (m, 1H), 2.92-3.00 (m, 1H), 2.85-2.91 (m, 1H), 2.77 (s, 3H), 2.25 (dt, J=8.8, 4.7 Hz, 1H), 1.74-1.80 (m, 1H), 1.61 (d, J=6.6 Hz, 3H), 1.32-1.38 (m, 1H), 1.10-1.15 (m, 1H).

Compound 32

Major Rotamer (65%)
¹H-NMR (500 MHz, DMSO-d6) δ ppm 8.29 (dd, J=6.5, 3.0 Hz, 2H), 7.98 (t, J=8.0 Hz, 1H), 7.62-7.73 (m, 4H), 7.45 (s, 1H), 7.34 (d, J=7.6 Hz, 1H), 7.09-7.27 (m, 6H), 5.64 (q, J=6.8 Hz, 1H), 4.00 (br dd, J=13.9, 3.8 Hz, 1H), 3.50-3.58 (m, 1H), 3.02-3.12 (m, 1H), 2.79 (s, 3H), 2.73-2.78 (m, 1H), 2.23-2.29 (m, 1H), 1.76-1.83 (m, 1H), 1.56 (d, J=6.9 Hz, 3H), 1.33-1.40 (m, 1H), 1.10-1.16 (m, 1H).
Minor Rotamer (35%)
¹H-NMR (500 MHz, DMSO-d6) δ ppm 8.26 (dd, J=6.6, 2.8 Hz, 2H), 7.98 (t, J=8.0 Hz, 1H), 7.62-7.73 (m, 4H), 7.41 (s, 1H), 7.09-7.27 (m, 7H), 5.15 (q, J=6.6 Hz, 1H), 4.60 (br dd, J=12.8, 4.3 Hz, 1H), 3.50-3.58 (m, 1H), 2.85-3.12 (m, 2H), 2.79 (s, 3H), 2.23-2.29 (m, 1H), 1.76-1.83 (m, 1H), 1.61 (d, J=6.9 Hz, 3H), 1.33-1.40 (m, 1H), 1.10-1.16 (m, 1H).

Compound 33

Major Rotamer (65%)
¹H-NMR (400 MHz, DMSO-d6) δ ppm 8.07 (t, J=8.1 Hz, 1H), 7.62 (br s, 1H), 7.32 (br d, J=7.1 Hz, 1H), 7.06-7.26 (m, 6H), 6.89 (s, 1H), 5.59 (q, J=6.6 Hz, 1H), 3.81 (br dd, J=13.9, 3.8 Hz, 1H), 3.55 (s, 3H), 3.41-3.51 (m, 1H), 2.86-3.06 (m, 2H), 2.71-2.80 (m, 1H), 2.66-2.71 (m, 1H), 1.99-2.09 (m, 1H), 1.52 (d, J=7.1 Hz, 3H), 1.20-1.39 (m, 6H).
Minor Rotamer (35%)
¹H-NMR (400 MHz, DMSO-d6) δ ppm 8.07 (t, J=8.1 Hz, 1H), 7.62 (br s, 1H), 7.06-7.26 (m, 7H), 6.85 (s, 1H), 4.96 (q, J=6.6 Hz, 1H), 4.51-4.60 (m, 1H), 3.55 (s, 3H), 3.23-3.31 (m, 1H), 2.86-3.06 (m, 3H), 2.71-2.80 (m, 1H), 1.99-2.09 (m, 1H), 1.55 (br d, J=7.1 Hz, 3H), 1.20-1.39 (m, 6H).

Compound 34

Major Rotamer (65%)
¹H-NMR (500 MHz, DMSO-d6) δ ppm 8.22 (d, J=4.4 Hz, 1H), 8.08 (t, J=8.2 Hz, 1H), 7.32 (d, J=7.3 Hz, 1H), 7.05-7.25 (m, 6H), 6.89 (s, 1H), 5.59 (q, J=6.5 Hz, 1H), 3.82 (br dd, J=13.7, 3.9 Hz, 1H), 3.42-3.51 (m, 1H), 2.83-3.05 (m, 3H), 2.71 (br d, J=16.1 Hz, 1H), 1.97-2.03 (m, 1H), 1.81 (s, 3H), 1.52 (d, J=6.9 Hz, 3H), 1.31-1.39 (m, 2H), 1.22-1.31 (m, 4H).
Minor Rotamer (35%)
¹H-NMR (500 MHz, DMSO-d6) δ ppm 8.22 (d, J=4.4 Hz, 1H), 8.08 (t, J=8.2 Hz, 1H), 7.05-7.25 (m, 7H), 6.86 (s, 1H), 4.96 (q, J=6.8 Hz, 1H), 4.55 (br dd, J=12.6, 3.5 Hz, 1H), 3.23-3.31 (m, 1H), 2.83-3.05 (m, 4H), 1.97-2.03 (m, 1H), 1.81 (s, 3H), 1.55 (d, J=6.6 Hz, 3H), 1.31-1.39 (m, 2H), 1.22-1.31 (m, 4H).

Compound 35

Major Rotamer (65%)
¹H-NMR (400 MHz, DMSO-d6) δ ppm 8.45 (d, J=4.0 Hz, 1H), 8.07 (t, J=8.3 Hz, 1H), 7.32 (d, J=7.1 Hz, 1H), 7.05-7.26 (m, 6H), 6.89 (s, 1H), 5.59 (q, J=7.1 Hz, 1H), 3.81 (br dd, J=13.9, 3.8 Hz, 1H), 3.41-3.51 (m, 1H), 2.82-3.07 (m, 3H), 2.71 (br d, J=16.7 Hz, 1H), 1.99-2.06 (m, 1H), 1.52 (d, J=7.1 Hz, 3H), 1.46-1.51 (m, 1H), 1.31-1.39 (m, 2H), 1.21-1.31 (m, 4H), 0.62-0.72 (m, 4H).
Minor Rotamer (35%)
¹H-NMR (400 MHz, DMSO-d6) δ ppm 8.45 (d, J=4.0 Hz, 1H), 8.07 (t, J=8.3 Hz, 1H), 7.05-7.26 (m, 7H), 6.85 (s, 1H), 4.96 (q, J=6.7 Hz, 1H), 4.51-4.59 (m, 1H), 3.21-3.31 (m, 1H), 2.82-3.07 (m, 4H), 1.99-2.06 (m, 1H), 1.54 (d, J=6.6 Hz, 3H), 1.46-1.51 (m, 1H), 1.31-1.39 (m, 2H), 1.21-1.31 (m, 4H), 0.62-0.72 (m, 4H).

Compound 36

Major Rotamer (65%)
¹H-NMR (400 MHz, DMSO-d6) δ ppm 8.08 (t, J=7.8 Hz, 1H), 7.68 (d, J=3.0 Hz, 1H), 7.32 (d, J=7.1 Hz, 1H), 7.05-7.25 (m, 6H), 6.90 (s, 1H), 5.59 (q, J=6.7 Hz, 1H), 3.81 (br dd, J=14.1, 4.0 Hz, 1H), 3.41-3.52 (m, 1H), 2.85-3.07 (m, 2H), 2.98 (s, 3H), 2.75-2.81 (m, 1H), 2.71 (br d, J=16.2 Hz, 1H), 2.19-2.26 (m, 1H), 1.52 (d, J=6.6 Hz, 3H), 1.24-1.39 (m, 6H).
Minor Rotamer (65%)
¹H-NMR (400 MHz, DMSO-d6) δ ppm 8.08 (t, J=7.8 Hz, 1H), 7.68 (d, J=3.0 Hz, 1H), 7.05-7.25 (m, 7H), 6.86 (s, 1H), 4.96 (q, J=7.1 Hz, 1H), 4.55 (br d, J=12.1 Hz, 1H), 3.22-3.30 (m, 1H), 2.85-3.07 (m, 3H), 2.98 (s, 3H), 2.75-2.81 (m, 1H), 2.19-2.26 (m, 1H), 1.55 (d, J=7.1 Hz, 3H), 1.24-1.39 (m, 6H).

Compound 37

Major Rotamer (65%)

¹H-NMR (400 MHz, DMSO-d6) δ ppm 8.07 (t, J=8.1 Hz, 1H), 7.32 (d, J=7.6 Hz, 1H), 7.04-7.26 (m, 6H), 6.89 (s, 1H), 5.59 (q, J=6.6 Hz, 1H), 5.05 (dd, J=7.6, 2.5 Hz, 1H), 3.81 (br dd, J=13.6, 4.0 Hz, 1H), 3.41-3.52 (m, 1H), 2.82-3.06 (m, 2H), 2.71 (br d, J=16.2 Hz, 1H), 2.52-2.59 (m, 1H partially obscured by DMSO peak), 2.02-2.10 (m, 1H), 1.52 (d, J=6.6 Hz, 3H), 1.21-1.41 (m, 12H).

Minor Rotamer (35%)

¹H-NMR (400 MHz, DMSO-d6) δ ppm 8.07 (t, J=8.1 Hz, 1H), 7.04-7.26 (m, 7H), 6.85 (s, 1H), 5.05 (dd, J=7.6, 2.5 Hz, 1H), 4.96 (q, J=6.6 Hz, 1H), 4.55 (br d, J=12.1 Hz, 1H), 3.22-3.30 (m, 1H), 2.82-3.06 (m, 3H), 2.52-2.59 (m, 1H partially obscured by DMSO peak), 2.02-2.10 (m, 1H), 1.55 (d, J=7.1 Hz, 3H), 1.21-1.41 (m, 12H).

Compound 38

Major Rotamer (65%)

¹H-NMR (500 MHz, DMSO-d6) δ ppm 8.05 (t, J=8.0 Hz, 1H), 7.32 (d, J=7.6 Hz, 1H), 7.15-7.25 (m, 3H), 6.99-7.14 (m, 3H), 6.88 (s, 1H), 5.78 (s, 1H), 5.59 (q, J=6.6 Hz, 1H), 3.81 (br dd, J=13.7, 3.6 Hz, 1H), 3.43-3.51 (m, 2H), 2.83-3.06 (m, 2H), 2.72 (br d, J=16.1 Hz, 1H), 2.00-2.06 (m, 1H), 1.52 (d, J=6.9 Hz, 3H), 1.23-1.38 (m, 4H), 1.17-1.22 (m, 1H), 1.08 (q, J=6.3 Hz, 1H).

Minor Rotamer (35%)

¹H-NMR (500 MHz, DMSO-d6) δ ppm 8.05 (t, J=8.0 Hz, 1H), 7.15-7.25 (m, 3H), 6.99-7.14 (m, 4H), 6.85 (s, 1H), 5.79 (s, 1H), 4.96 (q, J=6.7 Hz, 1H), 4.55 (br d, J=12.3 Hz, 1H), 3.43-3.51 (m, 1H), 3.23-3.29 (m, 1H), 2.83-3.06 (m, 3H), 2.00-2.06 (m, 1H), 1.55 (d, J=6.6 Hz, 3H), 1.23-1.38 (m, 4H), 1.17-1.22 (m, 1H), 1.08 (q, J=6.3 Hz, 1H).

Compound 39

Major Rotamer (65%)

¹H-NMR (500 MHz, DMSO-d6) δ ppm 8.08 (t, J=8.0 Hz, 1H), 7.32 (d, J=7.3 Hz, 1H), 7.06-7.26 (m, 6H), 6.89 (s, 1H), 6.52-6.79 (m, 2H), 5.59 (q, J=6.5 Hz, 1H), 4.06-4.11 (m, 1H), 3.82 (br dd, J=13.4, 3.6 Hz, 1H), 3.42-3.51 (m, 1H), 2.83-3.06 (m, 2H), 2.71 (br d, J=16.4 Hz, 1H), 2.22-2.28 (m, 1H), 1.52 (d, J=6.9 Hz, 3H), 1.32-1.40 (m, 3H), 1.24-1.32 (m, 3H).

Minor Rotamer (35%)

¹H-NMR (500 MHz, DMSO-d6) δ ppm 8.08 (t, J=8.0 Hz, 1H), 7.06-7.26 (m, 7H), 6.86 (s, 1H), 6.70 (br s, 1H), 6.61 (br s, 1H), 4.96 (q, J=6.8 Hz, 1H), 4.55 (br dd, J=12.6, 3.5 Hz, 1H), 4.06-4.11 (m, 1H), 3.23-3.30 (m, 1H), 2.83-3.06 (m, 3H), 2.22-2.28 (m, 1H), 1.55 (d, J=6.9 Hz, 3H), 1.32-1.40 (m, 3H), 1.24-1.32 (m, 3H).

Compound 40

Major Rotamer (65%)

¹H-NMR (500 MHz, DMSO-d6) δ ppm 8.08 (t, J=8.0 Hz, 1H), 7.32 (d, J=7.3 Hz, 1H), 7.06-7.25 (m, 7H), 6.89 (s, 1H), 5.59 (q, J=6.6 Hz, 1H), 4.10 (dt, J=6.3, 3.5 Hz, 1H), 3.82 (br dd, J=13.6, 3.8 Hz, 1H), 3.42-3.50 (m, 1H), 2.83-3.05 (m, 2H), 2.71 (br d, J=16.4 Hz, 1H), 2.58 (d, J=4.7 Hz, 3H), 2.22-2.28 (m, 1H), 1.52 (d, J=6.6 Hz, 3H), 1.23-1.39 (m, 6H).

Minor Rotamer (35%)

¹H-NMR (500 MHz, DMSO-d6) δ ppm 8.08 (t, J=8.0 Hz, 1H), 7.06-7.25 (m, 8H), 6.86 (s, 1H), 4.96 (q, J=6.4 Hz, 1H), 4.55 (br dd, J=12.3, 3.5 Hz, 1H), 4.10 (dt, J=6.3, 3.5 Hz, 1H), 3.24-3.31 (m, 1H), 2.83-3.05 (m, 3H), 2.58 (d, J=4.7 Hz, 3H), 2.22-2.28 (m, 1H), 1.55 (d, J=6.9 Hz, 3H), 1.23-1.39 (m, 6H).

Compound 41

Major Rotamer (65%)

¹H-NMR (500 MHz, DMSO-d6) δ ppm 8.12 (t, J=8.2 Hz, 1H), 7.32 (d, J=7.6 Hz, 1H), 7.06-7.30 (m, 6H), 6.90 (s, 1H), 5.59 (q, J=6.4 Hz, 1H), 4.61 (t, J=5.4 Hz, 1H), 3.82 (br dd, J=13.7, 3.9 Hz, 1H), 3.63 (quin, J=8.4 Hz, 1H), 3.57 (dd, J=6.8, 5.5 Hz, 2H), 3.43-3.51 (m, 1H), 2.83-3.06 (m, 2H), 2.72 (br d, J=15.8 Hz, 1H), 2.37-2.42 (m, 1H), 2.19 (dd, J=8.4, 6.8 Hz, 4H), 1.53 (d, J=6.9 Hz, 3H), 1.32-1.39 (m, 2H), 1.25-1.32 (m, 2H).

Minor Rotamer (35%)

¹H-NMR (500 MHz, DMSO-d6) δ ppm 8.12 (t, J=8.2 Hz, 1H), 7.06-7.30 (m, 7H), 6.86 (s, 1H), 4.97 (q, J=6.9 Hz, 1H), 4.61 (t, J=5.4 Hz, 1H), 4.55 (br dd, J=13.1, 3.0 Hz, 1H), 3.63 (quin, J=8.4 Hz, 1H), 3.57 (dd, J=6.8, 5.5 Hz, 2H), 3.24-3.31 (m, 1H), 2.83-3.06 (m, 3H), 2.37-2.42 (m, 1H), 2.19 (dd, J=8.4, 6.8 Hz, 4H), 1.55 (d, J=6.6 Hz, 3H), 1.32-1.39 (m, 2H), 1.25-1.32 (m, 2H).

Compound 42

Major Rotamer (65%)

¹H-NMR (500 MHz, DMSO-d6) δ ppm 8.11 (br t, J=8.0 Hz, 1H), 7.32 (br d, J=7.6 Hz, 1H), 7.05-7.26 (m, 6H), 6.90 (s, 1H), 5.59 (q, J=6.6 Hz, 1H), 4.51 (t, J=5.2 Hz, 1H), 3.82 (br dd, J=13.4, 3.3 Hz, 1H), 3.42-3.52 (m, 2H), 3.40 (t, J=5.2 Hz, 2H), 2.83-3.06 (m, 2H), 2.72 (br d, J=16.1 Hz, 1H), 2.31-2.45 (m, 3H), 1.85-1.95 (m, 2H), 1.53 (br d, J=6.9 Hz, 3H), 1.32-1.40 (m, 2H), 1.21-1.31 (m, 2H).

Minor Rotamer (35%)

¹H-NMR (500 MHz, DMSO-d6) δ ppm 8.11 (br t, J=8.0 Hz, 1H), 7.05-7.26 (m, 7H), 6.86 (s, 1H), 4.97 (q, J=6.7 Hz, 1H), 4.53-4.59 (m, 1H), 4.51 (t, J=5.2 Hz, 1H), 3.42-3.52 (m, 1H), 3.40 (t, J=5.2 Hz, 2H), 3.23-3.31 (m, 1H), 2.83-3.06 (m, 3H), 2.31-2.45 (m, 3H), 1.85-1.95 (m, 2H), 1.55 (br d, J=6.6 Hz, 3H), 1.32-1.40 (m, 2H), 1.21-1.31 (m, 2H).

Compound 43

Major Rotamer (65%)

¹H-NMR (500 MHz, DMSO-d6) δ ppm 8.13 (t, J=8.0 Hz, 1H), 7.06-7.35 (m, 7H), 6.90 (s, 1H), 6.35-6.70 (br s, 2H), 5.59 (q, J=6.8 Hz, 1H), 4.11 (d, J=7.3 Hz, 2H), 3.82 (br dd, J=13.9, 3.8 Hz, 1H), 3.73 (quin, J=8.6 Hz, 1H), 3.43-3.52 (m, 1H), 2.86-3.06 (m, 2H), 2.72 (br d, J=16.1 Hz, 1H), 2.54-2.60 (m, 1H), 2.24-2.32 (m, 2H), 2.16-2.23 (m, 2H), 1.53 (d, J=6.6 Hz, 3H), 1.32-1.39 (m, 2H), 1.25-1.32 (m, 2H).

Minor Rotamer (35%)

¹H-NMR (500 MHz, DMSO-d6) δ ppm 8.13 (t, J=8.0 Hz, 1H), 7.06-7.35 (m, 7H), 6.86 (s, 1H), 6.35-6.70 (br s, 2H), 4.97 (q, J=6.6 Hz, 1H), 4.53-4.59 (m, 1H), 4.11 (d, J=7.3 Hz, 2H), 3.73 (quin, J=8.6 Hz, 1H), 3.24-3.31 (m, 1H), 2.86-3.06 (m, 3H), 2.54-2.60 (m, 1H), 2.24-2.32 (m, 2H), 2.16-2.23 (m, 2H), 1.55 (d, J=6.6 Hz, 3H), 1.32-1.39 (m, 2H), 1.25-1.32 (m, 2H).

Compound 44

Major Rotamer (65%)
¹H-NMR (500 MHz, DMSO-d6) δ ppm 8.12 (br t, J=8.0 Hz, 1H), 7.32 (br d, J=7.6 Hz, 1H), 7.06-7.29 (m, 6H), 6.90 (s, 1H), 6.32-6.69 (br s, 2H), 5.59 (q, J=6.9 Hz, 1H), 3.94 (d, J=6.0 Hz, 2H), 3.78-3.86 (m, 1H), 3.41-3.51 (m, 2H), 2.83-3.06 (m, 2H), 2.72 (br d, J=16.7 Hz, 1H), 2.37-2.46 (m, 2H), 1.91 (q, J=10.2 Hz, 2H), 1.53 (br d, J=6.9 Hz, 3H), 1.32-1.40 (m, 2H), 1.19-1.31 (m, 2H).

Minor Rotamer (35%)
¹H-NMR (500 MHz, DMSO-d6) δ ppm 8.12 (br t, J=8.0 Hz, 1H), 7.06-7.29 (m, 7H), 6.86 (s, 1H), 6.32-6.69 (br s, 2H), 4.97 (q, J=6.5 Hz, 1H), 4.52-4.59 (m, 1H), 3.94 (d, J=6.0 Hz, 2H), 3.41-3.51 (m, 1H), 3.23-3.31 (m, 1H), 2.83-3.06 (m, 3H), 2.37-2.46 (m, 2H), 1.91 (q, J=10.2 Hz, 2H), 1.55 (br d, J=6.6 Hz, 3H), 1.32-1.40 (m, 2H), 1.19-1.31 (m, 2H).

Compound 45

Major Rotamer (65%)
¹H-NMR (500 MHz, DMSO-d6) δ ppm 8.12 (t, J=7.9 Hz, 1H), 7.07-7.34 (m, 8H), 6.90 (s, 1H), 6.76 (br s, 1H), 5.59 (q, J=6.7 Hz, 1H), 3.79-3.85 (m, 1H), 3.67 (quin, J=8.4 Hz, 1H), 3.43-3.51 (m, 1H), 2.87-3.06 (m, 2H), 2.72 (br d, J=16.4 Hz, 1H), 2.36 (s, 2H), 2.25-2.33 (m, 2H), 2.11-2.19 (m, 2H), 1.53 (d, J=6.9 Hz, 3H), 1.32-1.40 (m, 2H), 1.25-1.31 (m, 2H).

Minor Rotamer (35%)
¹H-NMR (500 MHz, DMSO-d6) δ ppm 8.12 (t, J=7.9 Hz, 1H), 7.07-7.34 (m, 8H), 6.86 (s, 1H), 6.76 (br s, 1H), 4.97 (q, J=6.6 Hz, 1H), 4.52-4.59 (m, 1H), 3.67 (quin, J=8.4 Hz, 1H), 3.24-3.31 (m, 1H), 2.87-3.06 (m, 3H), 2.36 (s, 2H), 2.25-2.33 (m, 2H), 2.11-2.19 (m, 2H), 1.55 (d, J=6.6 Hz, 3H), 1.32-1.40 (m, 2H), 1.25-1.31 (m, 2H).

Compound 46

Major Rotamer (65%)
¹H-NMR (500 MHz, DMSO-d6) δ ppm 8.11 (br t, J=7.9 Hz, 1H), 7.32 (d, J=7.6 Hz, 1H), 7.05-7.27 (m, 7H), 6.90 (s, 1H), 6.72 (br s, 1H), 5.59 (q, J=6.6 Hz, 1H), 3.81 (br dd, J=13.4, 3.6 Hz, 1H), 3.38-3.52 (m, 2H), 2.83-3.07 (m, 2H), 2.72 (br d, J=16.4 Hz, 1H), 2.54-2.62 (m, 2H), 2.21 (d, J=6.9 Hz, 2H), 1.83 (q, J=10.2 Hz, 2H), 1.52 (d, J=6.9 Hz, 3H), 1.32-1.39 (m, 2H), 1.22-1.31 (m, 2H).

Minor Rotamer (35%)
¹H-NMR (500 MHz, DMSO-d6) δ ppm 8.11 (br t, J=7.9 Hz, 1H), 7.05-7.27 (m, 8H), 6.86 (s, 1H), 6.72 (br s, 1H), 4.97 (q, J=6.8 Hz, 1H), 4.52-4.60 (m, 1H), 3.38-3.52 (m, 1H), 3.23-3.30 (m, 1H), 2.83-3.07 (m, 3H), 2.54-2.62 (m, 2H), 2.21 (d, J=6.9 Hz, 2H), 1.83 (q, J=10.2 Hz, 2H), 1.55 (d, J=6.9 Hz, 3H), 1.32-1.39 (m, 2H), 1.22-1.31 (m, 2H).

Compound 47

Major Rotamer (65%)
¹H-NMR (500 MHz, DMSO-d6) δ ppm 8.12 (t, J=7.9 Hz, 1H), 7.77 (br d, J=4.1 Hz, 1H), 7.32 (d, J=7.3 Hz, 1H), 7.06-7.30 (m, 6H), 6.90 (s, 1H), 5.59 (q, J=6.7 Hz, 1H), 3.82 (br dd, J=13.4, 3.6 Hz, 1H), 3.67 (quin, J=8.2 Hz, 1H), 3.43-3.51 (m, 1H), 2.82-3.06 (m, 2H), 2.72 (br d, J=16.4 Hz, 1H), 2.59-2.63 (m, 1H), 2.57 (d, J=4.7 Hz, 3H), 2.38 (d, J=8.2 Hz, 2H), 2.25-2.33 (m, 2H), 2.10-2.17 (m, 2H), 1.52 (d, J=6.9 Hz, 3H), 1.32-1.38 (m, 2H), 1.25-1.32 (m, 2H).

Minor Rotamer (35%)
¹H-NMR (500 MHz, DMSO-d6) δ ppm 8.12 (t, J=7.9 Hz, 1H), 7.77 (br d, J=4.1 Hz, 1H), 7.06-7.30 (m, 7H), 6.86 (s, 1H), 4.97 (q, J=6.6 Hz, 1H), 4.52-4.59 (m, 1H), 3.67 (quin, J=8.2 Hz, 1H), 3.23-3.31 (m, 1H), 2.82-3.06 (m, 3H), 2.59-2.63 (m, 1H), 2.57 (d, J=4.7 Hz, 3H), 2.38 (d, J=8.2 Hz, 2H), 2.25-2.33 (m, 2H), 2.10-2.17 (m, 2H), 1.55 (d, J=6.6 Hz, 3H), 1.32-1.38 (m, 2H), 1.25-1.32 (m, 2H).

Compound 48

Major Rotamer (65%)
¹H-NMR (500 MHz, DMSO-d6) δ ppm 8.11 (t, J=8.0 Hz, 1H), 7.69 (br d, J=3.8 Hz, 1H), 7.32 (d, J=7.6 Hz, 1H), 7.05-7.26 (m, 6H), 6.90 (s, 1H), 5.59 (q, J=6.5 Hz, 1H), 3.81 (br dd, J=13.9, 4.1 Hz, 1H), 3.39-3.51 (m, 2H), 2.83-3.06 (m, 2H), 2.72 (br d, J=16.4 Hz, 1H), 2.56 (d, J=4.7 Hz, 3H), 2.54-2.55 (m, 1H), 2.43-2.48 (m, 2H), 2.22 (d, J=7.3 Hz, 2H), 1.78-1.86 (m, 2H), 1.52 (d, J=6.6 Hz, 3H), 1.32-1.39 (m, 2H), 1.25-1.31 (m, 2H).

Minor Rotamer (35%)
¹H-NMR (500 MHz, DMSO-d6) δ ppm 8.11 (t, J=8.0 Hz, 1H), 7.69 (br d, J=3.8 Hz, 1H), 7.05-7.26 (m, 7H), 6.86 (s, 1H), 4.97 (q, J=6.6 Hz, 1H), 4.55 (br dd, J=13.2, 3.5 Hz, 1H), 3.39-3.51 (m, 1H), 3.23-3.31 (m, 1H), 2.83-3.06 (m, 3H), 2.56 (d, J=4.7 Hz, 3H), 2.54-2.55 (m, 1H), 2.43-2.48 (m, 2H), 2.22 (d, J=7.3 Hz, 2H), 1.78-1.86 (m, 2H), 1.55 (d, J=6.6 Hz, 3H), 1.32-1.39 (m, 2H), 1.25-1.31 (m, 2H).

Compound 49

Major Rotamer (65%)
¹H-NMR (500 MHz, DMSO-d6) δ ppm 9.15 (d, J=10.4 Hz, 1H), 7.70 (br s, 1H), 7.61 (d, J=12.0 Hz, 1H), 7.32 (d, J=7.3 Hz, 1H), 7.21-7.26 (m, 1H), 7.15-7.21 (m, 3H), 6.99 (br s, 1H), 6.94 (s, 1H), 5.59 (q, J=6.9 Hz, 1H), 3.80 (br ddd, J=13.6, 4.7, 1.3 Hz, 1H), 3.42-3.51 (m, 1H), 2.83-3.05 (m, 2H), 2.71 (br d, J=16.1 Hz, 1H), 2.54-2.57 (m, 1H), 2.20-2.26 (m, 1H), 1.52 (d, J=6.6 Hz, 3H), 1.39-1.47 (m, 2H), 1.25-1.38 (m, 4H).

Minor Rotamer (35%)
¹H-NMR (500 MHz, DMSO-d6) δ ppm 9.15 (d, J=10.4 Hz, 1H), 7.70 (br s, 1H), 7.61 (d, J=12.0 Hz, 1H), 7.15-7.21 (m, 3H), 7.10-7.15 (m, 1H), 7.07 (d, J=7.3 Hz, 1H), 6.99 (br s, 1H), 6.90 (s, 1H), 4.95 (q, J=6.1 Hz, 1H), 4.55 (br dd, J=12.9, 3.2 Hz, 1H), 3.23-3.30 (m, 1H), 2.83-3.05 (m, 3H), 2.54-2.57 (m, 1H), 2.20-2.26 (m, 1H), 1.55 (br d, J=6.9 Hz, 3H), 1.39-1.47 (m, 2H), 1.25-1.38 (m, 4H).

Compound 50

Major Rotamer (65%)
¹H-NMR (500 MHz, DMSO-d6) δ ppm 12.11 (br s, 1H), 9.17 (d, J=10.4 Hz, 1H), 7.68 (d, J=11.7 Hz, 1H), 7.32 (d, J=7.6 Hz, 1H), 7.21-7.26 (m, 1H), 7.15-7.21 (m, 3H), 6.94 (s, 1H), 5.59 (q, J=6.6 Hz, 1H), 3.80 (br dd, J=13.6, 4.1 Hz, 1H), 3.43-3.51 (m, 1H), 3.27 (s, 3H), 2.84-3.05 (m, 2H), 2.74-2.79 (m, 1H), 2.71 (br d, J=16.4 Hz, 1H), 2.40-2.46 (m, 1H), 1.60-1.67 (m, 1H), 1.56-1.60 (m, 1H), 1.53 (d, J=6.6 Hz, 3H), 1.25-1.40 (m, 4H).

Minor Rotamer (35%)
¹H-NMR (500 MHz, DMSO-d6) δ ppm 12.11 (br s, 1H), 9.17 (d, J=10.4 Hz, 1H), 7.68 (d, J=11.7 Hz, 1H), 7.15-7.21 (m, 3H), 7.10-7.15 (m, 1H), 7.07 (d, J=7.9 Hz, 1H), 6.91 (s, 1H), 4.95 (q, J=6.6 Hz, 1H), 4.55 (br dd, J=11.8, 4.3 Hz, 1H), 3.27 (s, 3H), 3.24-3.29 (m, 1H), 2.84-3.05 (m, 3H), 2.74-2.79 (m, 1H), 2.40-2.46 (m, 1H), 1.60-1.67 (m, 1H), 1.56-1.60 (m, 1H), 1.55 (br d, J=7.3 Hz, 3H), 1.25-1.40 (m, 4H).

Compound 51

Major Rotamer (65%)
$^1$H-NMR (500 MHz, DMSO-d6) δ ppm 8.56 (br t, J=8.8 Hz, 1H), 7.71 (br s, 1H), 7.59 (br d, J=7.6 Hz, 1H), 7.32 (br d, J=7.6 Hz, 1H), 7.10-7.26 (m, 4H), 7.01 (br s, 1H), 6.93 (s, 1H), 5.59 (q, J=6.8 Hz, 1H), 3.80 (br d, J=13.9 Hz, 1H), 3.42-3.51 (m, 1H), 2.83-3.06 (m, 2H), 2.71 (br d, J=16.7 Hz, 1H), 2.17-2.23 (m, 1H), 1.52 (d, J=6.9 Hz, 3H), 1.39-1.44 (m, 1H), 1.32-1.39 (m, 3H), 1.22-1.32 (m, 3H).

Minor Rotamer (35%)
$^1$H-NMR (500 MHz, DMSO-d6) δ ppm 8.56 (br t, J=8.8 Hz, 1H), 7.71 (br s, 1H), 7.59 (br d, J=7.6 Hz, 1H), 7.10-7.26 (m, 4H), 7.05-7.09 (d, J=7.6 Hz, 1H), 7.01 (br s, 1H), 6.90 (s, 1H), 4.92-4.99 (m, 1H), 4.55 (br d, J=10.1 Hz, 1H), 3.24-3.31 (m, 1H), 2.83-3.06 (m, 3H), 2.17-2.23 (m, 1H), 1.55 (br d, J=6.6 Hz, 3H), 1.39-1.44 (m, 1H), 1.32-1.39 (m, 3H), 1.22-1.32 (m, 3H).

Compound 52

Major Rotamer (65%)
$^1$H-NMR (500 MHz, DMSO-d6) δ ppm 12.09 (s, 1H), 8.57-8.63 (m, 1H), 7.64 (d, J=7.9 Hz, 1H), 7.32 (d, J=7.6 Hz, 1H), 7.21-7.25 (m, 1H), 7.14-7.21 (m, 3H), 6.94 (s, 1H), 5.59 (q, J=6.6 Hz, 1H), 3.80 (br dd, J=13.2, 4.7 Hz, 1H), 3.43-3.50 (m, 1H), 3.24 (s, 3H), 2.84-3.06 (m, 2H), 2.69-2.76 (m, 2H), 1.53 (d, J=6.9 Hz, 3H), 1.50-1.59 (m, 3H), 1.25-1.39 (m, 4H).

Minor Rotamer (35%)
$^1$H-NMR (500 MHz, DMSO-d6) δ ppm 12.09 (s, 1H), 8.57-8.63 (m, 1H), 7.64 (d, J=7.9 Hz, 1H), 7.14-7.21 (m, 3H), 7.10-7.14 (m, 1H), 7.07 (d, J=7.3 Hz, 1H), 6.90 (s, 1H), 4.96 (q, J=6.7 Hz, 1H), 4.55 (br dd, J=13.1, 3.0 Hz, 1H), 3.27-3.31 (m, 1H), 3.24 (s, 3H), 2.84-3.06 (m, 3H), 2.69-2.76 (m, 1H), 1.54 (d, J=6.6 Hz, 3H), 1.50-1.59 (m, 3H), 1.25-1.39 (m, 4H).

Melting Points

For a number of compounds, melting points (m.p.) were determined with a differential scanning calorimeter DSC 1 (Mettler Toledo). Melting points were measured with a temperature gradient of 10° C./minute from 25° C. to 350° C. The reported values are peak values. Values are obtained with experimental uncertainties that are commonly associated with this analytical method.

| Co. No. | m.p. |
| --- | --- |
| 4 | 254.07° C. |
| 7 | 280.69° C. |
| 10 | 302.90° C. |
| 11 | 300.14° C. |
| 12 | 258.18° C. |
| 15 | 238.10° C. |
| 16 | 240.35° C. |
| 18 | 212.72° C. |
| 19 | 248.97° C. |
| 24 | 166.75° C. |
| 25 | 171.93° C. |
| 26 | 160.53° C. |
| 27 | 177.21° C. |
| 28 | 286.12° C. |
| 30 | 213.73° C. |
| 32 | 186.79° C. |
| 34 | 232.53° C. |

-continued

| Co. No. | m.p. |
| --- | --- |
| 35 | 255.06° C. |
| 36 | 196.25° C. |
| 39 | 297.87° C. |
| 40 | 274.46° C. |
| 42 | 129.63° C. |
| 44 | 300.97° C. |
| 48 | 143.95° C. |

Optical Rotation

The optical rotation was measured using a polarimeter with light at the wavelength of the D-line of sodium (589 nm) at a temperature of 20° C. in DMF as solvent.

| Co. No. | $[\alpha]_D^{20}$ | c (w/v %) |
| --- | --- | --- |
| 1 | +19.62° | 0.2549 |
| 2 | −276.67° | 0.3 |
| 3 | +117.96° | 0.284 |
| 4 | +148.62° | 0.29 |
| 5 | +154.43° | 0.2655 |
| 7 | +126.59° | 0.267 |
| 10 | +129.96° | 0.1385 |
| 11 | +115.17° | 0.29 |
| 12 | +122.67° | 0.3 |
| 13 | +171.58° | 0.285 |
| 14 | +124.77° | 0.1619 |
| 15 | +129.22° | 0.2221 |
| 16 | +119.88° | 0.2319 |
| 17 | +106.21° | 0.177 |
| 18 | +122.99° | 0.1805 |
| 19 | +116.64° | 0.1929 |
| 20 | +130.23° | 0.215 |
| 21 | +129.71° | 0.1673 |
| 22 | +129.62° | 0.26 |
| 23 | +140.37° | 0.27 |
| 24 | +164.07° | 0.27 |
| 25 | +156.3° | 0.27 |
| 26 | +167.31° | 0.26 |
| 27 | +151.72° | 0.29 |
| 28 | +142.07° | 0.29 |
| 29 | +169.63° | 0.27 |
| 30 | +77.04° | 0.27 |
| 31 | +143.73° | 0.295 |
| 32 | −193.46° | 0.306 |
| 33 | +56.12° | 0.2566 |
| 34 | +65° | 0.26 |
| 35 | +77.78° | 0.27 |
| 36 | +35.2° | 0.25 |
| 37 | +44.33° | 0.2301 |
| 38 | +16.25° | 0.277 |
| 39 | +41.57° | 0.267 |
| 40 | +53.79° | 0.264 |
| 41 | −35.1° | 0.302 |
| 42 | −35.5° | 0.262 |
| 43 | −32.18° | 0.289 |
| 44 | −31.44° | 0.299 |
| 45 | −28.97° | 0.252 |
| 46 | −29.6° | 0.277 |
| 47 | −31.34° | 0.268 |
| 48 | −27.94° | 0.272 |

E. Pharmacological Examples

E.1 Antiviral Activity

Black 384-well clear-bottom microtiter plates (Corning, Amsterdam, The Netherlands) were filled via acoustic drop ejection using the echo liquid handler (Labcyte, Sunnyvale, Calif.). 200 nL of compound stock solutions (100% DMSO) were transferred to the assay plates. 9 serial 4-fold dilutions of compound were made, creating per quadrant the same compound concentration. The assay was initiated by adding 10 μL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates. rgRSV224 virus is an engineered virus that includes an additional GFP gene (Hallak L K, Spillmann D, Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 μL of a HeLa cell suspension (3,000 cells/well) were plated. Medium, virus- and mock-infected controls were included in each test. The wells contain 0.05% DMSO per volume. Cells were incubated at 37° C. in a 5% $CO_2$ atmosphere. Three days post-virus exposure, viral replication was quantified by measuring GFP expression in the cells by an in house developed MSM laser microscope (Tibotec, Beerse, Belgium). The $EC_{50}$ was defined as the 50% inhibitory concentration for GFP expression. In parallel, compounds were incubated for three days in a set of white 384-well microtiter plates (Corning) and the cytotoxicity of compounds in HeLa cells was determined by measuring the ATP content of the cells using the ATPlite kit (Perkin Elmer, Zaventem, Belgium) according to the manufacturer's instructions. The $CC_{50}$ was defined as the 50% concentration for cytotoxicity.

TABLE antiviral data

| Co. No. | RSV HELA $EC_{50}$ (μm) | TOX HELA $CC_{50}$ (μm) |
|---|---|---|
| 1 | 0.062 | 41.832 |
| 2 | 0.084 | 42.528 |
| 3 | 0.319 | >100 |
| 4 | 0.120 | 44.004 |
| 5 | 0.098 | 41.824 |
| 7 | 0.030 | >100 |
| 8 | 0.332 | 34.366 |
| 9 | 0.098 | 20.115 |
| 10 | 0.014 | >25 |
| 11 | 0.044 | N.A. |
| 12 | 0.024 | >100 |
| 13 | 0.731 | 49.807 |
| 14 | 0.170 | >50 |
| 15 | 0.408 | >100 |
| 16 | 0.263 | >100 |
| 17 | 0.182 | >100 |
| 18 | 0.076 | >100 |
| 19 | 0.095 | >100 |
| 20 | 0.287 | >10 |
| 21 | 0.062 | >100 |
| 22 | 0.427 | 51.798 |
| 23 | 0.427 | 16.892 |
| 24 | 0.020 | 44.874 |
| 25 | 0.034 | 51.898 |
| 26 | 0.138 | 52.099 |
| 27 | 0.040 | 55.763 |
| 28 | 0.037 | 53.433 |
| 29 | 2.359 | >100 |
| 30 | 0.049 | 40.842 |
| 31 | 0.040 | 35.201 |
| 32 | 0.061 | 37.273 |
| 33 | 0.155 | >100 |
| 34 | 0.022 | >100 |
| 35 | 0.057 | >100 |
| 36 | 0.110 | >100 |
| 37 | 0.063 | 41.604 |
| 38 | 0.159 | 50.384 |
| 39 | 0.082 | 12.488 |
| 40 | 0.138 | >100 |

TABLE-continued antiviral data

| Co. No. | RSV HELA $EC_{50}$ (μm) | TOX HELA $CC_{50}$ (μm) |
|---|---|---|
| 41 | 0.152 | 49.770 |
| 42 | 0.263 | 69.225 |
| 43 | 0.307 | >100 |
| 44 | 0.332 | >100 |
| 45 | 0.146 | 29.549 |
| 46 | 0.145 | 30.407 |
| 47 | 0.148 | 25.758 |
| 48 | 0.151 | 23.933 |
| 49 | 0.150 | 10.760 |
| 50 | 0.389 | 53.276 |
| 51 | 0.047 | 25.857 |
| 52 | 0.117 | 65.298 |

N.A.: not available

F. Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

| F.1. Tablets | |
|---|---|
| Active ingredient | 5 to 50 mg |
| Di calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

F.2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

F.3. Injectable

A parenteral composition is prepared by stirring 1.5% by weight of active ingredient of the invention in 10% by volume propylene glycol in water.

| F.4. Ointment | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:
1. A compound of formula (I):

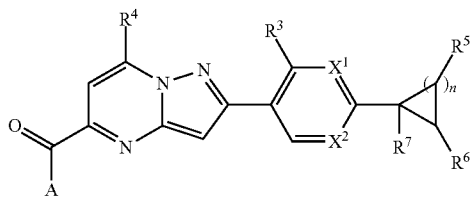

or any stereochemically isomeric form thereof, wherein
A is

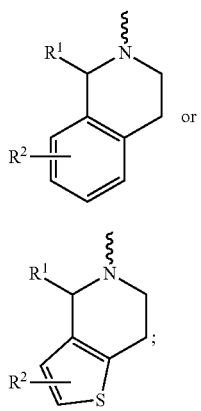

n is 1;
X$^1$ and X$^2$ are selected from X$^1$ is CH and X$^2$ is CH, or X$^1$ is N and X$^2$ is CH, or X$^1$ is CH and X$^2$ is N;
R$^1$ is CH$_3$;
R$^2$ is hydrogen or fluoro;
R$^3$ is fluoro;
R$^4$ is cyclopropyl or phenyl;
R$^5$ is hydrogen;
R$^6$ is —CH$_2$OH, —C(O)NHCH$_2$CCH, —C(O)NHCH$_2$CH$_2$CN, —C(O)NH-oxetanyl, —C(O)NHCH$_2$CH$_2$OH, —C(O)NHSO$_2$C$_{1-4}$alkyl, —C(O)NHSO$_2$-cyclopropyl, —NHC(O)NH— cyclopropyl, —NHCO$_2$CH$_3$, —NHC(O)CH$_3$, —NHC(O)-cyclopropyl, —NHSO$_2$CH$_3$, —NHP(O)(CH$_3$)$_2$, —OH, —OC(O)NH$_2$, —CH$_2$—OC(O)NH$_2$, —CH$_2$C(O)NH$_2$, —CH$_2$C(O)NHCH$_3$, 3-oxo-2,3-dihydro-1,2-oxazolyl, 5-oxo-4,5-dihydro-1,2,4-oxadiazolyl, or tetrazolyl; and
R$^7$ is hydrogen or fluoro;
provided that when R$^6$ is —NH(CO)-cyclopropyl, then X$^1$ is CH and X$^2$ is CH;
or a pharmaceutically acceptable acid addition salt thereof.

2. The compound of claim 1, wherein X$^1$ is CH and X$^2$ is CH.

3. The compound of claim 1, wherein X$^1$ is N and X$^2$ is CH, or X$^1$ is CH and X$^2$ is N.

4. The compound of claim 1, wherein radical A is of formula (a-1).

5. The compound of claim 1, wherein radical A is of formula (a-2).

6. The compound of claim 1, wherein n is 1.

7. A pharmaceutical composition comprising a pharmaceutically acceptable carrier and a compound of claim 1.

8. The pharmaceutical composition of claim 7, further comprising another antiviral agent.

9. The pharmaceutical composition of claim 8, wherein the other antiviral agent is a respiratory syncytial virus (RSV) inhibiting compound.

10. A process for preparing a pharmaceutical composition of claim 7 comprising intimately mixing a compound of claim 1 with a pharmaceutically acceptable carrier.

11. A method of treating a respiratory syncytial virus (RSV) infection comprising administering to a subject in need thereof an anti-virally effective amount of a compound of claim 1.

12. The compound of claim 1, wherein
R$^2$ is hydrogen.

13. A compound selected from:
[(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]methanol;
5-[(1R,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]-2,3-dihydro-1,2-oxazol-3-one;
(1R)-2-(7-Cyclopropyl-2-{2-fluoro-4-[(1S,2S)-2-(1H-1,2,3,4-tetrazol-5-yl)cyclopropyl]phenyl}pyrazolo[1,5-a]pyrimidine-5-carbonyl)-1-methyl-1,2,3,4-tetrahydroisoquinoline;
3-[(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]-4,5-dihydro-1,2,4-oxadiazol-5-one;
(1S,2S)-2-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-(prop-2-yn-1-yl)cyclopropane-1-carboxamide;
(1S,2S)—N-(2-Cyanoethyl)-2-(4-{7-cyclopropyl-5-[(1R)-1-methyl-1,2,3,4-tetrahydro-isoquinoline-2-carbonyl]pyrazolo[1,5-a]pyrimidin-2-yl}-3-fluorophenyl)cyclopropane-1-carboxamide;
(1S,2S)-2-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-(oxetan-3-yl)cyclopropane-1-carboxamide;
(1S,2S)-2-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-(2-hydroxyethyl)-cyclopropane-1-carboxamide;
(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-methanesulfonyl-cyclopropane-1-carboxamide;
(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-(ethanesulfonyl)-cyclopropane-1-carboxamide;
(1S,2S)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-(2-methylpropane-sulfonyl)-cyclopropane-1-carboxamide;

(1S,2S)—N-(Cyclopropanesulfonyl)-2-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-cyclopropane-1-carboxamide;

(1S,2S)-2-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-N-methanesulfonyl-cyclopropane-1-carboxamide;

1-Cyclopropyl-3-[(1S,2R)-2-(4-{7-cyclopropyl-5-[(1R)-1-methyl-1,2,3,4-tetrahydro-isoquinoline-2-carbonyl]pyrazolo[1,5-a]pyrimidin-2-yl}-3-fluorophenyl)cyclopropyl]urea;

(1*S,2*S)-2-(3-Fluoro-4-{5-[(1R)-1-methyl-1,2,3,4-tetrahydroisoquinoline-2-carbonyl]-7-phenylpyrazolo[1,5-a]pyrimidin-2-yl}phenyl)-N-methanesulfonyl-cyclopropane-1-carboxamide;

(1*R, 2*R)-2-(3-Fluoro-4-{5-[(1R)-1-methyl-1,2,3,4-tetrahydroisoquinoline-2-carbonyl]-7-phenylpyrazolo[1,5-a]pyrimidin-2-yl}phenyl)-N-methanesulfonyl-cyclopropane-1-carboxamide;

Methyl N-[(1S,2R)-2-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]carbamate;

N-[(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]acetamide;

N-[(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]cyclopropane-carboxamide;

N-[(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl]methanesulfonamide;

(1R)-2-(7-Cyclopropyl-2-{4-[(1R,2S)-2-[(dimethylphosphoryl)amino]cyclopropyl]-2-fluorophenyl}pyrazolo[1,5-a]pyrimidine-5-carbonyl)-1-methyl-1,2,3,4-tetrahydroisoquinoline;

(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropan-1-ol;

(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl carbamate;

(1S,2R)-2-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)cyclopropyl N-methylcarbamate;

Trans-2-(5-{7-Cyclopropyl-5-[(1R)-1-methyl-1,2,3,4-tetrahydroisoquinoline-2-carbonyl]pyrazolo[1,5-a]pyrimidin-2-yl}-4-fluoropyridin-2-yl)-N-methanesulfonylcyclopropane-1-carboxamide; and Trans-2-(5-{7-Cyclopropyl-5-[(1R)-1-methyl-1,2,3,4-tetrahydroisoquinoline-2-carbonyl]pyrazolo[1,5-a]pyrimidin-2-yl}-6-fluoropyridin-2-yl)-N-methanesulfonylcyclopropane-1-carboxamide;

and pharmaceutically acceptable salts thereof.

14. A method of preparing a compound of claim 1 comprising reacting an intermediate of formula (II):

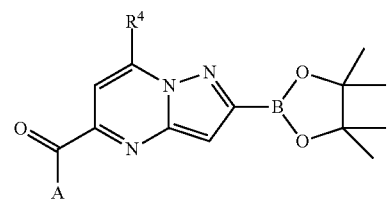

with an intermediate of formula (III):

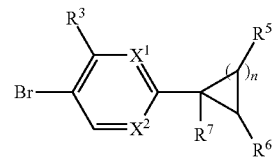

in a reaction-inert solvent to form the compound of Formula (I) or a pharmaceutically acceptable salt thereof as defined in claim 1.

15. The method of claim 14, wherein reacting comprises reacting in the presence of $PdCl_2(dtbpf)$ and $K_3PO_4$.

16. The method of claim 14, wherein the reaction-inert solvent is dioxane:$H_2O$.

* * * * *